United States Patent
Dean et al.

(10) Patent No.: US 12,350,206 B2
(45) Date of Patent: *Jul. 8, 2025

(54) SYSTEMS AND METHODS FOR PRESSURE INJURY MITIGATION

(71) Applicant: Luci Mobility, Inc., Brentwood, TN (US)

(72) Inventors: Jered H. Dean, Arvada, CO (US); Karl A. Grueschow, Westminster, CO (US); Dan A. Preston, Bainbridge Island, WA (US); Jean L. Minkel, New Windsor, NY (US)

(73) Assignee: Luci Mobility, Inc., Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,412

(22) Filed: Mar. 15, 2024

(65) Prior Publication Data

US 2024/0307239 A1    Sep. 19, 2024

Related U.S. Application Data

(63) Continuation of application No. 17/194,246, filed on Mar. 6, 2021, now Pat. No. 12,048,658.

(Continued)

(51) Int. Cl.
  *A61G 5/10*   (2006.01)
  *A61F 5/32*   (2006.01)
  *A61F 5/34*   (2006.01)

(52) U.S. Cl.
  CPC .............. *A61G 5/1043* (2013.01); *A61F 5/32* (2013.01); *A61F 5/34* (2013.01); *A61G 2203/20* (2013.01);

(Continued)

(58) Field of Classification Search
  CPC .............. A61G 5/1043; A61G 2203/20; A61G 2203/34; A61G 2203/70; A61F 5/32; A47C 7/467; B60N 2/665

(Continued)

(56) References Cited

U.S. PATENT DOCUMENTS 5,381,095 A  1/1995  Andrews
5,654,907 A  8/1997  Lange (Continued)

FOREIGN PATENT DOCUMENTS

EP    3182315 A1    6/2017
WO   2016110852 A2   7/2016

OTHER PUBLICATIONS

"Bluetooth Core Specification, v5.0," Bluetooth SIG Proprietary, Incorporated, Dec. 6, 2016, 2822 pages, Retrieved from the Internet: URL: https://www.bluetooth.org/en-us/specification/adopted-specifications.

(Continued)

*Primary Examiner* — Jose V Chen
(74) *Attorney, Agent, or Firm* — Polsinelli PC; Derek D. Donahoe

(57) ABSTRACT

A cushion has at least one fluid chamber and at least one cushion conduit to enable fluid to be added to or removed from the at least one fluid chamber of the cushion. A management system for the cushion has a pressure sensor to measure a pressure of fluid in the at least one fluid chamber of the cushion and to transmit a sensor report with the measured pressure, a tube having a first end connecting to the cushion conduit, a second end leading to the pressure sensor, and a valve to enable fluid to be added to or removed from the at least one fluid chamber of the cushion through the cushion conduit and a processor to receive the sensor report, determine a pressure value of the at least one fluid (Continued)

chamber of the cushion based on the measured pressure in the sensor report, and generate a status indicative of the pressure value of the fluid chamber of the cushion.

22 Claims, 31 Drawing Sheets

Related U.S. Application Data

(60) Provisional application No. 62/985,907, filed on Mar. 6, 2020.

(52) U.S. Cl.
CPC ...... *A61G 2203/34* (2013.01); *A61G 2203/70* (2013.01)

(58) Field of Classification Search
USPC .......... 297/217.2, 217.1, 283.1, 284.1, 284.6
See application file for complete search history.

(56) References Cited

U.S. PATENT DOCUMENTS

| | | | |
|---|---|---|---|
| 9,224,053 | B1 | 12/2015 | Ferguson et al. |
| 9,499,069 | B2 | 11/2016 | Hyde et al. |
| 10,096,228 | B1 | 10/2018 | Eulloqui et al. |
| 10,212,570 | B1 | 2/2019 | Ramalingam |
| 10,215,568 | B2 | 2/2019 | Klosinski, Jr. et al. |
| 10,656,652 | B2 | 5/2020 | Dean et al. |
| 10,857,679 | B1 | 12/2020 | Cousins et al. |
| 11,075,910 | B2 | 7/2021 | Dean et al. |
| 11,154,442 | B1 | 10/2021 | Dean et al. |
| 11,334,070 | B2 | 5/2022 | Dean et al. |
| 12,048,658 | B1 * | 7/2024 | Dean .................. A61G 5/1043 |
| 2002/0121394 | A1 | 9/2002 | Kamen et al. |
| 2003/0184729 | A1 | 10/2003 | Bowers |
| 2004/0262859 | A1 | 12/2004 | Turturiello et al. |
| 2005/0041813 | A1 | 2/2005 | Forest et al. |
| 2005/0083207 | A1 | 4/2005 | Smith et al. |
| 2005/0151360 | A1 | 7/2005 | Bertrand et al. |
| 2005/0154503 | A1 | 7/2005 | Jacobs |
| 2007/0038155 | A1 | 2/2007 | Kelly, Jr. et al. |
| 2007/0095582 | A1 | 5/2007 | Stuijt et al. |
| 2007/0198850 | A1 | 8/2007 | Martin et al. |
| 2008/0135321 | A1 | 6/2008 | Ripple et al. |
| 2008/0294300 | A1 | 11/2008 | Ashmore et al. |
| 2009/0292468 | A1 | 11/2009 | Wu et al. |
| 2010/0123574 | A1 | 5/2010 | Yamamura et al. |
| 2010/0312461 | A1 | 12/2010 | Haynie et al. |
| 2011/0190972 | A1 | 8/2011 | Timmons et al. |
| 2012/0052469 | A1 | 3/2012 | Sobel et al. |
| 2013/0197732 | A1 | 8/2013 | Pearlman et al. |
| 2013/0231800 | A1 | 9/2013 | Ricci |
| 2014/0052319 | A1 | 2/2014 | Taylor et al. |
| 2014/0146167 | A1 | 5/2014 | Friend et al. |
| 2014/0165159 | A1 | 6/2014 | Baade et al. |
| 2014/0210593 | A1 | 7/2014 | Cattermole et al. |
| 2014/0277888 | A1 | 9/2014 | Dastoor et al. |
| 2014/0335902 | A1 | 11/2014 | Guba et al. |
| 2015/0183431 | A1 | 7/2015 | Nanami |
| 2015/0209207 | A1 | 7/2015 | Cooper et al. |
| 2015/0244779 | A1 | 8/2015 | Fitzgerald |
| 2015/0268059 | A1 | 9/2015 | Borghesani |
| 2015/0346724 | A1 | 12/2015 | Jones et al. |
| 2015/0351981 | A1 | 12/2015 | Sazonov |
| 2015/0363986 | A1 | 12/2015 | Hoyos et al. |
| 2016/0009169 | A1 | 1/2016 | Biderman et al. |
| 2016/0012721 | A1 | 1/2016 | Biderman et al. |
| 2016/0025499 | A1 | 1/2016 | Moore et al. |
| 2016/0052137 | A1 | 2/2016 | Hyde et al. |
| 2016/0075177 | A1 | 3/2016 | Biderman et al. |
| 2017/0038787 | A1 | 2/2017 | Baker et al. |
| 2017/0043771 | A1 | 2/2017 | Ibanez-Guzman et al. |
| 2017/0095382 | A1 | 4/2017 | Wen et al. |
| 2017/0225760 | A1 | 8/2017 | Sidki et al. |
| 2017/0266069 | A1 | 9/2017 | Lozano et al. |
| 2018/0012433 | A1 | 1/2018 | Ricci |
| 2018/0042797 | A1 | 2/2018 | Richter |
| 2018/0135987 | A1 | 5/2018 | Evans et al. |
| 2018/0158197 | A1 | 6/2018 | Dasgupta et al. |
| 2019/0008461 | A1 | 1/2019 | Gupta et al. |
| 2019/0061772 | A1 | 2/2019 | Prinz |
| 2019/0064823 | A1 | 2/2019 | Jiang et al. |
| 2020/0121526 | A1 | 4/2020 | Cooper et al. |

OTHER PUBLICATIONS

Surmann H., et al., "An Autonomous Mobile Robot with a 3D Laser Range Finder for 3D Exploration and Digitalization of Indoor Environments," Robotics and Autonomous Systems, vol. 45, Sep. 22, 2003, pp. 181-198, Retrieved from URL: http://www2.inf.uni-osnabrueck.de/hertzberg/Papers/SurmannEtAIRAAS-2003.pdf.
"Part 15.1: Wireless Medium Access Control (MAC) and Physical Layer (PHY) Specifications for Wireless Personal Area Networks (WPANs)," IEEE Computer Society, IEEE Standard 802.15.1-2005, The Institute of Electrical and Electronics Engineers, Incorporated, New York, NY,USA, ISBN 0-7381-4707-9 SH95323, Jun. 14, 2005, 600 pages.
"Electric Vehicle Conductive Charging System—Part 1: General Requirements," International Standard, IEC Std.61851-1:2017, The International Electrotechnical Commission, Geneva, Switzerland,ISBN 978-2-8322-3766-3, Feb. 7, 2017, 292 pages.
"SAE Electric Vehicle and Plug in Hybrid Electric Vehicle Conductive Charge Coupler," Surface Vehicle Standard—J1772, SAE International, Warrendale, Pennsylvania, USA, Oct. 13, 2017,116 pages.
Narayanan V.K., et al., "Vision-Based Adaptive Assistance and Haptic Guidance for Safe Wheelchair Corridor Following," Computer Vision and Image Understanding, 2016, vol. 149, pp. 171-185.
"IEEE Guide for Wireless Access in Vehicular Environments (WAVE)—Architecture," IEEE Vehicular Technology Society, IEEE Standard 1609.0-2013, The Institute of Electrical and Electronics Engineers, Incorporation, New York, NY, USA, ISBN 978-0-7381-8756-3 STD98459,Mar. 5, 2014, 78 pages.
"IEEE Health Informatics Personal Health Device Communication—Part 20601: Application Profile—Optimized Exchange Protocol," IEEE Standards Association 11073-20601-2014, The Institute of Electrical and Electronics Engineers, Incorporation, New York, NY, USA, ISBN 978-0-7381-9314-4 STD98793, Oct. 10, 2014, 253 pages.
"IEEE Standard for Air Interface for Broadband Wireless Access Systems," IEEE Computer Society and the IEEE Microwave Theory and Techniques Society, IEEE Standard 802.16-2012, The Institute of Electrical and Electronics Engineers, Incorporated, New York, NY, USA, ISBN 978-0-7381-7291-0 STD97266, Aug. 17, 2012, 2544 pages.
"IEEE Standard for Information Technology—Portable Operating System Interface (POSIX)," Base Specifications, Issue 7, IEEE Standard 1003.1-2008, The Institute of Electrical and Electronics Engineers, Incorporated, New York, NY, USA, ISBN 978-0-7381-5798-6 STD95820, Dec. 1, 2008, 3968 pages.
"IEEE Standard for Information Technology—Telecommunications and Information Exchange Between Systems—Local and Metropolitan Area Networks—Specific Requirements—Part 2: Logical Link Control," ANSI/IEEE Standard 802.2, The Institute of Electrical and Electronics Engineers, Incorporated, New York, NY, USA, ISBN 1-55937-019-X, Dec. 31, 1989, 114 pages.
"IEEE Standard for Information Technology Telecommunications and Information Exchange between Systems Local and Metropolitan Area Networks Specific Requirements—Part 11: Wireless LAN Medium Access Control (MAC) and Physical Layer (PHY) Specifications," IEEE Standard 802.11-2016, The Institute of Electrical and Electronics Engineers, Incorporation, New York, NY, USA, ISBN 978-1-5044-3645-8 STDPD22369, Dec. 14, 2016, 3534 pages.
"IEEE Standard for Local and Metropolitan Area Networks: Overview and Architecture," IEEE Computer Society, IEEE Standard 802-2014, The Institute of Electrical and Electronics Engineers,

(56) References Cited

OTHER PUBLICATIONS

Incorporation, New York, NY, USA, ISBN 978-0-7381-9219-2 STD98723, Jun. 30, 2014, 74 pages.
"IEEE Standard for Low-Rate Wireless Networks Amendment 2: Ultra-Low Power Physical Layer," IEEE Computer Society, IEEE Standard 802.15.4q-2016, The Institute of Electrical and Electronics Engineers, Incorporation, New York, NY, USA, ISBN 978-1-5044-0782-3 STD20852, Apr. 29, 2016, 52 pages.
"IEEE Standard for Low-Rate Wireless Networks Amendment 4: Higher Rate (2 Mb/s) Physical (PHY) Layer," IEEE Computer Society, IEEE Standard 802.15.4t-2017, The Institute of Electrical and Electronics Engineers, Incorporation, New York, NY, USA, ISBN 378-0-1-5044-3933-6STDPD22524, Apr. 14, 2017, 25 pages.
"IEEE Standard for Low-Rate Wireless Networks," IEEE Computer Society, IEEE Standard 802.15.4-2015, The Institute of Electrical and Electronics Engineers, Incorporated, New York, NY, USA, ISBN 978-1-5044-0846-2 STDPD20893, Apr. 22, 2016, 708 pages.
"IEEE Standard for Wireless Access in Vehicular Environments (WAVE)—Identifier Allocations," IEEE Vehicle Technology Society, IEEE Standards Association 1609.12-2016, The Institute of Electrical and Electronics Engineers, Incorporated, New York, NY, USA, ISBN 978-1-5044-0765-6 3TD20840, Mar. 11, 2016, 39 pages.
"IEEE Standard for Wireless Access in Vehicular Environments (WAVE)—Multi-Channel Operation," IEEE Vehicular Technology Society, IEEE Standard 1609.4-2016, The Institute of Electrical and Electronics Engineers, Incorporation, New York, NY, USA, ISBN 978-1-5044-0761-83TD20838, Mar. 21, 2016, 205 pages.
"IEEE Standard for Wireless Access in Vehicular Environments (WAVE)—Over-the-Air Electronic Payment Data Exchange Protocol for Intelligent Transportation Systems (ITS)," IEEE Standards Association, IEEE Standard 1609.11-2010, The Institute of Electrical and Electronics Engineers, Incorporated, New York, NY, USA, ISBN 978-0-7381-6501-1STD97080, Jan. 9, 2011, 62 pages.
"IEEE Standard for Wireless Access in Vehicular Environments-Security Services for Applications and Management Messages," IEEE Vehicular Technology Society, IEEE Standard 1609.2-2016, The Institute of Electrical and Electronics Engineers, Incorporated, New York, NY, USA, ISBN 978-1-5044-0767-0 STD20841, Mar. 1, 2016, 884 pages.
"Information Technology—ASN.1 Encoding Rules: Specification of Packed Encoding Rules (PER), "International Telecommunication Union, ITU-T Telecommunication Standardization Sector of ITU X.691, Geneva, Switzerland, Aug. 2015, 74 pages.
"Information Technology—Open Systems Interconnection—Basic Reference Model: The Basic Model," International Standard, ISO/IEC 7498-1:1994 (E), Geneva, Switzerland, Nov. 15, 1994, 68 pages.
"Information Technology—Security Techniques—Evaluation Criteria for IT Security—Part 1: Introduction and General Model, "The International Organization for Standardization and the International Electrotechnical Commission Joint Technical Committee, ISO/IEC Standard 15408-1:2009 (E), 3rd Edition, Geneva, Switzerland, Dec. 15, 2009, 74 pages.
"Information Technology—Security Techniques—Evaluation Criteria for IT Security—Part 2: Security Functional Components,"The International Organization for Standardization and the International Electrotechnical Commission Joint Technical Committee, ISO/IEC Standard 15408-2:2008 (E), 3rd Edition, Geneva, Switzerland, Aug. 15, 2008, 240 pages.
"Information Technology—Telecommunications and Information Exchange between Systems—Near Field Communication—Interface and Protocol (NFCIP-1)," The International Organization for Standardization and the International Electrotechnical Commission, ISO/IEC Standard 18092:2013 Technical Corrigendum 1, Joint Technical Committee, Geneva, Switzerland, Jul. 15, 2015, 2pages.
"Information Technology—Telecommunications and Information Exchange between Systems—Near Field Communication—Interface and Protocol (NFCIP-1)," The International Organization for Standardization and The International Electrotechnical Commission Joint Technical Committee, ISO/IECStandard 18092:2013, Geneva, Switzerland, Mar. 15, 2013, 52 pages.
"Information Technology Security Techniques- Evaluation Criteria for IT Security—Part 3: Security Assurance Components,"The International Organization for Standardization and the International Electrotechnical Commission Joint Technical Committee, ISO/IEC Standard 15408-3:2008(E), 3rd Edition, Geneva, Switzerland, Aug. 15, 2008, 188 pages.
"Intelligent Transport Systems (ITS); Access Layer Specification for Intelligent Transport Systems Operating in the 5 GHZ Frequency Band," ETSI European Standard EN 302 663 (V1.2.1), European Telecommunications Standards Institute, Sophia Antipolis, France, Reference REN/ITS-0040028, Jul. 2013, 24 pages.
"Intelligent Transport Systems(ITS); Decentralized Congestion Control Mechanisms for Intelligent Transport Systems Operating in the 5 GHz Range; Access Layer Part," ETSI Technical Specification TS 102 687 (V1.1.1), European Telecommunications Standards Institute, Sophia Antipolis, France, Reference DTS/ITS-0040014, Jul. 2011, 45pages.
"Intelligent Transport Systems(ITS); Mitigation Techniques to Avoid Interference between European CEN Dedicated Short Range Communication (CEN DSRC) Equipment and Intelligent Transport Systems (ITS) Operating in the 5 GHZ Frequency Range," ETSI Technical Specification TS 102 792 (V1.2.1), European Telecommunications Standards Institute, Sophia Antipolis, France, Reference RTS/ITS-00438, Jun. 2015, 23 pages.
"Intelligent Transport Systems(ITS); Radio Communications Equipment Operating in the 5 855 MHz To 5 925 MHZ Frequency Band; Harmonized EN Covering the Essential Requirements of Article 3.2 of the R&TTE Directive," ETSI Harmonized European Standard EN 302 571(V1.2.1), European Telecommunications Standards Institute, Sophia Antipolis, France, Reference REN/ERM-TG37-009, Sep. 2013, 47 pages.
International Preliminary Report on Patentability for International Application No. PCT/US2018/046059, mailed Aug. 20, 2019, 39 pages.
International Preliminary Report on Patentability for International Application No. PCT/US2018/046062, mailed Feb. 20, 2020, 12 pages.
International Preliminary Report on Patentability for International Application No. PCT/US2018/046308, mailed Oct. 16, 2019, 57 pages.
International Search Report and Written Opinion for International Application No. PCT/US2018/046059, mailed Oct. 22, 2018, 24 pages.
International Search Report and Written Opinion for International Application No. PCT/US2018/046062, mailed Oct. 22, 2018, 13 pages.
International Search Report and Written Opinion for International Application No. PCT/US2018/046308, mailed Oct. 12, 2018, 14 pages.
Final Office Action for U.S. Appl. No. 15/880,686, dated Apr. 30, 2021, 19 pages.
Non-Final Office Action for U.S. Appl. No. 15/880,686, dated Jun. 25, 2020, 22 pages.
Non-Final Office Action for U.S. Appl. No. 15/880,686, dated Oct. 29, 2020, 16 pages.
Notice for Allowance for U.S. Appl. No. 15/880,686, dated Jul. 30, 2021, 7 pages.
Non-Final Office Action for U.S. Appl. No. 15/880,699, dated Aug. 8, 2019, 24 pages.
Notice for Allowance for U.S. Appl. No. 15/880,699, dated Jan. 14, 2020, 9 pages.
Non-Final Office Action for U.S. Appl. No. 16/101,152, mailed on Sep. 29, 2020, 21 pages.
Non-Final Office Action for U.S. Appl. No. 16/101,152, mailed on Aug. 9, 2021, 25 pages.
Final Office Action for U.S. Appl. No. 16/101,152, mailed on Feb. 2, 2021, 21 pages.
Notice of Allowance for U.S. Appl. No. 16/101,152, mailed on Jan. 19, 2022, 10 pages.

(56) References Cited

OTHER PUBLICATIONS

Non-Final Office Action for U.S. Appl. No. 15/880,663, mailed on Oct. 14, 2019, 44 pages.
Notice of Allowance for U.S. Appl. No. 15/880,663, mailed on Oct. 16, 2020, 15 pages.
Notice of Allowance for U.S. Appl. No. 15/880,663, mailed on Apr. 2, 2021, 16 pages.

* cited by examiner

TOP VIEW

SYSTEMS AND METHODS FOR PRESSURE INJURY MITIGATION

RELATED APPLICATIONS

The present application is a continuation of U.S. patent application Ser. No. 17/194,246, filed Mar. 6, 2021, titled "Systems and Methods for Pressure Injury Mitigation," which claims benefit of priority under 35 U.S.C. § 119 (e) from U.S. Patent Application No. 62/985,907 filed on Mar. 6, 2020, titled "Systems and Methods for Pressure Injury Mitigation," both of which are hereby incorporated by reference in their entirety.

The present application is related to U.S. patent application Ser. No. 15/880,663 filed Jan. 26, 2018, titled "Secure Systems Architecture for Integrated Motorized Mobile Systems," to U.S. patent application Ser. No. 15/880,686 filed Jan. 26, 2018, titled "Federated Sensor Array for Use with a Motorized Mobile System and Method of Use," to U.S. patent application Ser. No. 15/880,699 filed Jan. 26, 2018, titled "System and Methods for Sensor Integration in Support of Situational Awareness for a Motorized Mobile System," to U.S. patent application Ser. No. 16/101,152 filed Aug. 26, 2019, titled "Systems and Methods for Enhanced Autonomous Operations of a Motorized Mobile System," and to U.S. patent application Ser. No. 16/858,704 filed Apr. 26, 2020, titled "Systems and Methods to Upgrade a Motorized Mobile Chair to a Smart Motorized Mobile Chair," all of which are incorporated herein by reference in their entirety.

COPYRIGHT NOTICE

Contained herein is material that is subject to copyright protection. The copyright owner has no objection to the facsimile reproduction by anyone of the patent document or the patent disclosure, as it appears in the United States Patent and Trademark Office patent file or records, but otherwise reserves all rights to the copyright whatsoever. The following notice applies to the software, screenshots and data as described below and in the drawings hereto and All Rights Reserved.

FIELD

This disclosure relates generally to sensor systems for user health and presence monitoring.

BACKGROUND

Pressure injuries are localized damage to the skin and tissue, often over a bone or at the interface with a medical device, such as a wheelchair or hospital bed. Pressure injuries generally occur due to prolonged pressure and/or shear on an area of the skin. They can be extremely painful, limiting a patient's wellbeing and, in some cases, can cause open ulcers that are dangerous to a patient's overall health. Pressure injuries are also known as pressure ulcers, bedsores, decubitus ulcers, or pressure injurys. Pressure injuries can occur on any part of the body. However, it is common for wheelchair users to get pressure injuries on their buttock or legs and for patients confined to a bed to get pressure injuries on their back or the back of their head.

It is well understood that pressure injuries often result from prolonged time in a seat, a bed, or other support, but there are few good ways to predict whether a patient will get a pressure injury. Two different people under identical conditions do not necessarily have the same probability of developing a pressure injury. This is because pressure injuries are caused by a variety of intrinsic and extrinsic factors. Some of these factors, such as poor nutrition, use of steroids, and aging are demographic and lifestyle factors. Other factors, such as pressure, temperature, humidity, and friction/shear force on an area of the body may be assessed using one or more sensors. While there are many rules of thumb and best practices for pressure injury avoidance, the data is not currently available to develop an accurate predictive algorithm for pressure injury risk.

Wheelchair users are at a particularly high risk for pressure injury development. In an attempt to address this, there are a large variety of seat cushions currently available on the market. Many of these seat cushions claim to reduce the likelihood of developing pressure injuries. Current cushion technology can be divided into two basic approaches: (1) pressure distribution or (2) offloading.

Pressure distribution cushions are often referred to as immersion cushions. Immersion cushions are typically made from air bladders, water bladders, gel pads, soft foam, and other materials designed to equalize the pressure over the entire contact patch between the cushion and the user. These systems can be effective when sufficient pressure distribution is achieved. They have the downside of typically creating unstable surfaces, which can make it difficult for a user to feel secure in a position.

Offloading cushions are typically made of structural materials like high density foam or plaster and are shaped to match the contours of the user with specific areas removed to avoid loading pressure on bony parts of the body. These systems can be effective when the user is in the proper position and the contour properly matches the user. They have the potential to cause accelerated pressure injury development if not setup right, but offer the user extremely good stability.

Due to the limitations of pure offloading and pure immersion cushions, there is a wide variety of foam or hybrid cushions with both foam and select areas of immersion bladders that attempt to effectively distribute pressure while providing more positional stability to the user. These cushions may include an outer firm, contoured surface and reliefs around bony areas with air or gel pads.

Current solutions are designed to be set up correctly once with the expectation that they will work to reduce the risk of a pressure injury. What is needed is a better, data driven approach to pressure injury avoidance and treatment.

Aspects and applications presented here are described below in the drawings and detailed description. Unless specifically noted, it is intended that the words and phrases in the specification and the claims be given their plain and ordinary meaning to those of ordinary skill in the applicable arts. The inventors are aware that they can be their own lexicographers if desired. The inventors expressly elect, as their own lexicographers, to use only the plain and ordinary meaning of terms in the specification and claims unless they clearly state otherwise and expressly set forth the "special" definition of that term. Absent such clear statements of intent to apply a "special" definition, it is the inventors' intent and desire that the plain and ordinary meaning to the terms be applied to the interpretation of the specification and claims.

Further, the inventors are informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f) to define the systems, methods, processes, and/or apparatuses disclosed herein. To the contrary, if the provisions of 35 U.S.C. § 112(f) are sought to be invoked to define the embodiments, the claims will specifically and expressly state the exact phrases "means for" or "step for" and will also recite the word "function" (i.e., will state "means for performing the function of . . . "), without also reciting in such phrases any structure, material, or act in support of the function. Thus, even when the claims recite a "means for performing the function of . . . " or "step for performing the function of . . . ", if the claims also recite any structure, material, or acts in support of that means or step then it is the clear intention of the inventors not to invoke the provisions of 35 U.S.C. § 112(f). Moreover, even if the provisions of 35 U.S.C. § 112(f) are invoked to define the claimed embodiments, it is intended that the embodiments not be limited only to the specific structures, materials, or acts that are described in the embodiments, but in addition, include any and all structures, materials, or acts that perform the claimed function as described in alternative embodiments or forms, or that are well known present or later-developed equivalent structures, materials, or acts for performing the claimed function.

SUMMARY

In one aspect, a cushion has at least one fluid chamber and at least one cushion conduit to enable fluid to be added to or removed from the at least one fluid chamber of the cushion. A management system for the cushion has a pressure sensor to measure a pressure of fluid in the at least one fluid chamber of the cushion and to transmit a sensor report with the measured pressure, a tube having a first end connecting to the cushion conduit, a second end leading to the pressure sensor, and a valve to enable fluid to be added to or removed from the at least one fluid chamber of the cushion through the cushion conduit and a processor to receive the sensor report, determine a pressure value of the at least one fluid chamber of the cushion based on the measured pressure in the sensor report, and generate a status indicative of the pressure value of the fluid chamber of the cushion.

BRIEF DESCRIPTION OF THE DRAWINGS

A more complete understanding of the systems, methods, processes, and/or apparatuses disclosed herein may be derived by referring to the detailed description when considered in connection with the following illustrative figures. In the figures, like-reference numbers refer to like-elements or acts throughout the figures.

Elements and acts in the figures are illustrated for simplicity and have not necessarily been rendered according to any particular sequence or embodiment.

DETAILED DESCRIPTION

In the following description, and for the purposes of explanation, numerous specific details, process durations, and/or specific formula values are set forth in order to provide a thorough understanding of the various aspects of exemplary embodiments. However, it will be understood by those skilled in the relevant arts that the apparatus, systems, and methods herein may be practiced without all of these specific details, process durations, and/or specific formula values. Other embodiments may be utilized and structural and functional changes may be made without departing from the scope of the apparatus, systems, and methods herein. It should be noted that there are different and alternative configurations, devices, and technologies to which the disclosed embodiments may be applied.

In the following examples of the illustrated embodiments, references are made to the accompanying drawings which form a part hereof, and in which is shown by way of illustration various embodiments in which the systems, methods, processes, and/or apparatuses disclosed herein may be practiced. It is to be understood that other embodiments may be utilized and structural and functional changes may be made without departing from the scope of this disclosure.

Systems and methods are disclosed to assist users in avoiding and managing pressure injuries with a smart cushion. The systems and methods disclosed may be used in combination with a wide range of devices, including on beds, manual and/or powered wheelchairs, vehicular seating systems, and/or aerospace seating systems. A non-limiting exemplary embodiment of use in combination with a wheelchair is used throughout for illustrative purposes and clarity.

Smart Cushion

Figure 1:
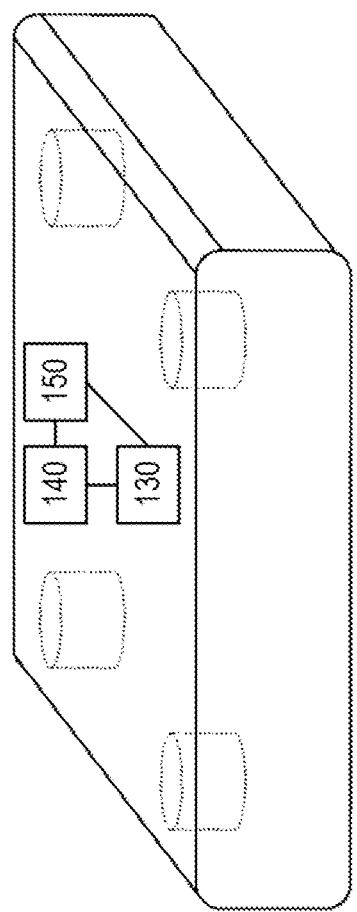
FIG. 1 depicts an embodiment of a smart cushion.

FIG. 1 depicts an exemplary embodiment of a smart cushion 110. A smart cushion is a cushion that includes, connects to, or otherwise receives data via wired or wireless communications from one or more sensors 120. Examples of sensors 120 include one or more force and/or pressure sensors capable of measuring weight and/or weight distribution, pressure, and/or force (e.g. on the cushion), one or more sensors capable of measuring temperature and/or humidity, one or more moisture sensors, and/or a smart fabric capable of changing resistance, capacitance, or conductivity in response to force, shear force, stretch, wetness, and/or friction. A sensor 120 may additionally or alternatively be or include one or more sensors to measure user/occupant presence, user/occupant position, distance to the user/occupant (e.g. to a body part of the user), user movement, user heart rate, user temperature, user respiratory rate, user blood oxygen content, and/or user blood pressure.

In an example, a smart cushion 110 uses for the one or more sensors 120 one or more patches or pieces of pressure-sensitive conductive sheets (e.g. velostat or linqstat) to sense user weight distribution (e.g. on, across, or over the smart cushion), one or more sensors to measure temperature, humidity, and/or moisture on or in connection with the smart cushion and/or wheelchair, bed, or other device, and/or one or more variable resistance fabric sensors (e.g. EEonTex) to approximate user friction, force, and/or shear force on or in connection with the smart cushion and/or wheelchair, bed, or other device. Additionally, the smart cushion 110 may include for the one or more sensors 120 a flex sensor or presence sensor, such as a capacitance or distance sensor that confirms user presence in the seat to help track time-inSeatt. Additionally, the smart cushion 110 may include one or more processors 130 that communicate with the one or more sensors 120 to monitor sensor reports (one or more communications from one or more sensors that include sensor data) and communicate with other devices. The smart cushion 110 may additionally include an optional power supply 140, such as a battery or supercapacitor, to provide power to the one or more processors and one or more sensors 120. Alternately, the smart cushion 110 may draw power from a power supply of another device, such as a bed, wheelchair, gurney, or seat.

Figure 2:
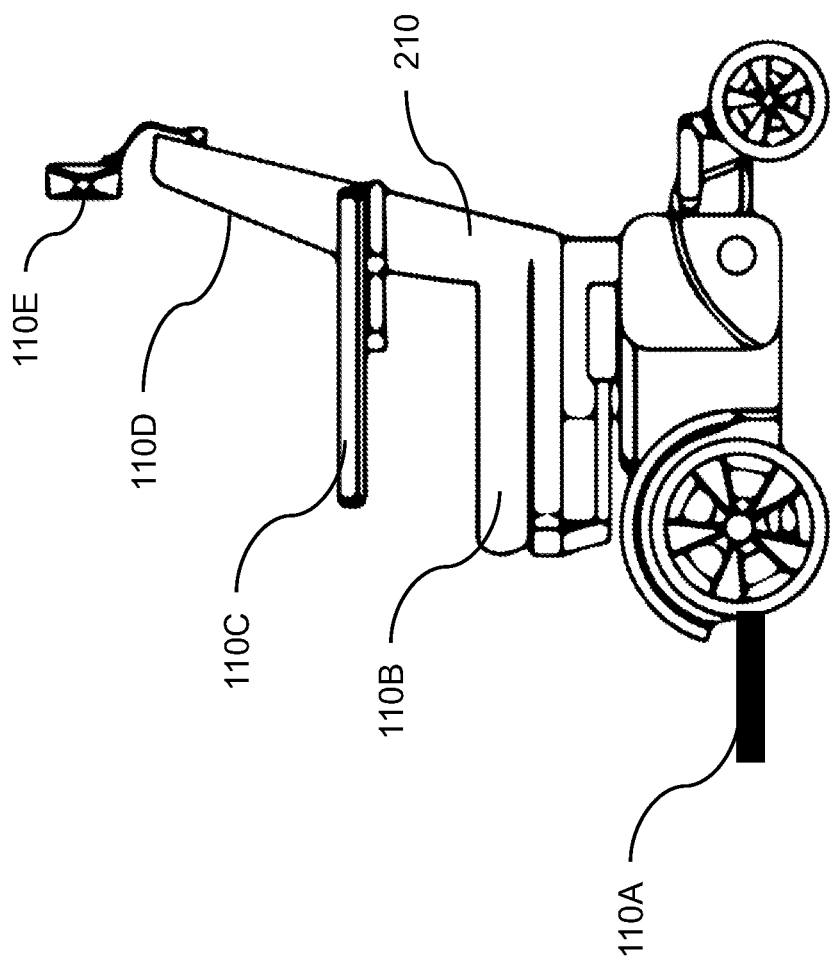
FIG. 2 depicts one or more smart cushions attached to a wheelchair seating system.

FIG. 2 depicts one or more smart cushions (110A-E) attached to a wheelchair 210, such as to a support structure of a wheelchair seating system and/or another wheelchair support structure for the one or more smart cushions. As depicted in FIG. 2, one or more smart cushions 110A-E may be used at a time and may operate independently or in a coordinated manner. As an example, a smart cushion 110A may be used at the foot or leg rest area/location of the chair, another smart cushion 110B may be used at the buttocks area/location of the chair, another smart cushion 110C may be used at the arm support or arm trough area/location of the chair, another smart cushion 110D may be used at the back support area/location of the chair, and another smart cushion 110E may be used at the head support area/location of the chair. Sensors and smart cushions may additionally be used for other parts/areas/locations of a seating system not depicted, such as side or thigh support areas/locations in some embodiments.

Each smart cushion may use the same or a different combination of one or more sensors to match the requirements of the cushion area/location. As an example, a smart cushion 110B for the buttocks location may include a wetness sensor to sense incontinence and one or more pressure sensors, whereas a smart cushion 110E for the head support area/location may not require a wetness sensor. Additionally, the different smart cushions may be made of different materials and constructed of different types of sensors to fit the needs of the cushion area/location and the user.

The smart cushion sensors 120 may be wired or wirelessly communicatively coupled to one or more processors 130 and/or one or more communication devices 150 (e.g. Bluetooth, Wi-Fi, or cellular devices or communication busses) such that measurements/data transmitted from one or more sensors are received at and processed by the processor(s) and/or the communication devices and/or transmitted from the processor(s) and/or communication devices (e.g. via Bluetooth, WiFi, or cellular transceivers or communication busses of the smart cushion) to another device. The processor 130 and/or communication devices 150 may be integrated into the smart cushion or may be attached to one or more ports, connections, or components of the smart cushion separately as a monitoring and management system in some embodiments.

Figure 3:
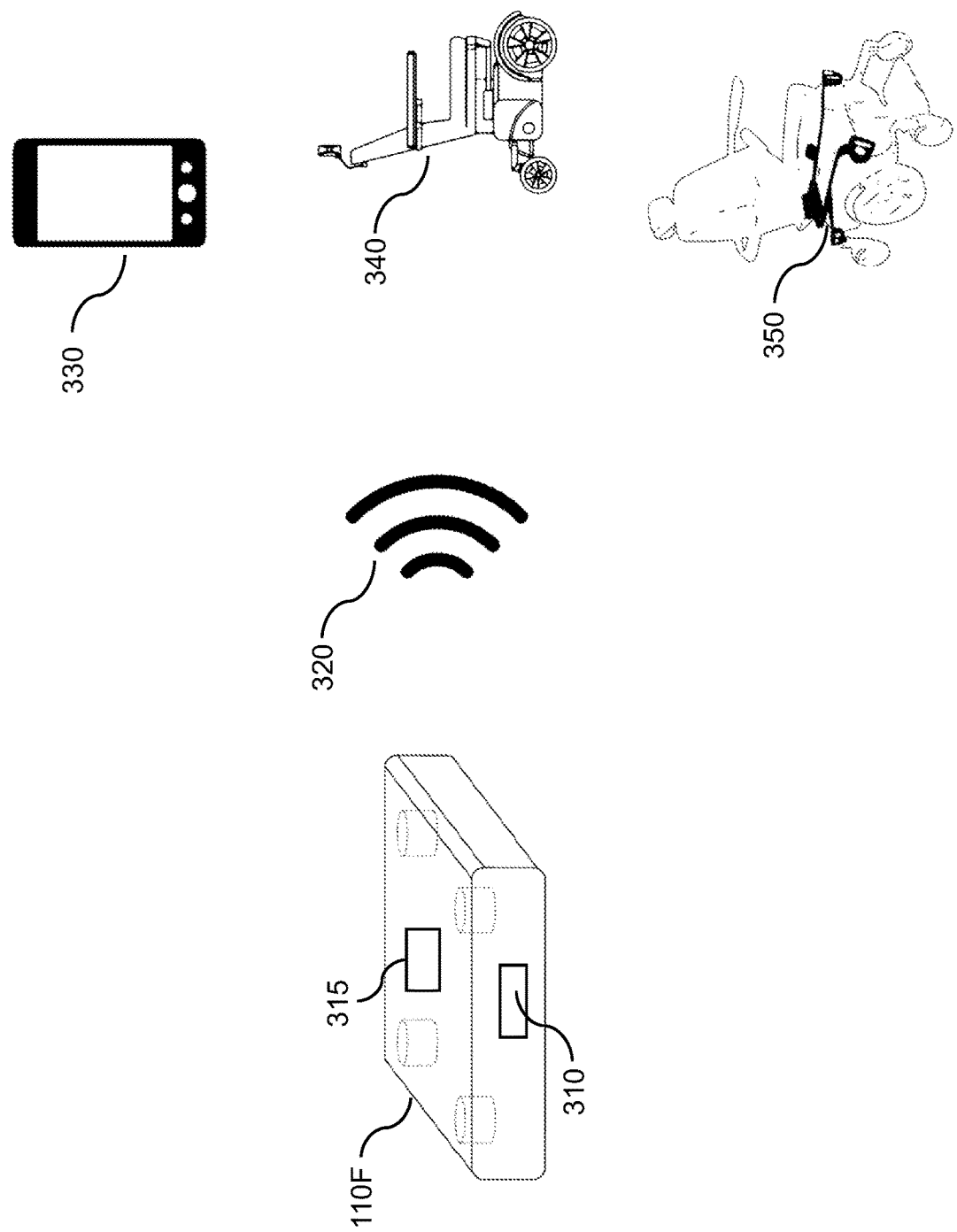
FIG. 3 depicts a smart cushion with one or more processors configured to communicate with one or more other devices.

FIG. 3 depicts a smart cushion 110F with one or more processors 310 and one or more transmitters/transceivers 315 configured to transmit and/or receive one or more communications 320 with one or more other devices, e.g. via Bluetooth (classic or low energy), WiFi, or cellular communications. Communications may include data, commands, and/or control signals transmitted and/or received via one or more wired or wireless devices/means. The data, commands, and/or control signals may be comprised of digital and/or analog signals. In an embodiment, a processor 310 of the smart cushion 110F communicates wirelessly via a transceiver 315 with a computer, tablet, or other smart device 330. The wireless communications may occur by one or more processors, one or more communication processors (which may be separate from or integrated with the one or more processors), and one or more transceivers of the smart cushion using wireless communication methods and protocols including, but not limited to, cellular communications, 802.11 communications, RFID, Wi-Fi communications, 802.15 communications, Bluetooth communications, Bluetooth Low Energy communications, 802.16 communications, WiMAX communications, near field communications, Zigbee communications, and 18092 communications. In one example, the smart cushion processor 310 transmits one or more communications containing data and/or commands to a transceiver 315 of the smart cushion, and the transceiver transmits one or more wired or wireless communications with the data and/or commands to another device. Similarly, the transceiver 315 may receive one or more wired or wireless communications with data and/or commands from another device (e.g. the smart device 330) and transmit one or more communications to the processor with the data and/or commands.

The processor 310 of the smart cushion optionally performs one or more calculations on the data of the one or more sensor reports or otherwise processes the data in the sensor reports. Additionally or alternatively, the processor 310 of the smart cushion may make one or more decisions and/or take one or more actions based on the data or commands in the one or more sensor reports.

In another embodiment, one or more processors 310 of a smart cushion 110F are communicatively coupled, via a wireless or wired connection, to a medical device 340 such as a bed, wheelchair, gurney, or seat. The smart cushion 110F may draw power from the medical device 340 in some examples. Sensor data from one or more sensors embedded in, or attached to, the smart cushion 110F is then processed by the processor 310 of the smart cushion, and the processed data, original data, and/or commands are transmitted by the processor to the medical device 340 in one or more communications, e.g. via one or more transmitters/transceivers 315 of the smart cushion. In an example, one or more processors of the medical device 340 may then take one or more actions based on one or more communications received from the smart cushion 110F. Additionally or alternatively, the one or more processors 310 of the smart cushion may take one or more actions based on the sensor data and/or the one or more communications received from the medical device 340, including when the one or more communications from the medical device include data, instructions, commands, and/or control signals. The one or more processors 310 of the smart cushion 110F may receive the one or more communications from the medical device 340 via the one or more transceivers 315.

The processor 310 optionally communicates to the one or more processors of the medical device 340 through one or more transceivers of the medical device at least one of the raw data in the sensor reports, outputs/results of one or more calculations or other processing performed on the data of the sensor reports, one or more decisions made by the processor based on processing the data in the sensor reports, and/or one or more commands generated by the processor, including based on one or more decisions made by the processor and/or data from the sensor reports. In some embodiments one or more processors of the medical device 340 may send (via one or more transceivers of the accessory) data, one or more pieces of data, or one or more control signals to the processor 310 of the smart cushion 110F, which causes changes by the processor in the calculations, processing, decision making, or other action of the smart cushion 110. Sensor reports may include, for example, fluid pressure sensor reports, fluid volume sensor reports, wetness sensor reports, humidity sensor reports, temperature sensor reports, non-contact sensor reports, image sensor reports, and user sensor reports.

In another example of the system depicted in FIG. 3, one or more processors 310 of a smart cushion 110F communicate, via a wired or wireless connection 320, with an accessory 350 to a power wheelchair, e.g. via one or more transceivers 315 of the smart cushion and one or more transceivers of the accessory to the power wheelchair. In this non-limiting example, the processor 310 of the smart cushion accepts one or more sensor reports (i.e. a communication with or identifying data sensed by the sensor and/or with one or more commands) from one or more sensors of the smart cushion (e.g. 120 FIG. 1). The one or more sensors may be embedded in or attached to the smart cushion 110. The sensor data is then processed by the processor 310 of the smart cushion, and the processed data, original data, and/or commands are transmitted by the processor to the accessory 350 in one or more communications, e.g. via one or more transmitters/transceivers 315 of the smart cushion. In an example, one or more processors of the accessory 350 may then take one or more actions based on one or more communications received from the smart cushion 110F. Additionally or alternatively, the one or more processors 310 of the smart cushion may take one or more actions based on the sensor data and/or the one or more communications received from the accessory 350, including when the one or more communications from the accessory include data, instructions, commands, and/or control signals. The one or more processors 310 of the smart cushion 110F may receive the one or more communications from the accessory 350 via the one or more transceivers 315.

The processor 310 optionally communicates to the one or more processors of the accessory 350 to the power wheelchair through one or more transceivers of the power wheelchair at least one of the raw data in the sensor reports, outputs/results of one or more calculations or other processing performed on the data of the sensor reports, one or more decisions made by the processor based on processing the data in the sensor reports, and/or one or more commands generated by the processor, including based on one or more decisions made by the processor and/or data from the sensor reports. In some embodiments one or more processors of the accessory 350 to the power wheelchair may send (via one or more transceivers of the accessory) data, one or more pieces of data, or one or more control signals to the processor 310 of the smart cushion 110F, which causes changes by the processor in the calculations, processing, decision making, or other action of the smart cushion 110.

Immersion Cushions

Figure 4:
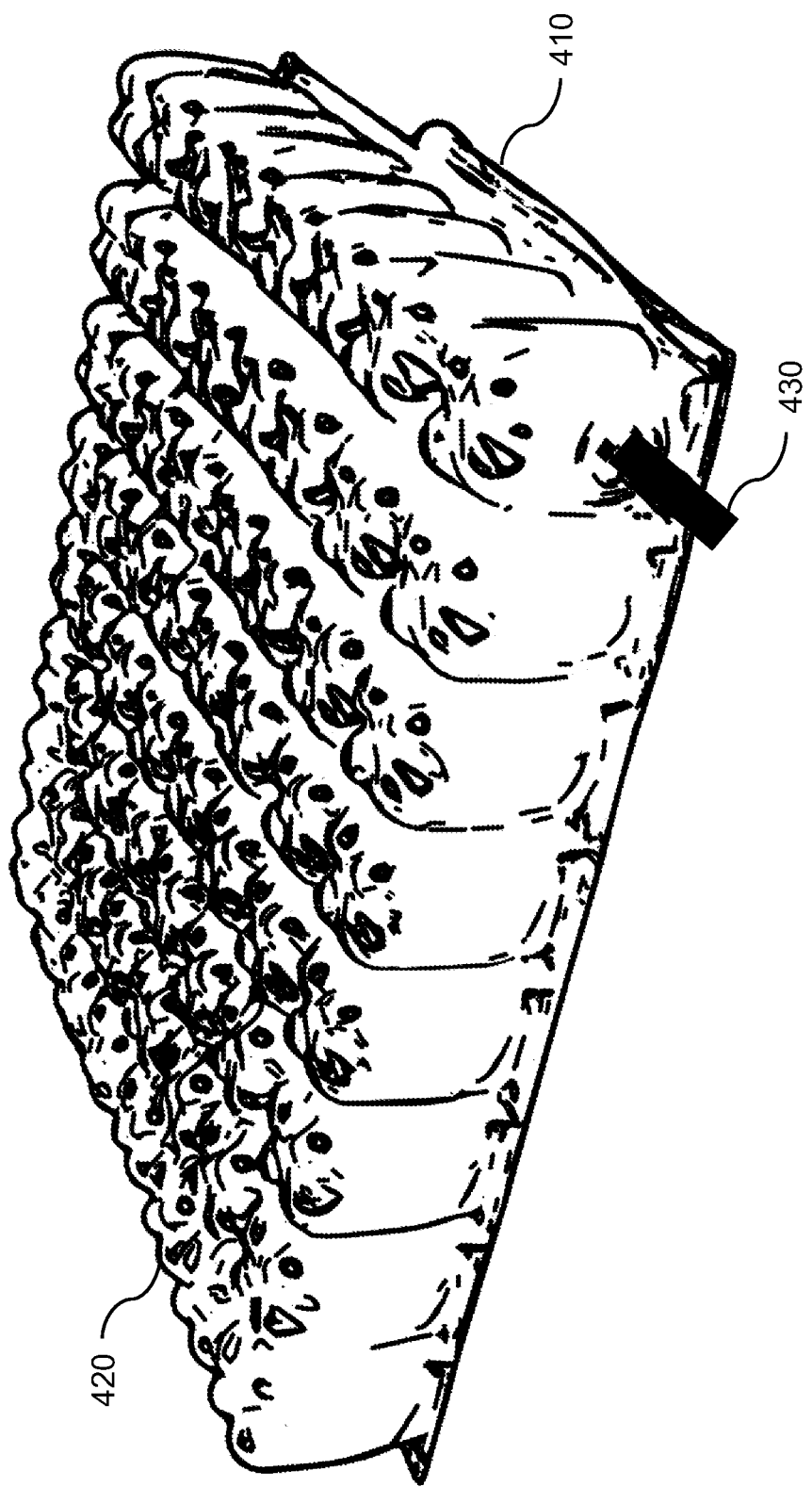
FIG. 4 depicts an embodiment of an immersion cushion.

FIG. 4 depicts an embodiment of a cushion 410, such as an immersion cushion. An immersion cushion is and consists of one or more flexible, fluid filled chambers used as a pad or cushion where the one or more chambers may be made from a material capable of retaining the fluid, such as an elastomer, rubber, a sealed fabric, or plastic. A chamber has an outer wall of the flexible material surrounding a void or cavity that holds fluid. Adjacent chambers may be separated by a wall or walls between them such that fluid is held in the cavity of each chamber without fluid flowing to an adjacent chamber. Alternately, two or more adjacent chambers may be connected by a valve, port, conduit, or duct or a hole/aperture in a wall, walls, or other structure between the adjacent chambers (e.g. when a wall or structure between two adjacent chambers is a partial wall or structure that does not completely separate fluid holding cavities of the adjacent chambers). In one example, a conduit, duct, or port includes a valve. The fluid in the chambers is typically air, gel, or a non-compressible fluid, such as water. Immersion cushions are intended to allow a user to become immersed into the cushion so that it envelopes part of the user or part of a body part of the user (e.g. the buttock or a portion of the buttock). Immersion depth is the depth to which a body or a part of the body penetrates into a seat cushion from an uppermost plane of the cushion. Envelopment is the ability of a cushion to conform to or mold around the shape of the body or a part of the body. Immersion cushions aim to redistribute pressure over a large area of contact with the user or a part of a body part of the user (e.g. the person's gluteal surface for a bottom cushion 110B FIG. 2).

In the exemplary embodiment of a cushion 410 of FIG. 4, there are one or more fluid chambers 420 to hold fluid and one or more conduits, ducts, or ports for adding or removing fluid to or from the fluid chambers. In some instances, a conduit, duct, or port includes a fill valve 430 for controlling adding or removing fluid to or from the fluid chambers. Immersion cushions are often used as a means to fight pressure injuries. Typically, an immersion cushion is placed between the user or a body part of the user and a support surface, such as a platform, seating assembly component, or other frame. In some embodiments, the fluid chamber 420 of an immersion cushion may be divided into multiple fluid chambers where these fluid chambers have valves, conduits, or ducts between them or a hole/aperture in a wall, walls, or other structure between them to add or remove fluid between chambers or are connected in such a way that the fluid flow between chambers (e.g. adjacent chambers) can be controlled/regulated. In some embodiments, each chamber 420 may have its own fill valve 430. In other embodiments, a group of two or more chambers 420 have one fill valve for the group of chambers, and each chamber in the group is connected to at least one other chamber in the group (e.g. an adjacent chamber) by another valve, conduit, or duct or a hole/aperture in a wall, walls, or other structure between two adjacent chambers (e.g. when a wall or structure between two adjacent chambers is a partial wall or structure that does not completely separate fluid holding cavities of the adjacent chambers). Additionally or alternatively, an immersion cushion may be embedded in or used in combination with other cushion construction techniques, including foam or other hybrid constructions. In all of these cases, the systems and methods disclosed may be applied to multiple chambers, multiple valves, conduits, ducts, and/or holes/apertures in walls or other structures between adjacent chambers 420 or in hybrid constructions. As used herein, the term fluid includes a liquid and a gas, such as air. A liquid includes a gel herein.

Pressure injuries can be a significant health concern for wheelchair users and those constrained to a bed or chair for long periods of time. Pressure injuries have a number of causes. Research demonstrates one of the main causes of pressure injuries is improper pressure distribution. In addition, it is widely believed that a "properly deflated" immersion cushion can be one of the best tools available to fight pressure injuries.

In one example, a properly deflated immersion cushion includes chambers that are selectively filled on an individual or group/section/portion basis with fluid between 10%-100% of the fluid volume capacity of the chamber. For example, all chambers 420 may be filled at 40% of the fluid volume capacity of the chambers for one user and 60% of the fluid volume capacity of the chambers for another user. In another example, chambers 420 in a first third of the chambers (e.g. first end third) of an immersion cushion are filled at 55% of the fluid volume capacity of the chambers, chambers in a second third of the chambers (e.g. middle third) are filled at 75-80% of the fluid volume capacity of the chambers, and chambers in the final third of the chambers (e.g. second end third) are filled at 40% of the fluid volume capacity of the chambers. In this example, selectively filling one or more sections or portions of chambers of the immersion cushion on an individual or section basis at various selected fluid volume capacities enable the immersion cushion to more fully mold around the user's body part.

In one example, each section or portion of the chambers 420 that are selectively filled at various selected fluid volume capacities have a separate valve 430 for filling or removing fluid from the section or portion of chambers. In one aspect of this example, each chamber 420 in the section, group, or portion is connected by a conduit, duct, or wall aperture (e.g. a hole or aperture in a wall, walls, or other structure between two adjoining chambers, including an incomplete wall between two chambers) to at least one other chamber in the section, group, or portion so that fluid may be passed to each chamber, including between a chamber and an adjacent chamber. In another aspect of this example, each chamber 420 of each section/group/portion of the chambers that are selectively filled at various selected fluid volume capacities has a separate valve 430 for filling or removing fluid from the chamber. In another aspect of this example, each section of chambers 420 has a single main fill valve through which fluid is filled or removed from the section of chambers, and each of the chambers in the section or portion of the chambers that are selectively filled at various selected fluid volume capacities are connected to each other by a valve or a connecting tube, conduit, duct, wall aperture, or other fluid conveying mechanism but are not connected to chambers of any other section or portion by a valve or connecting tube, conduit, duct, wall aperture, or other fluid conveying mechanism. Proper internal pressure is critical for an immersion cushion to be effective.

In another aspect of this example, a processor of the cushion or an auxiliary device of the cushion determines the current pressure and/or fluid volume of one or more chambers 420 or one or more sections or groups of chambers (e.g. based on sensor reports from one or more sensors or monitoring and recording the amount of fluid filled in or removed from the chambers) and, in response, adds additional fluid to the chambers, removes fluid from the chambers, or maintains the level of fluid in the chambers, for example by instructing a pumping device to add fluid (e.g. by opening a valve while causing a pump to operate), remove fluid (e.g. by opening a valve while not causing a pump to operate or opening the valve and causing the pump to operate in a reverse operation to remove fluid), or not add or remove fluid (e.g. by closing a valve and causing the pump to not operate) to result, achieve, or maintain a selected pressure or fluid volume for one or more of the chambers or sections or groups of chambers.

In yet another example, a properly deflated immersion cushion includes chambers that are selectively filled on an individual or group/section basis with selected pressure value or between 10%-100% of the maximum pressure value of the chamber. For example, all chambers 420 may be filled at 40% of the maximum pressure value of the chambers for one user and 80% of the maximum pressure value of the chambers for another user. In another example, all chambers 420 may be filled at a first selected pressure value for one user and a second selected pressure value for another user. In another example, chambers 420 in a first third of the chambers (e.g. first end third) of an immersion cushion are filled at a first selected pressure value, chambers in a second third of the chambers (e.g. middle third) are filled at a second selected pressure value, and chambers in the final third of the chambers (e.g. second end third) are filled at a third selected pressure value. In this example, selectively filling one or more sections or portions of chambers of the immersion cushion on an individual or section basis at various selected fluid volume capacities enable the immersion cushion to more fully mold around the user's body part. In one aspect of this example, each section, group, or portion of the chambers 420 that are selectively filled at various selected pressure values have a separate valve 430 for filling or removing fluid from the section, group, or portion of chambers and each chamber in the section, group, or portion of chambers is connected to at least one other chamber in the group (e.g. an adjacent chamber) by a valve, tube, conduit, or duct or a hole/aperture in a wall, walls, or other structure between two adjacent chambers (e.g. when a wall or structure between two adjacent chambers is a partial wall or structure that does not completely separate fluid holding cavities of the adjacent chambers) so that fluid may be passed to each chamber, including between a chamber and an adjacent chamber.

In another aspect of this example, each chamber 420 of each section or portion of the chambers that are selectively filled at various selected pressure values or fluid volume capacities has a separate valve 430 for filling or removing fluid from the chamber. In another aspect of this example, each section of chambers 420 has a single main fill valve through which fluid is filled or removed from the section of chambers and each of the chambers in the section or portion of the chambers that are selectively filled at various selected pressure values or fluid volume capacities are connected to each other by a valve or a connecting tube, conduit, or duct or a hole/aperture in a wall, walls, or other structure between two adjacent chambers or fluid conveying mechanism but are not connected to chambers of any other section or portion by a valve or connecting tube, conduit, or duct or a hole/aperture in a wall, walls, or other structure between two adjacent chambers or other fluid conveying mechanism. Proper internal pressure is important for an immersion cushion to be effective.

In another aspect of this example, a processor of the cushion or an auxiliary device of the cushion determines the current pressure and/or fluid volume of one or more chambers 420 or sections or portions of chambers (e.g. based on sensor reports from one or more sensors for monitoring and recording the amount of fluid filled in or removed from the chambers) and, in response, adds additional fluid to the chambers, removes fluid from the chambers, or maintains the level of fluid in the chambers, for example by instructing a pumping device to add or remove fluid, to result, achieve, or maintain a selected pressure or fluid volume for one or more of the chambers or sections or groups of chambers.

Figure 5:
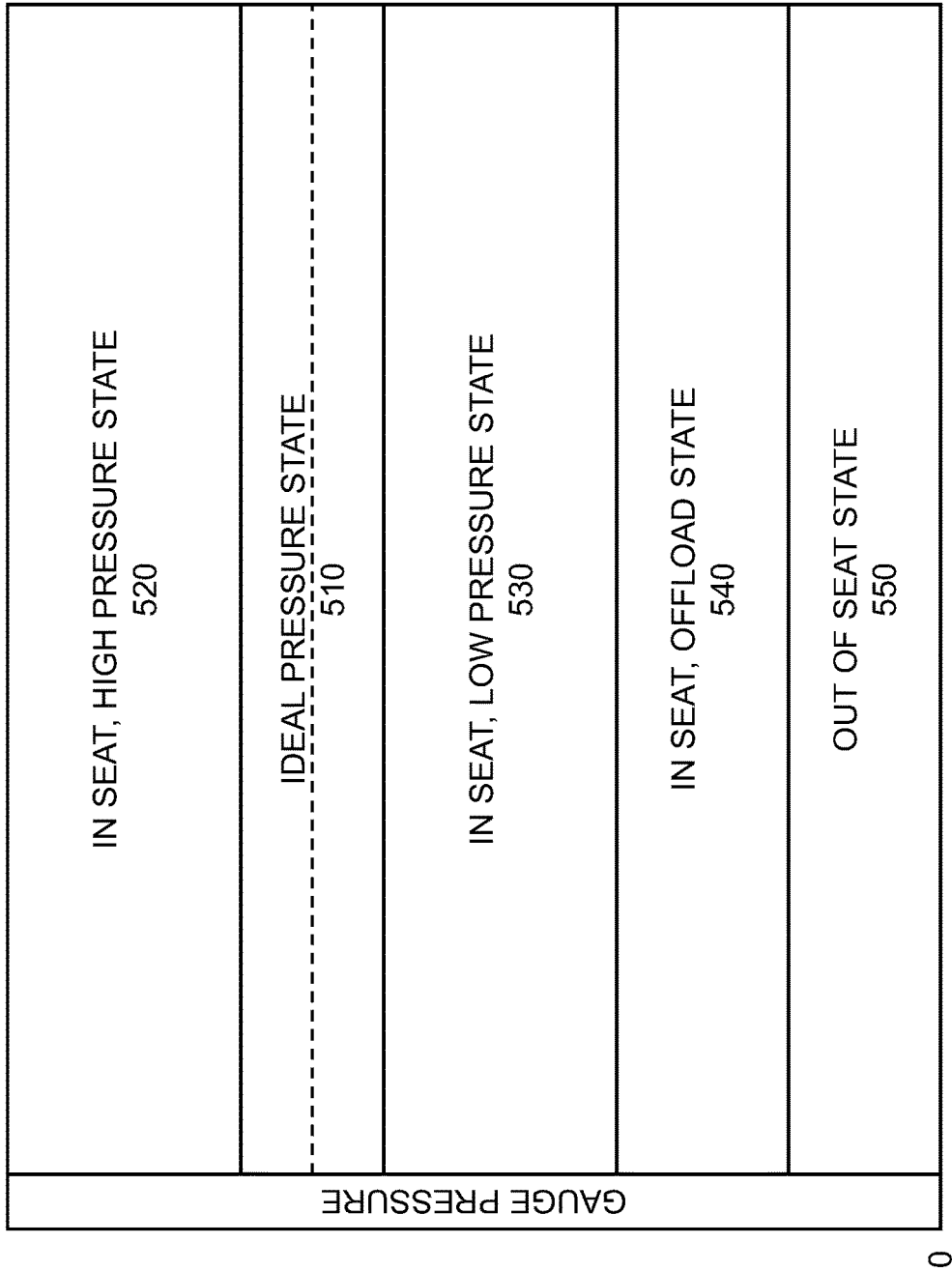
FIG. 5 depicts pressure behavior of an immersion cushion during use.

FIG. 5 depicts a pressure behavior of a cushion, such as an immersion cushion, during use. In the example of a seat cushion, there are three primary sitting states for a user: (1) in seat, (2) in seat but offloading, and (3) out of seat. Each of these user states can be determined by a smart cushion where the user state is calculated by a processor of the smart cushion from one or more sensor reports received from one or more sensors of the smart cushion. Pressure injuries result from constant pressure that impairs blood flow to soft tissue for an extended period. As previously stated, there is an ideal pressure value or zone state 510 in order to assist with healing and avoidance of pressure injuries. Pressures higher than the ideal pressure value or zone state (e.g. high pressure state) 520 and lower than the ideal pressure value or zone state (e.g. low pressure state) 530 while the user is seated can both lead to slower healing and/or higher risk of developing a pressure injury. Offloading is the practice of manually reducing the pressure on an area of a body by moving the body or using a mechanical seating assembly to tilt and/or recline the body in a way that relieves pressure from an area of the body (e.g. the buttock in a seat). As an example, it is recommended that wheelchair users offload their buttocks regularly in order to allow blood flow and avoid pressure injury development. For offloading to be successful, the external pressure on the skin should be at least less than the arterial capillary pressure of the body (32 mm Hg) to allow blood inflow and ideally less than the venous capillary closing pressure of the body (8-12 mm Hg) to allow the return of flow of blood through the skin. Based on this, an effective offloading pressure value or zone state 540 can be identified and defined. At a certain point, the pressure of the user in the seat is below offloading pressure state 540, and the user can be considered out of the seat state 550. Each of the states (510 thru 550) may be determined by one or more calculations of a processor of the smart cushion based on one or more sensor reports received from one or more sensors of the smart cushion 110 and/or recording fluid volume flow and/or removal from one or more chambers 420 or one or more sections or groups of chambers of the smart seat cushion.

Exemplary Management System

Figure 6:
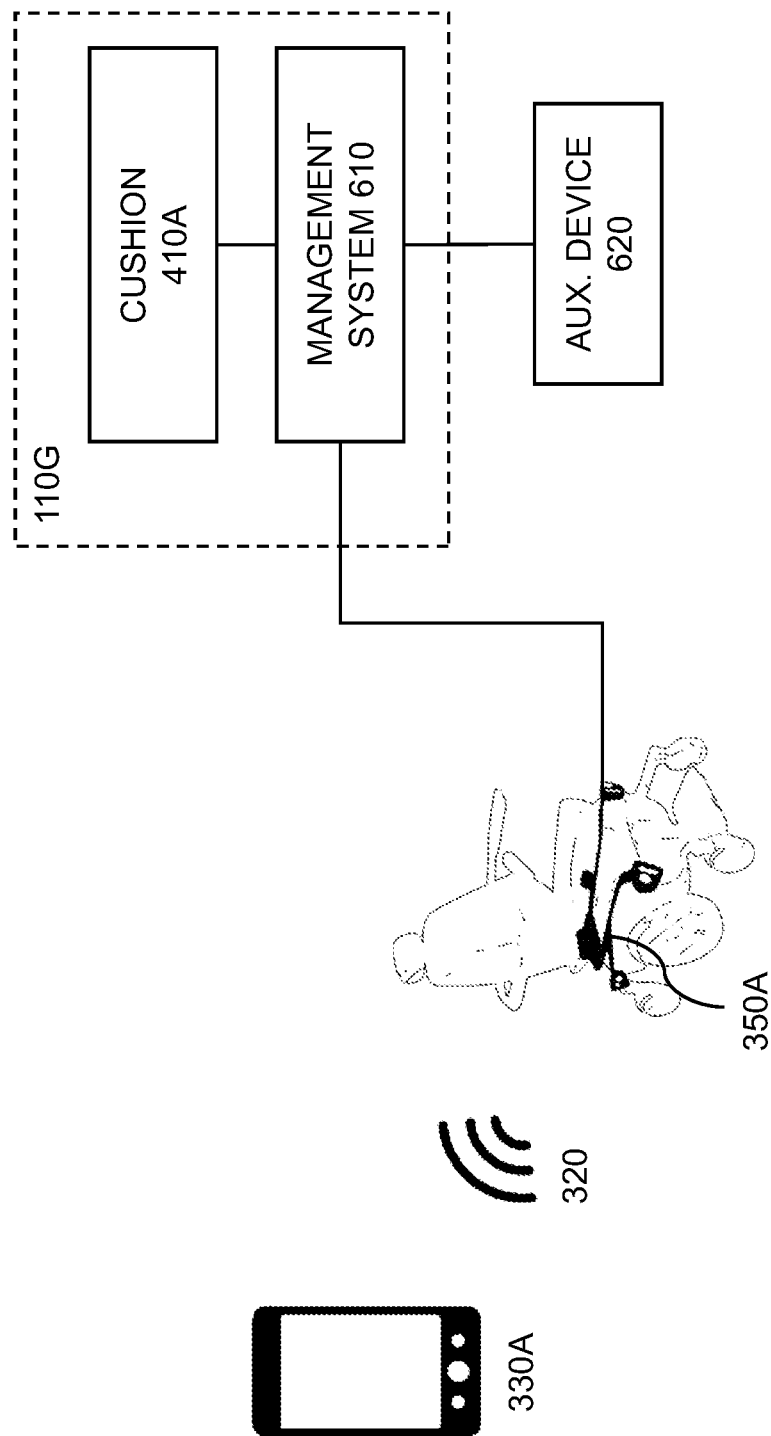
FIG. 6 depicts an overview of a management system.

FIG. 6 depicts an overview of an exemplary embodiment of a smart cushion 110G consisting of a fluid-filled cushion 410A, such as an immersion cushion, and a management system 610 for the cushion. In this embodiment, the management system 610 determines the current pressure and/or fluid volume of one or more chambers or sections or groups of chambers (e.g. based on one or more sensor reports from one or more sensors and/or monitoring and recording the amount of fluid filled in or removed from the chambers) and includes one or more processors which determines the current state (e.g. states 510 thru 550) of the cushion and/or user by one or more calculations of a processor based on one or more sensor reports received from one or more sensors of the smart cushion 110G. The one or more sensors in this embodiment may be added to the cushion 410A (e.g. after its manufacture) or may be included in the cushion 410A directly (e.g. at manufacture) and communicate with the management system 610 via one or more wired and/or wireless connections. Additionally, one or more additional sensors and/or other auxiliary devices may be added to the smart cushion 110G and connected to the management system 610 of the smart cushion 110G and transmit sensor reports, data, commands, and/or control instructions to the processor of the management system and/or receive data, commands, and/or control instructions from the processor of the management system. A non-limiting example of an auxiliary device 620 that extends the capabilities of the smart cushion 110G is a wetness sensor that can be placed on the cushion 410A to detect incontinence.

In the example of FIG. 6, one or more processors of the management system 610 communicate to the one or more processors of an accessory to a power wheelchair 350A through one or more transceivers at least one of the raw data in sensor reports, outputs/results of one or more calculations or other processing performed on the data of the sensor reports, one or more decisions made by the processor based on processing the data in the sensor reports, and/or one or more commands generated by the processor including based on one or more decisions made by the processor and/or data from the sensor reports. In some embodiments one or more processors of the accessory to the power wheelchair 350A may send (via one or more transceivers of the accessory) data, one or more pieces of data, or one or more control signals to the processor of the management system 610, which causes changes by the processor of the management system in the calculations, processing, decision making, or other action of the smart cushion 110G and/or a connected auxiliary device 620.

The accessory to the power wheelchair 350A may send wireless communications 320 (via one or more transceivers of the accessory) with data, one or more pieces of data, and/or one or more control signals to a smart phone, tablet, computer, server, or other device 330A. In an example, the accessory to the power wheelchair 350A my communicate with an application on a smartphone via Bluetooth Low Energy (BLE). The communication may contain one or more pieces of data, such as a user state (e.g. the person is in the seat and offloading) determined by one or more calculations of a processor of the management system 610. Additionally or alternatively, the communication may contain a timestamp, raw data from a sensor, or a control signal that causes the application on the smartphone to notify the user of an event (e.g. that they have successfully offloaded) or an action that they need to take (e.g. the user should add fluid to the cushion).

In an alternative example, the management system 610 of the smart cushion 110G may directly communicate using a wired or wireless communication with the smart phone, tablet, computer, server, or other device 330A such that the accessory to a power wheelchair 350A is not necessary.

Figure 7:
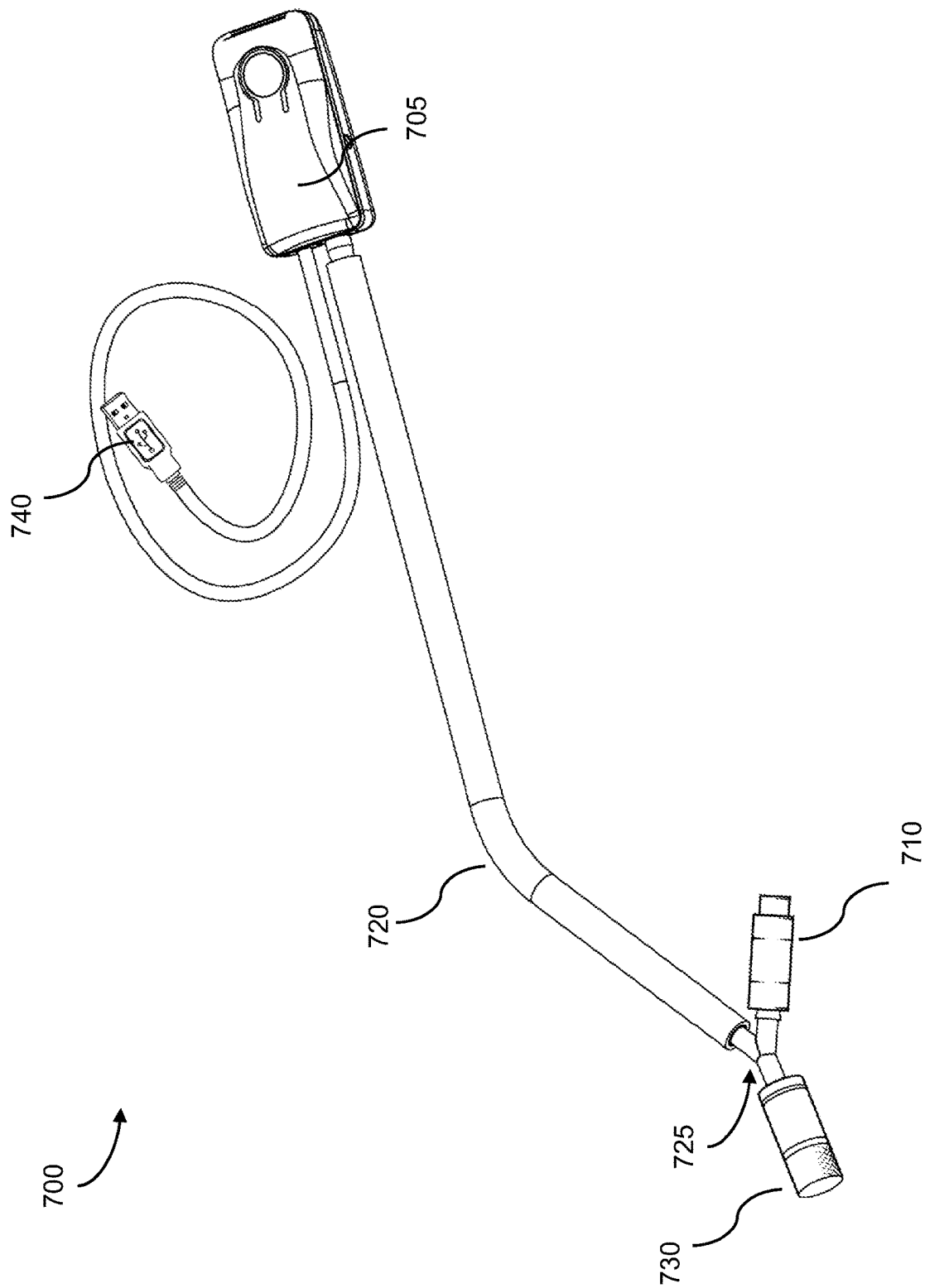
FIG. 7 depicts an exemplary embodiment of a management system for a cushion.

FIG. 7 depicts an exemplary embodiment of a non-integrated cushion management system and associated fluid connections 700 that is not integrated with a cushion and that can be added to a cushion after its manufacture to measure and/or control fluid pressure and/or volume of fluid in the fluid chambers of the cushion. The management system 705 connects to a fluid fill connection or fill valve of the cushion 410A (e.g. inflation/deflation connection or port of the cushion) with a connection or coupling 710 through a fluid passageway or tube 720. Fluid can be added to and/or removed from the cushion manually via a physical inflation/deflation (fill/remove) valve or port 730 of the fluid passageway or tube 720 (e.g. by connecting a manual or electric pump to the inflation/deflation valve or port, opening the inflation/deflation valve or port, and activating the pump to add fluid the inflation/deflation valve or port or by opening the inflation/deflation valve or port with no pump connected to the inflation/deflation valve or port to remove fluid by enabling fluid to escape to atmosphere or the environment) or automatically and electronically by the management system 705. The management system 705 is connected to the connection coupling 710 and the inflation/deflation valve or port 730 by the fluid passageway or tube 720. In one example, the fluid passageway or tube 720 is an inlet/outlet tube for inlet and outlet of fluid to and from the fluid chambers. In one example, the fluid passageway or tube 720 has or is connected to a Y-shaped split or a Y-shaped connection 725 for connections to the management system 705 or a portion of the fluid passageway or tube leading to the management system, the connection coupling 710, and the inflation/deflation valve or port 730 of the tube. In another example, the fluid passageway or tube 720 has a first end connecting to the connection or coupling 710, a second end leading to a pressure sensor of the management system 705 that will measure pressure of the fluid in the one or more fluid chambers or sections or groups of fluid chambers of the cushion by measuring fluid from the passageway or tube, and the inflation/deflation valve or port 730 to enable fluid to be added to or removed from the one or more fluid chambers or sections or groups of fluid chambers of the cushion through the cushion connection or coupling.

In one example, a manual or electronic pump is attached to the inflation/deflation valve or port 730, the inflation/deflation valve or port is opened to enable fluid from the pump to be pumped into the one or more fluid chambers or sections or groups of chambers of the cushion 420A, and the pump is operated to pump the fluid into the one or more fluid chambers or sections or groups of fluid chambers of the cushion. In another example, the inflation/deflation valve or port 730 is opened to enable fluid to vent from the one or more fluid chambers or sections or groups of fluid chambers to the atmosphere or environment, for example when a pump is not connected to the inflation/deflation valve or port and/or when the inflation/deflation valve has a separate aperture or vent to the atmosphere or environment. In an alternative embodiment, the inflation/deflation valve or port 730 may be available for manual inflation/deflation of the one or more fluid chambers or sections or groups of fluid chambers or sections or groups of chambers of the cushion, an electronic pump and electronic valve may be included in the management system 705 so that the pump is operated to pump the fluid into the chambers or sections or groups of chambers of the cushion, and the electronic valve is opened to enable fluid to vent from the chambers or sections or groups of chambers to the atmosphere or environment. In an embodiment, the management system 705 operates to maintain a selected pressure and/or fluid volume of the chambers 420 of the cushion or different selected pressures or fluid volumes of sections or groups of chambers of the cushion. Data, power, control signals and other communications are sent between the cushion management system 705 and other devices (e.g. a computer) via a wired USB connection 740 or, alternately, another port or connection or a wireless transceiver.

In another example, the cushion has multiple sections or groups of fluid chambers. The pressure management system 705 has a different pressure sensor for each section or group of fluid chambers and measures fluid pressure for each section or group of fluid chambers. In one aspect, the pressure management system 705 has a different tube 720 and pressure chamber 980 leading to each section or group of fluid chambers and each pressure chamber measures the fluid pressure in the corresponding tube leading to the corresponding section or group of fluid chambers. In another aspect, the pressure management system 705 has a pressure sensor at a connection or valve of each section or group of fluid chambers in place of the pressure chamber 980. In another aspect, the pressure management system 705 has a pressure sensor at a connection or valve of the fluid chamber described above in place of the pressure chamber 980. In another aspect, the pressure management system 705 has fluid volume sensor at a connection or valve of each section or group of fluid chambers or at or in at least one fluid chamber in the section or group of fluid chambers in place of the pressure chamber 980. In each of the above aspects, the pressure sensor(s) and/or volume sensor(s) transmit sensor reports with pressure and/or volume measurements, respectively, to the processor of the pressure management system 705, and the processor operates as described herein.

Figure 8:
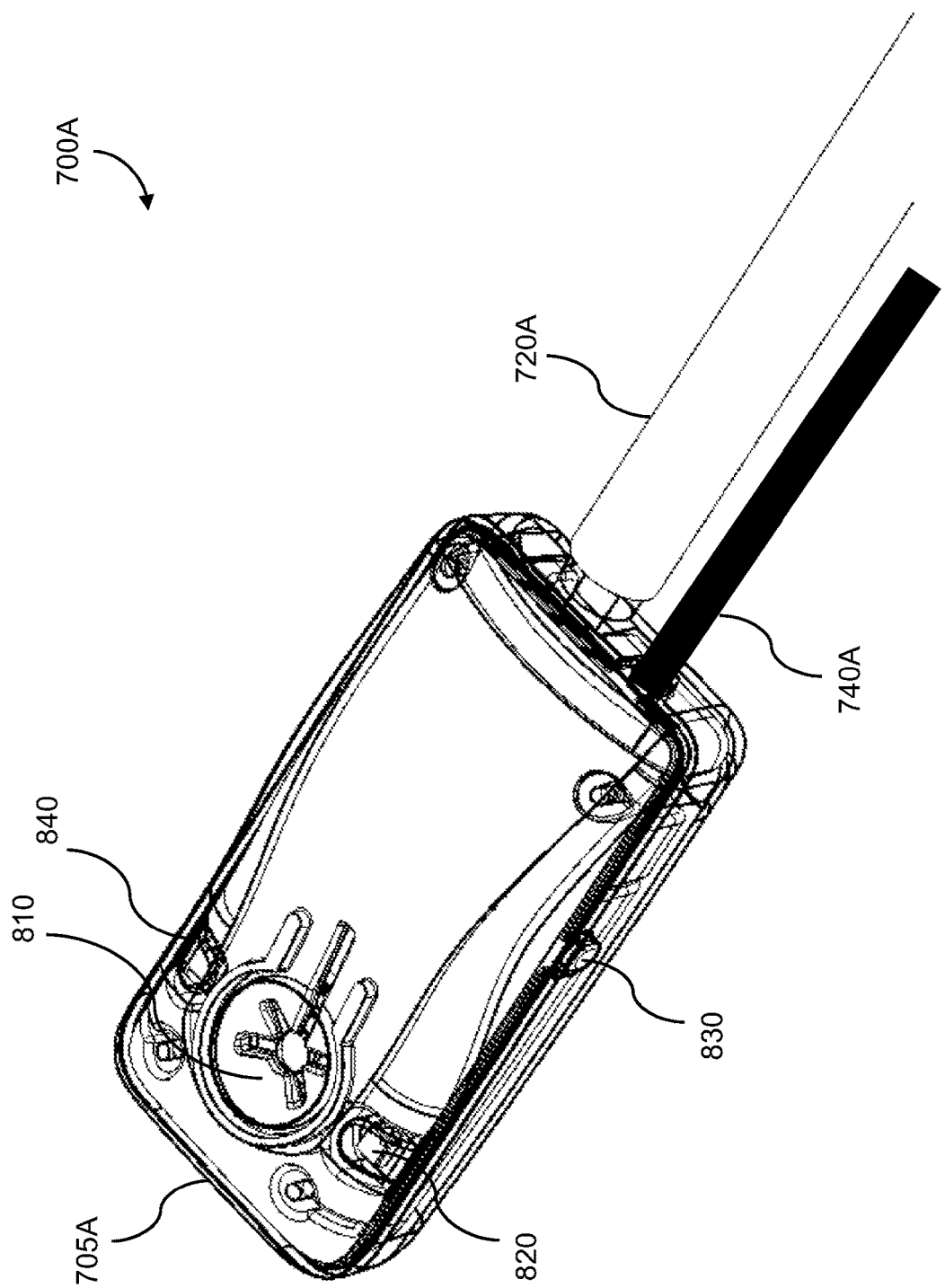
FIG. 8 depicts an exemplary embodiment of a management system.

FIG. 8 depicts an exemplary embodiment of a management system 700A for cushions, such as immersion cushions. The management system 700A can be a separate unit affixed or connected to a cushion or can be embedded into the cushion itself.

Features of the management system 700A include:
A fluid inlet/outlet tube 720A, which includes a fluid connection tube with a Y split that includes a tube connection leading to the management system 705A, a tube connection leading to a connection coupling 710 to the cushion fill valve, and a tube connection to an inflation/deflation valve 730 (either manual or processor/computer controlled) to control fluid addition or removal from the cushion through the cushion fill valve connection;

A communication connection, port, or transceiver 740A (wired or wireless) (e.g. USB cable and connection);

An action or programming button 810 or other input device used to program the management system 610B and/or cause the management system to take one or more actions, including to perform a manual pressure and/or fluid volume check in a selected period of time (e.g. 3 seconds) (e.g. of one or more chambers or sections or groups of fluid chambers) and show results (high, low, or correct cushion pressure and/or fluid volume indicators) or silence warnings (e.g. high or low pressure and/or fluid warnings from one or more indicators) for a selected period of time;

One or more audio/visual indicators 820, including one or more buzzers, speakers, lights, display screens, etc. (including a low-pressure and/or fluid volume indicator, a correct pressure and/or fluid volume indicator, and a high-pressure and/or fluid volume indicator, e.g. of one or more chambers or sections or groups of fluid chambers);

One or more digital or analog auxiliary ports and/or connections 830 which allow for the connection of additional sensors and/or control or communication connections and/or devices with actuators and other outside auxiliary devices.

One or more sensors to monitor pressure and/or fluid volume (of one or more chambers or sections or groups of fluid chambers) at the fluid inlet/outlet 720A and/or of the chambers and transmit sensor data to the processor of the management system 705;

A processor to manage operations of the management system 705, including processing sensor data (e.g. from one or more sensor reports) from one or more sensors at the fluid inlet/outlet tube 720A and/or of the chambers, generate one or more alarms, cause one or more indicators to indicate a status (e.g. low, correct, or high pressure and/or fluid volume of one or more chambers or sections or groups of chambers from one or more indicators), add or remove fluid, receive and execute programing, receive and store user settings (e.g. for a selected pressure and/or volume of one or more chambers or sections or groups of chambers), and control operations of the management system based on the user settings and sensor data.

A battery and/or a connection to a power source.

In an embodiment, the management system includes a power and data connection (e.g. a USB connection) that may be integrated into a cushion or a cushion casing.

Figure 9:
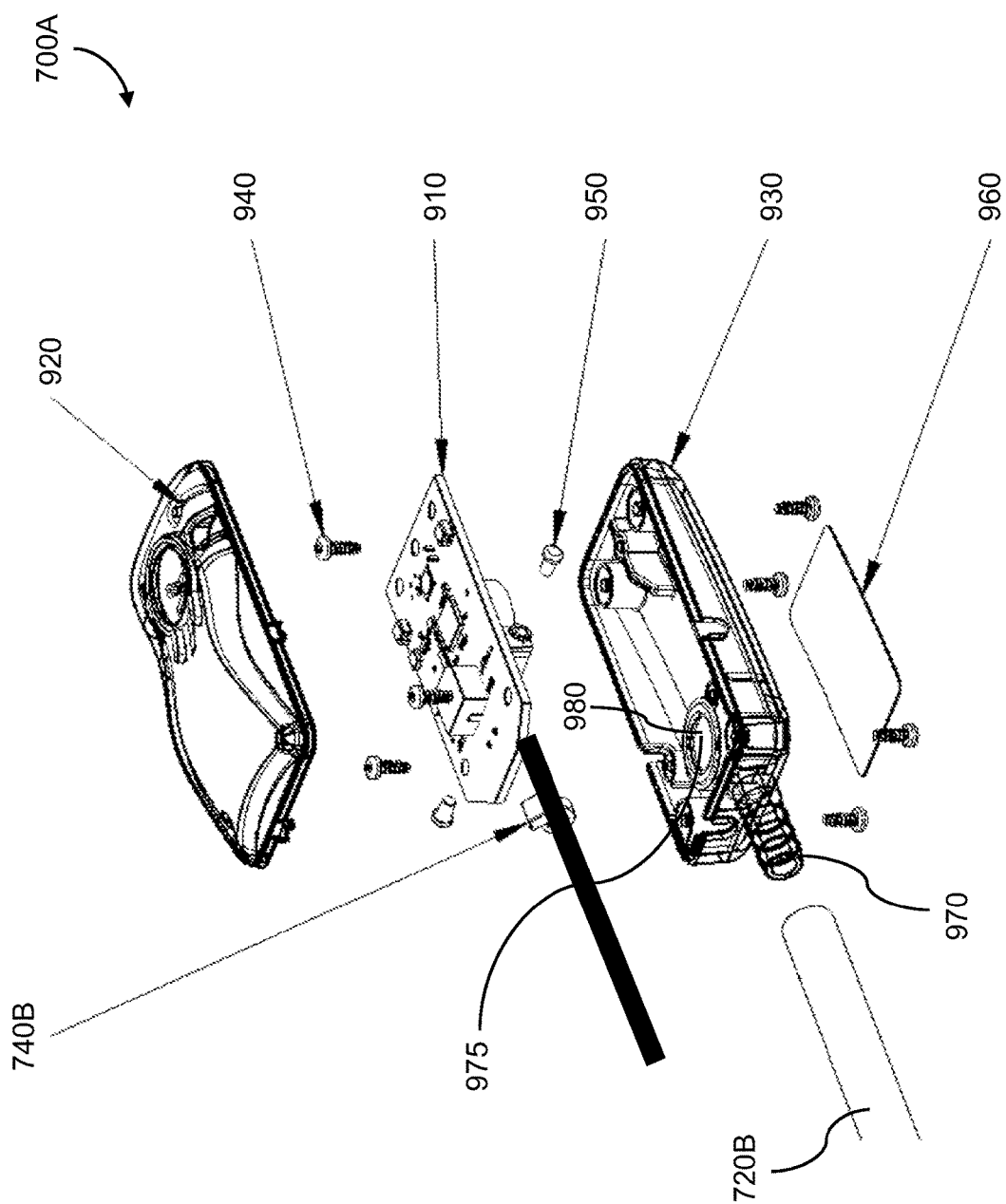
FIG. 9 depicts an exploded view of the management system illustrated in FIG. 8.

FIG. 9 depicts an exploded view of the management system illustrated in FIG. 8. The management system 705A includes a printed circuit board assembly (PCBA) 910, a top housing 920, a bottom housing 930, fasteners (e.g. screws) 940, one or more auxiliary ports 950, and labeling 960. A clip may be used to secure the USB connection 740B to the bottom housing 930, and the fluid inlet/outlet tube 720B connects to a fluid tight connection 970 to the bottom housing. The PCBA 910 includes at least one pressure sensor to measure ambient pressure and at least one sensor to measure the pressure of fluid in one or more chambers or sections or groups of chambers of the cushion. In the embodiment of FIG. 9, the bottom housing 930 includes a recess and seal 975 that forms a pressure chamber 980 between the PCBA 910 (in the area that includes a pressure sensor for measuring the pressure of the fluid in one or more chambers or sections or groups of chambers of the cushion) and the fluid inlet/outlet tube 720B connection of the housing. In this embodiment, a separate pressure sensor on the PCBA 910 (not shown) measures ambient pressure.

Figure 10A:
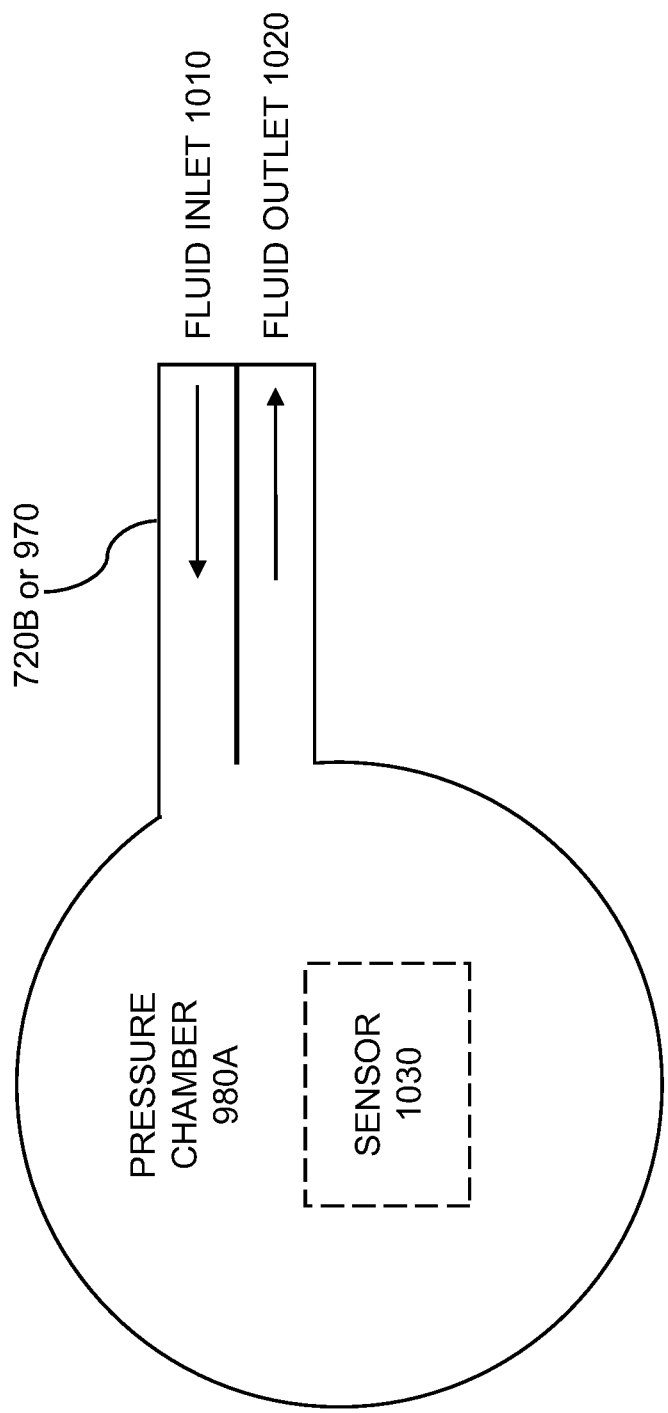
FIGS. 10A-B depict non-limiting examples of fluid flow through a management system.
Figure 10B:
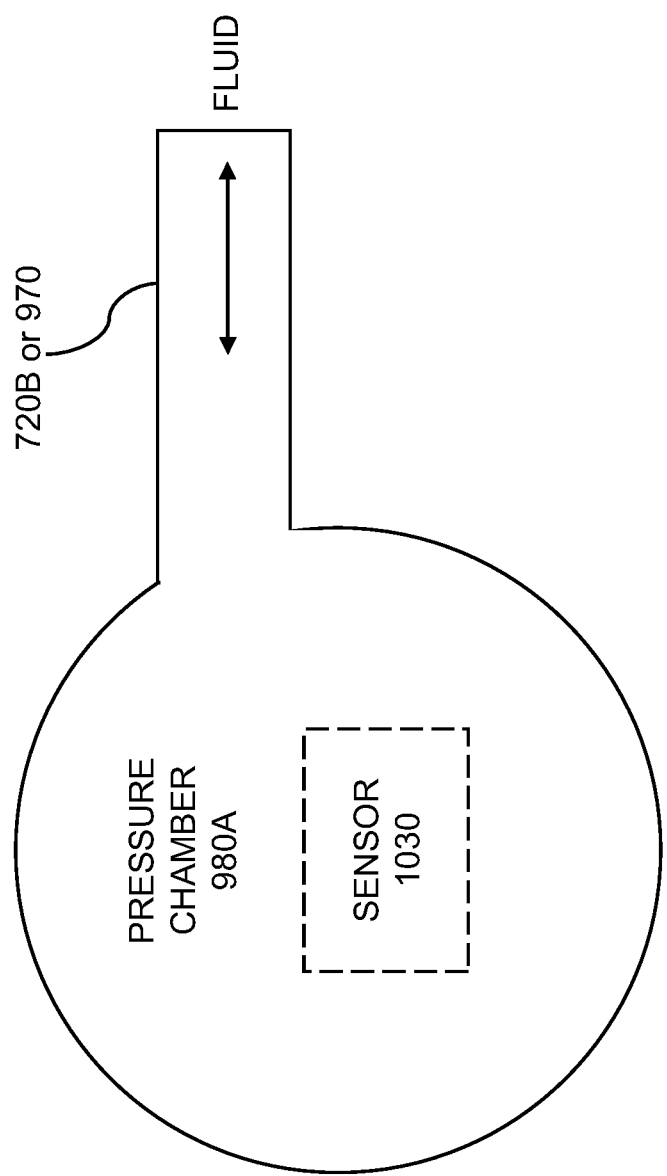

FIGS. 10A-B depict non-limiting examples of fluid flow through the management system. In the example of FIG. 10A, the fluid tight connection 970 or a portion of the tube 720B (e.g. if there is no separate connection to/through the housing) has a fluid inlet 1010 and a fluid outlet 1020. Between the fluid inlet 1010 and the fluid outlet 1020 is (a) a pressure chamber 980A and (b) a pressure sensor 1030 in the pressure chamber to measure fluid pressure in the pressure chamber. The fluid inlet 1010 enables fluid to enter the pressure chamber 980A from the fluid tight connection 970 and/or the portion of the tube 720 so that a fluid pressure of the fluid may be measured by the pressure sensor 1030, and the fluid outlet 1020 enables fluid to leave the pressure chamber via the fluid tight connection 970 and/or the portion of the tube 720, and return back to the connection or coupling 710 and/or the inflation/deflation valve 730 via the remaining portion of the tube. In the example of FIG. 10B, the fluid tight connection 970 or the tube 720B does not have a separate fluid inlet 1010 or fluid outlet 1020. Instead, fluid flows into the pressure chamber 980A from the fluid tight connection 970 or the tube 720B (e.g. if there is no separate connection to/through the housing) and the pressure sensor 1030 measures the fluid pressure in the pressure chamber. The pressure chamber 980A may be located, in one example, inside the housing 920/930 of the management system 705A and connect to the fluid tight connection 970. In another example, the pressure chamber 980A may be located at the inflation/deflation valve 730 of the fluid inlet/outlet tube 720B, the connection coupling 710 to the cushion 410A fluid fill valve, or the fluid fill valve of the cushion. In another example, the pressure chamber may be one or more chambers 420 of the cushion 410A itself.

Figure 11:
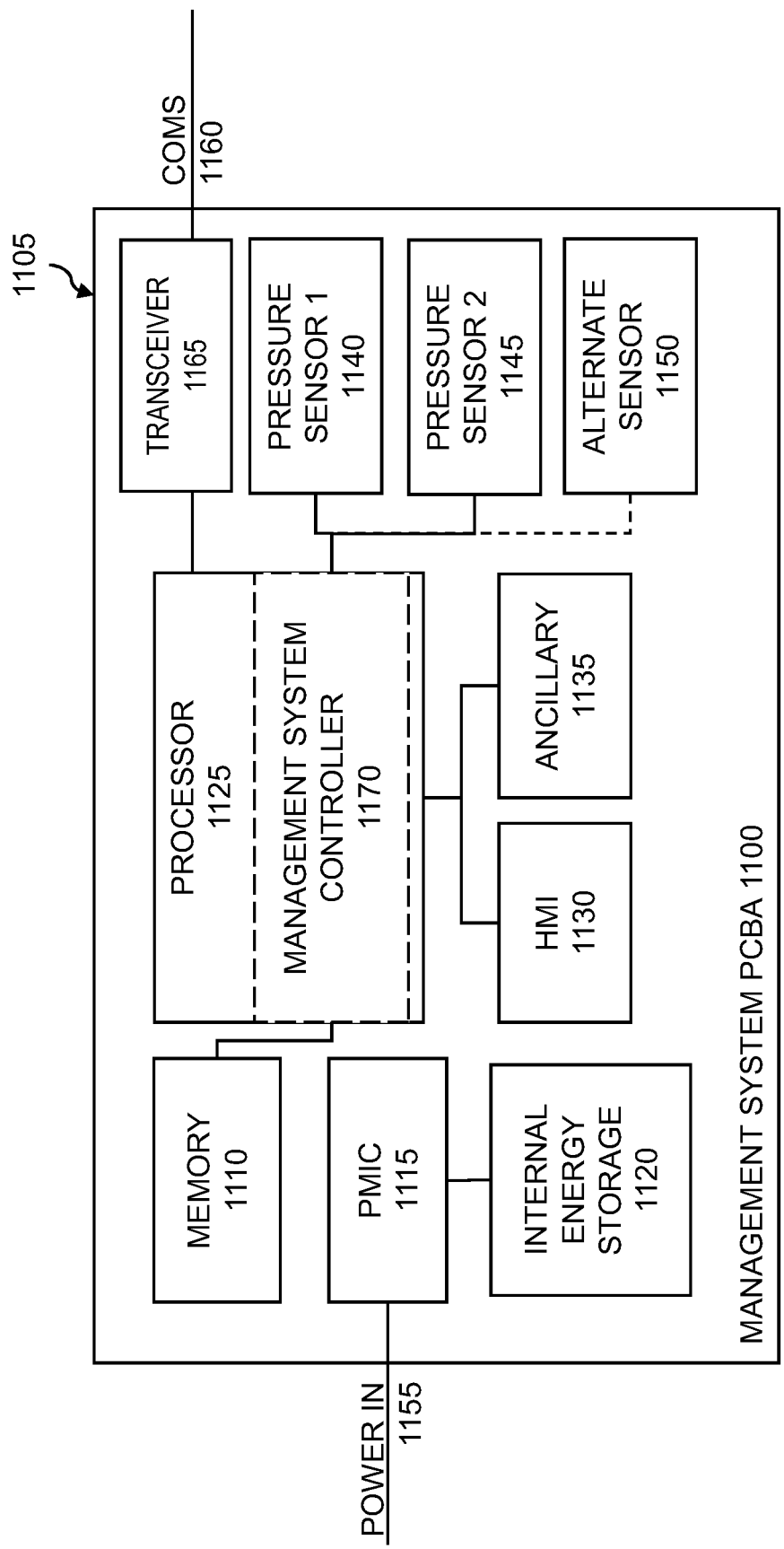
FIG. 11 depicts an exemplary diagram of a hardware components of a management system.

FIG. 11 depicts an exemplary electrical diagram of a circuit board (PCBA) 1100 of the management system 1105. The management system 1105 may be used as a management system that is integrated with a cushion or as a management system that is not integrated with a cushion (e.g. at manufacture), such as the non-integrated add-on system 700 of FIGS. 7-9. The circuit board 1100 includes memory 1110, a power management integrated circuit (PMIC) 1115, internal energy storage 1120, one or more processors/controllers 1125, a human machine interface (HMI) 1130, ancillary circuit management 1135, pressure sensor 1 1140, pressure sensor 2 1145, an alternate sensor 1150, a power input 1155, one or more communication ports or devices 1160, and one or more optional wireless and/or wired transceivers 1165. Memory 1110, which is hardware, may include volatile and non-volatile non-transitory computer storage media for storing information and programming. The energy storage 1120 may include capacitance devices, replaceable batteries, rechargeable batteries, rechargeable and coin cell, wireless recharging power packs, USB chargeable power packs. The management system controller 1170 is software that executes on one or more processors 1125 on the management system PCBA 1100 and is stored in memory 120. The power input 1155 and communication port 1160 may be a single connection, such as a USB connection. Additionally or alternatively, communication with the management system 1105 may be accomplished via wireless communication via the transceiver 1165, such as using BLE. In the embodiment of FIG. 11, the ancillary circuit management 1135 includes one or more digital/analog auxiliary ports/auxiliary port connections and manages power and communications with auxiliary devices connected to the management system 1105. Similarly, in the embodiment of FIG. 11, the HMI 1130 includes one or more output devices, such as one or more indicator lights, speakers, screens, haptic feedback devices, other feedback devices, or other output devices and one or more input devices, such as one or more buttons, programming controls, screens, microphones and voice activated circuitry and/or programming, other input devices, and the associated circuitry and/or programming of the foregoing.

In an exemplary embodiment, one or more processors of the management system 1105 (e.g. processor 1125) is configured to establish one or more communication connections via the communication devices 1160 and/or transceivers 1165 between a smart cushion and one or more wireless devices over which data is transmitted and received by the processor and the one or more wireless devices. The wireless device and the processor 1125 may communicate via the transceiver 1165 using one or more of cellular, RFID, 802.11, Wi-Fi, Bluetooth, Bluetooth Low Energy (BLE) (as defined in the Bluetooth Core Specification incorporated herein by reference), and near field communication.

Figure 12:
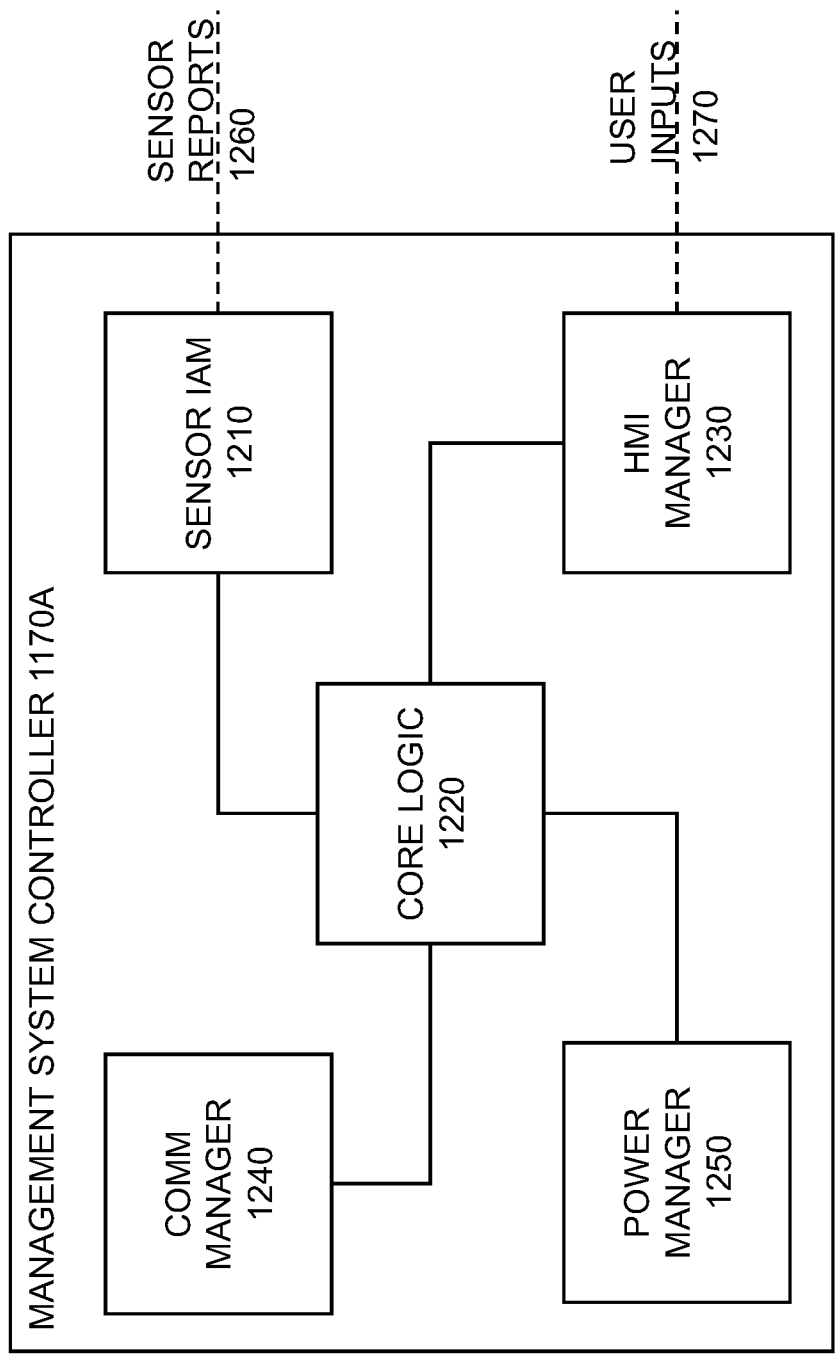
FIG. 12 depicts a software architecture block diagram of a management system.

FIG. 12 depicts a software architecture block diagram of operations performed by one or more processors of the management system 1105 (e.g. the management system controller 1170 of the processor 1125). Operations of the software include a sensor information assurity manager (IAM) 1210 to receive and process sensor reports as discussed above, core logic 1220, a human machine interface (HMI) manager 1230 to receive and process user inputs and generate outputs to users (e.g. via indicators), a communications manager 1240, and a power manager 1250.

The sensor information assurity manager (IAM) 1210 manages one or more sensor reports 1260 (a communication with or identifying data sensed by the sensor and/or with one or more commands) from one or more sensors on or used by the smart cushion 110 and may include communication and identification processing capabilities. In some embodiments, the sensor IAM 1210 resides on a security or arbitration processor instead of the main processor 1125. Additionally or alternatively, functions of the sensor IAM 1210 may be performed by a dedicated communication processor. Sensor reports 1260 received and managed by the sensor IAM 1210 may include fluid pressure sensor reports, fluid volume sensor reports, wetness sensor reports, humidity sensor reports, temperature sensor reports, non-contact sensor reports, image sensor reports, and user sensor reports. Sensor reports 1260 may include data stored in one or more of long-term or short-term system memory 1110 or read from an auxiliary port on the management system (e.g. transmitted from a processor of an ancillary device and received by ancillary circuit manager 1135). A sensor report may include measurement data and additional data beyond measurements, including sensor status, measurement time, confidence levels, or other information. The depicted embodiment of the sensor IAM 1210 may include logic to manage the sensors, including one or more of turning a sensor on and off, setting sensor parameters, adjusting sensor volume, requesting regional interrogation, and/or other operations.

Non-contact sensors are devices used to take a measurement, often a distance, without coming in contact with the detected object. There are many types of non-contact sensors, including optical (e.g. LIDAR), acoustic (e.g. ultrasonic), radar, and capacitive sensors. Microphones may additionally be included as a non-contact sensor. Image sensors detect and convey information that constitutes an image or series of images/video, wherein the image(s)/video may contain light or electromagnetic radiation information on an area. These sensor reports interface to the specific sensor types in the system to identify measurements, detections, number, efficiency, health, degraded performance, states, statuses, and/or other data of each sensor in a system of sensors used by or in connection with a smart cushion 110.

The core logic 1220 is responsible for user state determination, cushion status determination, and primary decision making of the management system 1105. In an exemplary embodiment, the core logic 1220 may calculate the cushion pressure, determine whether the user is in or out of the seat, determine if the user is offloading, and/or determine if the user should take any actions based on one or more inputs from other processes of the management system 1105 and data from memory. The core logic 1220 may receive inputs from other processes of the management system 1105, including the sensor IAM 1210, HMI manager 1230, communication manager 1240, and/or power manager 1250. Additionally, the core logic 1220 may cause one or more processes of the management system controller 1170A to take an action.

The HMI Manager 1230 processes received user inputs and is responsible for causing user feedback to be sent to the user based on one or more user inputs 1270 and/or input from the core logic 1220 of the management system controller 1170A. In an example, the user pushes a button (e.g. 810 FIG. 8) to generate an input, and the input is processed by the HMI manager 1230 which causes the HMI manager to send one or more inputs to the core logic 1220. In another example, the core logic 1220 sends an input to the HMI manager 1230 which the HMI manager processes and causes one or more indicator lights (e.g. indicator 820 FIG. 8) to change state.

The communication manager 1240 manages communications through system connections and off-board connections to enable communication and coordination between the management system 1105 and smart devices, wheelchairs, and/or devices to an accessory (ref. FIG. 3), including cooperative actions between the management system and other devices. In an example, a smart device 330 is communicatively coupled to the communication manager 1240 of the management system controller 1170A (e.g. using one or more transceivers included in the processor 1125 or the transceiver 1165) via a wireless connection (e.g. via Bluetooth pairing and communications). The wireless connection is established between a first wireless communication processor (e.g. the processor 1125 of the management system 1105) on the smart cushion and a second wireless processor on the paired smart device 303. The first wireless communication processor 1125 and second wireless communication processor establish secure connections between the smart cushion 110F and the smart device 303. In some embodiments, the communication manager 1240 identifies other data sources and retrieves data from other data sources, including sensors and/or actuators of one or more medical device (e.g. wheelchair) or an accessory to a wheelchair in the area. In an example, the communication manager 1240 may automatically recognize and pair with devices over Bluetooth that have approved or recognized universal identification number (UUIDs) known to the device (i.e. stored in memory). Additionally our alternatively, other devices may connect to the smart cushion 110F and communicate with the communication manager 1240 automatically based on the UUID or other unique identifiers of the smart cushion.

The power manager 1250 manages the power usage, charging, and sleep behavior of the management system 1105 based on information received from one or more of the PMIC 1115, data from memory, and one or more inputs from the core logic 1220.

Exemplary Pressure Processing

For individuals who use wheelchairs, or spend significant time in stationary positions such as bed, an important factor to avoiding pressure injuries isn't simply to know the pressure on their body, but to also turn pressure readings into actionable information that the individual or their care team can use to make good decisions. That information includes the user's time-inSeatt and offloading history based on the pressure data and guidance provided to the user and their care team on the best actions to take to avoid pressure injuries.

Figure 13:
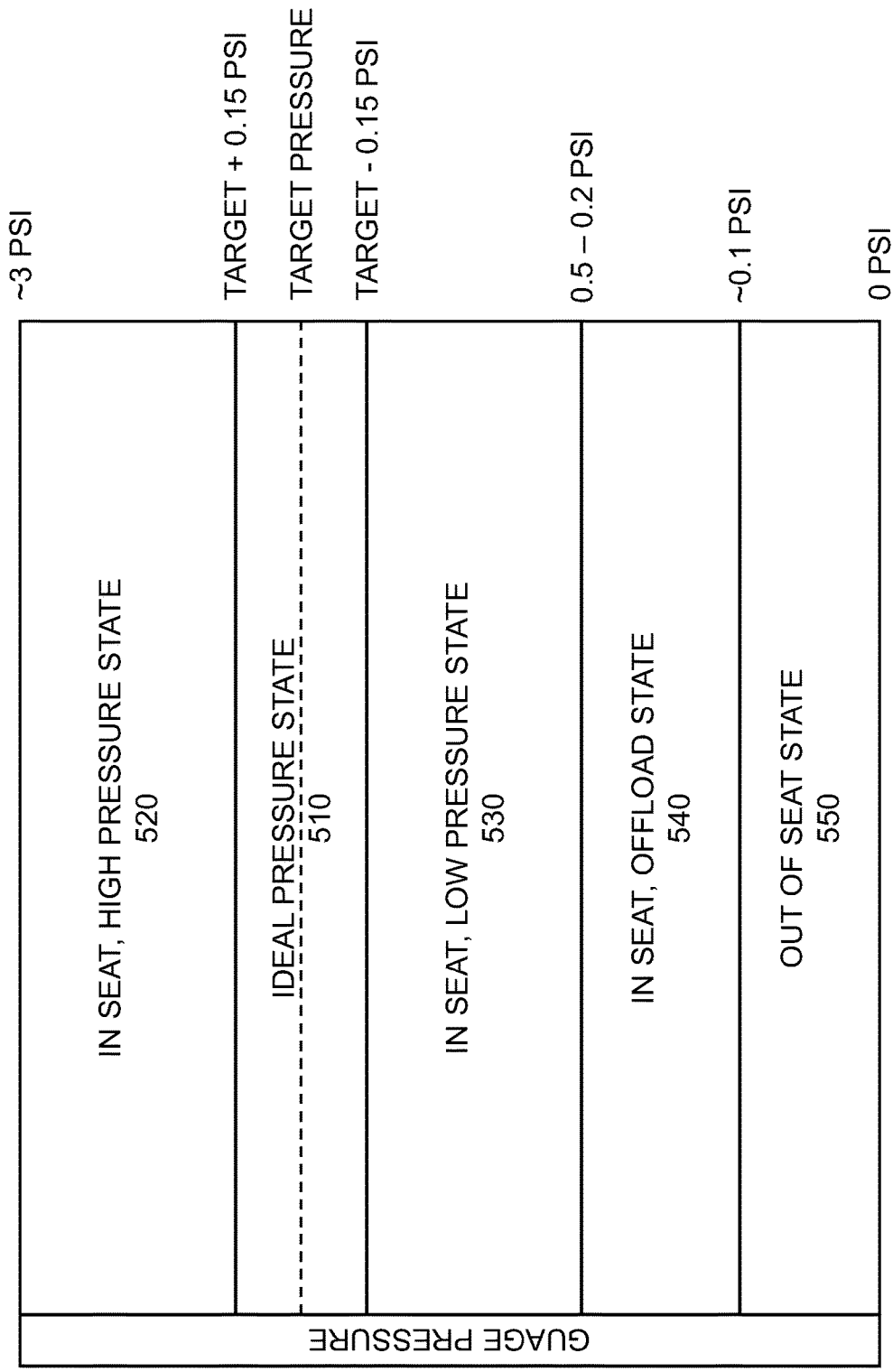
FIG. 13 depicts the pressure behavior of FIG. 5 annotated with non-limiting example pressure thresholds.

FIG. 13 depicts a pressure behavior of a cushion, such as an immersion cushion, during use annotated with non-limiting example pressure thresholds. These pressure thresholds may be used by an exemplary logic (e.g. of the management system controller 1170) to process pressure data and determine a current pressure state of the user in the cushion. Pressure data may be processed on the cushion or the management system 110 as described above.

Gauge pressure is an exemplary type of pressure determined by the management system controller 1170 of the management system 1105. Gauge pressure is a measured pressure relative to atmospheric pressure. For example, in one embodiment, the management system controller 1170 determines a gauge pressure in the pressure chamber 980 of FIG. 9 and/or the pressure chamber 980A of FIG. 10, determines ambient pressure at the management system using an ambient pressure sensor, and determines the pressure at the fluid chamber or section or group of fluid chambers as a function of the pressure in the pressure chamber and the pressure from the ambient pressure sensor (e.g. by subtracting the ambient pressure (including an absolute or processed form thereof) from the pressure in the pressure chamber (including an absolute or processed form thereof)). A non-limiting example of how a pressure chamber gauge pressure is calculated by the controller 1170 includes:

- A first pressure sensor (e.g. pressure sensor 1 1140) takes a measurement of the ambient pressure at the management system 1105 and communicates a first sensor report with the measurement of the ambient pressure to the processor 1125 of the management system 1105;
- A second pressure sensor (e.g. pressure sensor 2 1145) takes a measurement of the internal pressure of one or more fluid chambers or sections or groups of fluid chambers (e.g. at pressure chamber 980/980A) and communicates the second sensor report with the measurement of that internal pressure to the processor 1125 of the management system 1105;
- The management system controller 1170, which is software, uses one or more correction factors and/or software routines (e.g. from memory 1110) to pre-process the measurements in the received sensor reports as part of the sensor IAM 1210 of the management system controller 1170 and convert the measurements in the received sensor reports to absolute pressure values in the correct (and same) units, resulting in the absolute atmospheric pressure and the absolute pressure of the pressure chamber;
- A process of the management system controller 1170 (e.g. core logic 1220) of the processor 1125 calculates the gauge pressure of the pressure chamber 980/980A by subtracting the absolute atmospheric pressure from the absolute pressure of the pressure chamber.

The one or more processors 1125 of the management system 1105 may use one or more digital filters to pre-process the received sensor reports of the one or more sensors in preparation for the pressure chamber gauge pressure calculations previously disclosed. In an embodiment, a sensor report received from a sensor of the management system 1105 is first filtered by the processor based on one or more previous sensor reports (e.g. retrieved from memory) of the same sensor using a digital filter, which is software. In an example, a recursive, infinite impulse response (IIR) filter is used to reduce noise in a received sensor report as part of the sensor report processing, where the IIR is part of the sensor IAM 1210 of the management system controller 1170A. An IIR filter calculates an output from the filter, which may be used as an input to one or more calculations of the system, by calculating a filtered sensor report using as inputs the current and previous inputs and previous outputs of the filter. Other data filtering approaches such as a median filter, mean filter, or other time-based filters may be used in some embodiments. Frequency response filters such as a low-pass filter or band-pass filter may additionally or alternatively be used by the system to pre-process sensor readings in preparation for use by the core logic 1220 of the smart cushion controller 1770A.

In this exemplary embodiment of pressure processing, the gauge pressure is used by the core logic 1220 of the management system controller 1170A on the processor 1125 to determine a current state of the cushion (e.g. one of states 510-550). The current state of the cushion is determined by comparing the gauge pressure of the pressure chamber to the pressure thresholds shown in FIG. 13 per the logic below:

- If gauge pressure<~0.1 pounds per square inch (PSI) then the user is OUT OF SEAT 550;
- If gauge pressure>~0.1 PSI and gauge pressure<~0.3 PSI then the user is IN SEAT, OFFLOADING 540;
- If gauge pressure>~0.3 PSI and gauge pressure<(Target Pressure−an offset value of 0.15 PSI) then the user is IN SEAT, LOW PRESSURE 530 and the user should be encouraged to increase pressure of the fluid in their cushion;
- If gauge pressure>(Target Pressure−an offset value of 0.15 PSI) and gauge pressure<(Target Pressure+an offset value of 0.15 PSI) then the user is IN SEAT, IDEAL PRESSURE 510; and,
- If gauge pressure>(Target Pressure+an offset value of 0.15 PSI) then the user is IN SEAT, HIGH PRESSURE 520 and the user should be encouraged to decrease pressure of the fluid in their cushion.
- A greater or lesser PSI value than 0.15 PSI may be used as an offset value in place of the 0.15 PSI in other embodiments, such as in the range of 0-1 PSI.

Since each user will have a different combination of weight, buttock surface area, and seating support system, the ideal pressure state 510 target is not a single number for all people. It does however typically range from 0.2 to 3 PSI, as an example, with lower pressures being preferable. The ideal pressure state 510 pressure target can be programmed into the management system 1105 for each user. In an exemplary embodiment, a user would work with a physical therapist, occupational therapist or authorized technician to determine and program their ideal pressure target as follows:

- Put the management system 1105 in programming mode, e.g. using a programming or action button or input device from the HMI 1130;

Work with their therapist or technician to ensure the seat cushion is inflated correctly and that they are seated correctly, with proper weight distribution across the cushion; and, Press and hold an input to the management system 1105 to indicate that the current pressure is an ideal pressure, e.g. using the programming or action button or input device from the HMI 1130, and wait for confirmation that the pressure has been saved in memory.

Generally, the goal of the system should be to offer the user feedback and encouragement to maximize the amount of time that their immersion cushion is at the proper pressure while seated. In addition, offering the user feedback on when they have successfully offloaded and a record of the amount of time they have spent in the seat, out of the seat, and offloaded will give them the tools to successfully manage their pressure injury and/or skin health.

Exemplary Power Management

The data that users need to manage their skin health must provide an accurate picture of their time in seat and out-of-seat. This means that any solution may effectively manage power and sleep modes to collect data when there is a change in state.

Figure 14:
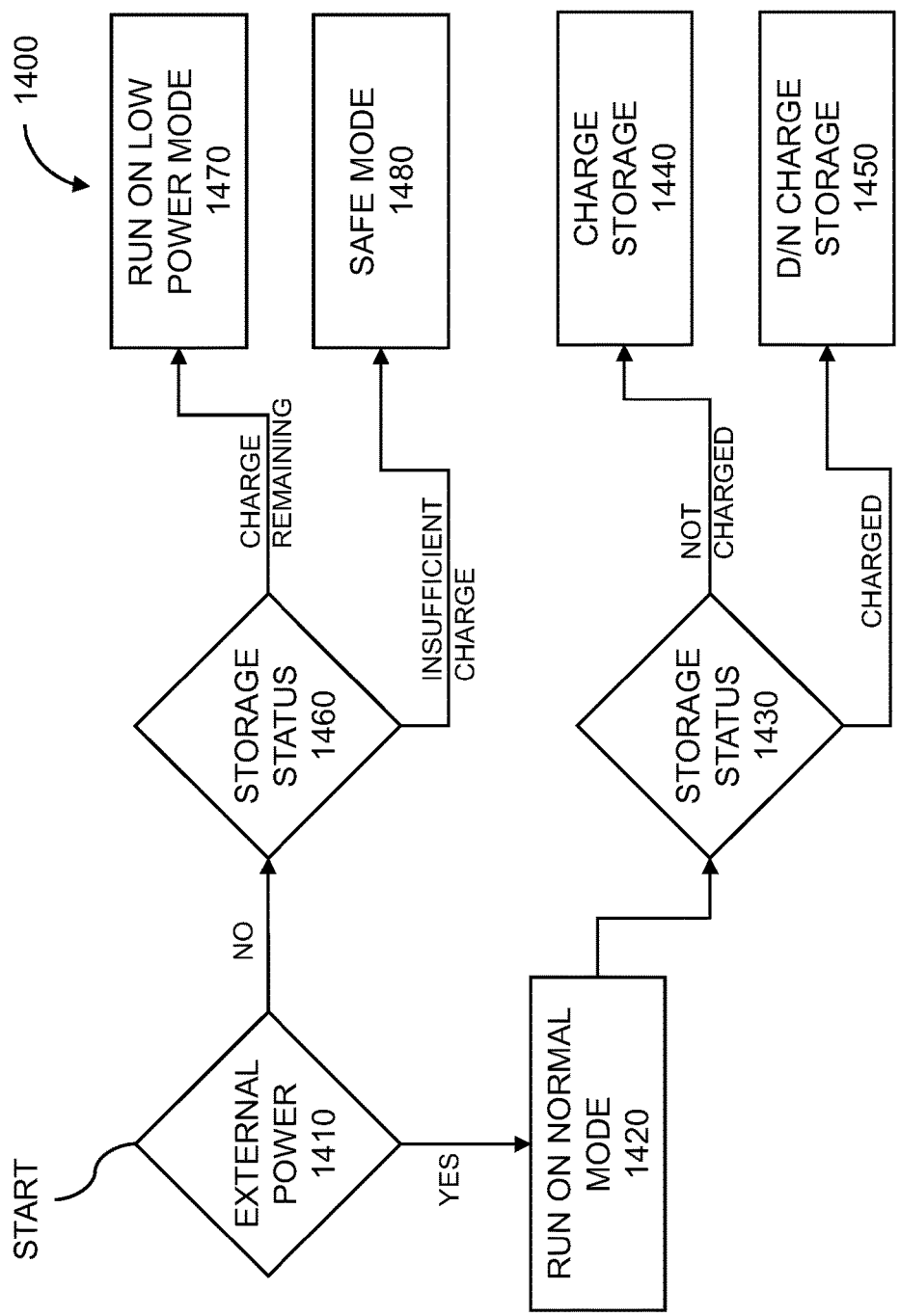
FIG. 14 depicts exemplary power management operations performed by a power manager operating on one or more processors of the management system.

In an embodiment, the management system 1105 does not have its own power source. Instead, it uses external power (e.g. from a wheelchair battery) for power by connecting the power input 1155 to a wheelchair or an accessory to a power wheelchair. This means that the user does not have a separate device to charge; charging their wheelchair per its manufacturer's specifications will provide the power needed to the management system 1105. The management system 1105 is designed so that the power usage is minimal and should not significantly affect the battery life of the user's wheelchair. Additionally, the management system 1105 has an internal power storage 1120 that is able to use stored internal power to continue monitoring cushion pressure for a period of time after the wheelchair is turned off, giving the user accurate time-in-seat data so they can manage their seating health. FIG. 14 depicts exemplary power management operations 1400 performed by the power manager 1250 operating on one or more processors of the management system (e.g. the PMIC 1115 and/or main processor 1125 of the management system 1105). The following steps are followed:

When a voltage sensor or other sensor on the PMIC 1115 or another component of the management system 1105 recognizes that there is external power (e.g. power received via USB) available at 1410, the management system operates in a normal operating mode 1420 in which no power saving/controlling measures are taken by the management system (e.g. no changes in the operation or behavior of a user interface of the HMI 1130, no change in the frequency of measurements, communications, and/or indications, or and no other adjustments in the function of the management system in order to extend the amount of time the management system can operate on available power in the internal energy storage 1460). During normal operating mode 1420, the internal energy storage 1120 status is checked at 1430 by the power manager 1250. In an embodiment, if the internal energy storage 1120 is not charged at 1430, then the power manager 1250 sends one or more commands to the PMIC 1115 which causes the PMIC to charge the internal energy storage at 1440. Alternatively, if the energy storage 1120 is already charged at 1430, then the power manager 1250 may choose not to charge the internal energy storage at 1450. In an alternative embodiment, one or more of the functions described for the PMIC 1115 or power manager 1250 may be performed automatically by one or more hardware components on the management system PCBA 1100.

When a voltage sensor or other sensor on the PMIC 1115 or another component of the management system 1105 recognizes that there is no external power (e.g. power received via USB) available at 1410, the management system checks the status of the internal energy storage 1120 at 1460. If there is charge remaining in the internal energy storage 1120 at 1460, then the management system 1105 runs in low power mode at 1470. Low power mode 1470 in an embodiment may change the behavior of the user interface, change the frequency of measurements, communications, and/or indications or otherwise adjust the function of the device with the goal of extending the amount of time the device can operate on the available internal energy storage 1120. If there is insufficient charge remaining in the internal storage 1120 at 1460, then the management system 1105 will turn off all but the most essential functions to run in safe mode at 1480 where safe mode is intended to preserve the health of the internal energy storage 1120 for those essential functions.

Additionally or alternatively, the management system 1105 may switch modes of operation based on one or more indications of user presence or the lack of user presence. In an example, one or more accelerometers amd/or an inertial measurement unit (IMU) are included as one or more alternative sensors 1150 as part of the management system 1105 and one or more sensor reports from the accelerometers and/or IMU are processed and used by the controller 1170 to identify minute accelerations due to the presence of a person on a smart cushion. If the minute accelerations are detected (e.g. by the management system controller 1170) then the management system operates in a normal operating mode. In the absence of minute accelerations, the management system operates in a sleep or safe mode 1480. An IMU has one or more sensors on three axes that senses and provides specific force, angular rate, and/or attitude information of the management system, including yaw, pitch, and/or roll and deviations to each. The same approach may be used to change operating modes of the management system based on impulses of pressure received via the one or more pressure sensors of the device.

Bladder Construction

Figure 15:
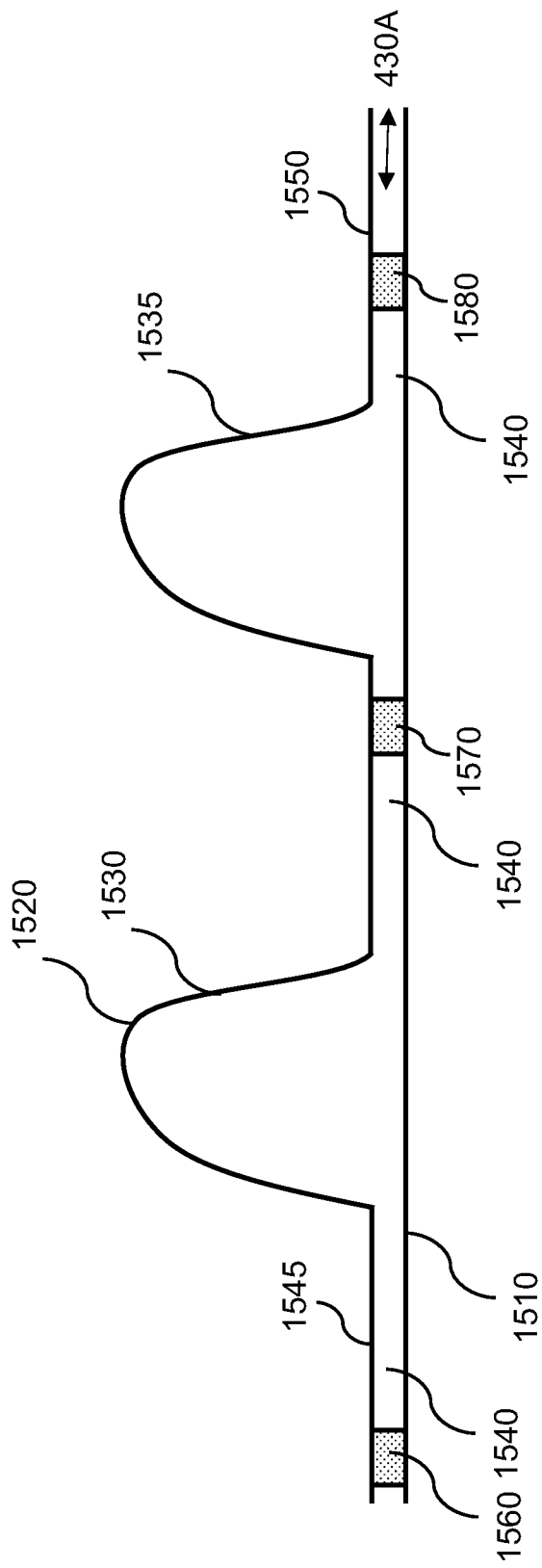
FIG. 15 depicts a side cross section of a fluid bladder construction.

One or more features of the previously described exemplary management system 1105 may be directly built into a cushion or the bladders of a cushion, such as an immersion cushion. FIG. 15 depicts a side cross section of an air bladder construction, which includes a multi-piece construction from a bottom layer 1510 and a top layer 1520 of a flexible fluid-holding material, such as rubber or an equivalent material. Multiple fluid holding chambers 1530 and 1535 are formed between the top layer 1510 and the bottom layer 1520 with channels 1540 between the chambers and on the other/outer sides of the chambers between one side 1545 and another side 1550 and the chambers. The layers are sealed with a seal 1560 between sections, such as via a heat seal, adhesive seal, or sonic weld. The air bladder additionally includes one or more ports or fill valves 1570, 1580, and/or 430A.

Figure 16A:
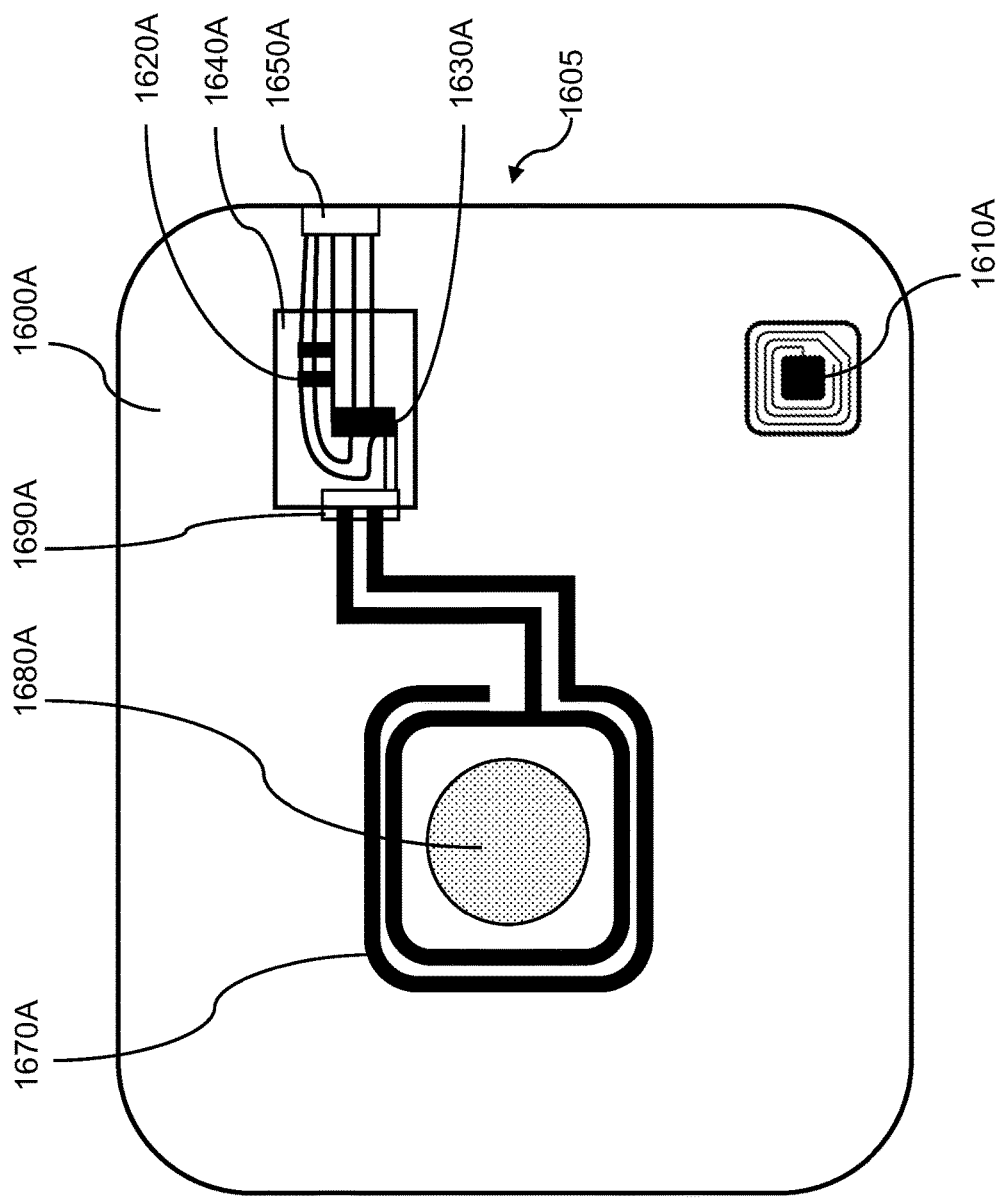
FIG. 16A depicts electrical components of a cushion.

FIG. 16A depicts an exemplary embodiment of a cushion 1600A, such as an immersion cushion, in which control electronics 1605A are included in the construction of the cushion. One or more embedded identification and/or communication devices 1610A, such as a BLE beacon, RFID tag, or other wireless digital ID, may be included in the cushion 1600A. The cushion 1600A may include one or more sensors 1620A, such as a MEMS sensor for measurement of pressure, force, temperature, humidity, orientation, deflection, and/or wetness. Additionally or alternatively, one or more piezo film sensors or capacitive sensors are used to sense presence or direct force. In an embodiment, one or more processors 1630A may be included directly in the construction of the cushion 1600A, for example on an embedded rigid or flexible printed circuit board assembly (PCBA) 1640A that has an interface and communications electronics for implantable sensors/devices. The one or more processors 1630A may be communicatively coupled, via wired or wireless devices/means, to one or more external devices (e.g. management system 1105). In another embodiment, processing is done off-board of the cushion 1600A, and the sensors 1620A are connected to an external device for power and communication with a physical connection 1650A.

In an embodiment, one or more conductive ink printed circuits may be printed onto the interior or exterior of the layers of the cushion 1600A. The conductive ink printed circuits may be connected to one or more sensors, rigid or flexible PCBA's, or other components of the cushion 1600A. Additionally or alternatively, the conductive ink may be printed to create an antenna for communication with external devices.

In the embodiment of FIG. 16A, conductive ink is printed on the outside of the upper layer 1520 of a 2-piece cushion 1600A. The conductive ink pattern 1670A is comprised of at least two independent conductive loops separated by a small gap. This pattern is drawn around a target area 1680A of the cushion 1600A most likely to be the location of user incontinence. Additionally or alternatively, the target area 1680A may be the extruded or formed part of a fluid chamber in an area for which it may be difficult to print a pattern and which may shed any moisture towards the printed conductive loops. The printed conductive loops 1670A are connected via a connection 1690A to a flexible or rigid PCBA 1640A that includes a pre-processing and/or amplification circuit which couples the conductive loops to the input of a processor 1630A. The processor 1630A monitors for either a decrease in resistance between the two loops or a closed circuit (presence of voltage), both of which may indicate wetness, to determine if the cushion 1600A is wet and therefore there has been an incontinence event. In an alternative embodiment, the printed pattern 1670A may be used as a resistive heating element of the PCBA 1640A to heat the cushion 1600A and may be controlled by the one or more processors 1630A of the PCBA. Control of the heating element (e.g. on and off) may be done automatically by one or more processors 1630A of the cushion 1600A based on readings from an internal or external temperature sensor 1620A, or it may be turned on and off manually by the user via a switch of the cushion's control electronics 1605A or when a control signal is received from an external wireless device, such as the main processor 1125 of the management system 1105 or associated transceiver. In another embodiment, the printed pattern 1670A may be used to create TENS/electrical stimulus pads to assist with physical therapy.

One or more electrically controlled fluid control devices (e.g. electronically controlled valves) may be embedded in the cushion 1600A for control by the processor 1630A (or alternately processor 1125). In an example referencing the two-part cushion of FIG. 15, an electronically operated valve is placed in the channel 1540 connecting two sections of the cushion (e.g. between two fluid chambers 1530 and 1535 or between two groups or sections or fluid chambers). The valve receives one or more control signals from a processor 1630A of the cushion 1600A and, in response thereto, enables, disables, restricts, or expands the ability of fluid to flow through the channel 1540, for example by opening or closing the valve or partially opening or closing the valve. In another example, the fluid in the cushion 1600A is a magneto-rheological fluid and the fluid control electronics may be embedded in the cushion construction so that the viscosity of the magneto-rheological fluid may be changed based on one or more control signals from one or more processors 1630A of the smart cushion 1600A. In another example, one or more fluid flow sensors are placed in the chambers 1530 and 1535 and/or one or more sections 1540 for monitoring and real-time adjustment of the fluid flow.

Figure 16B:
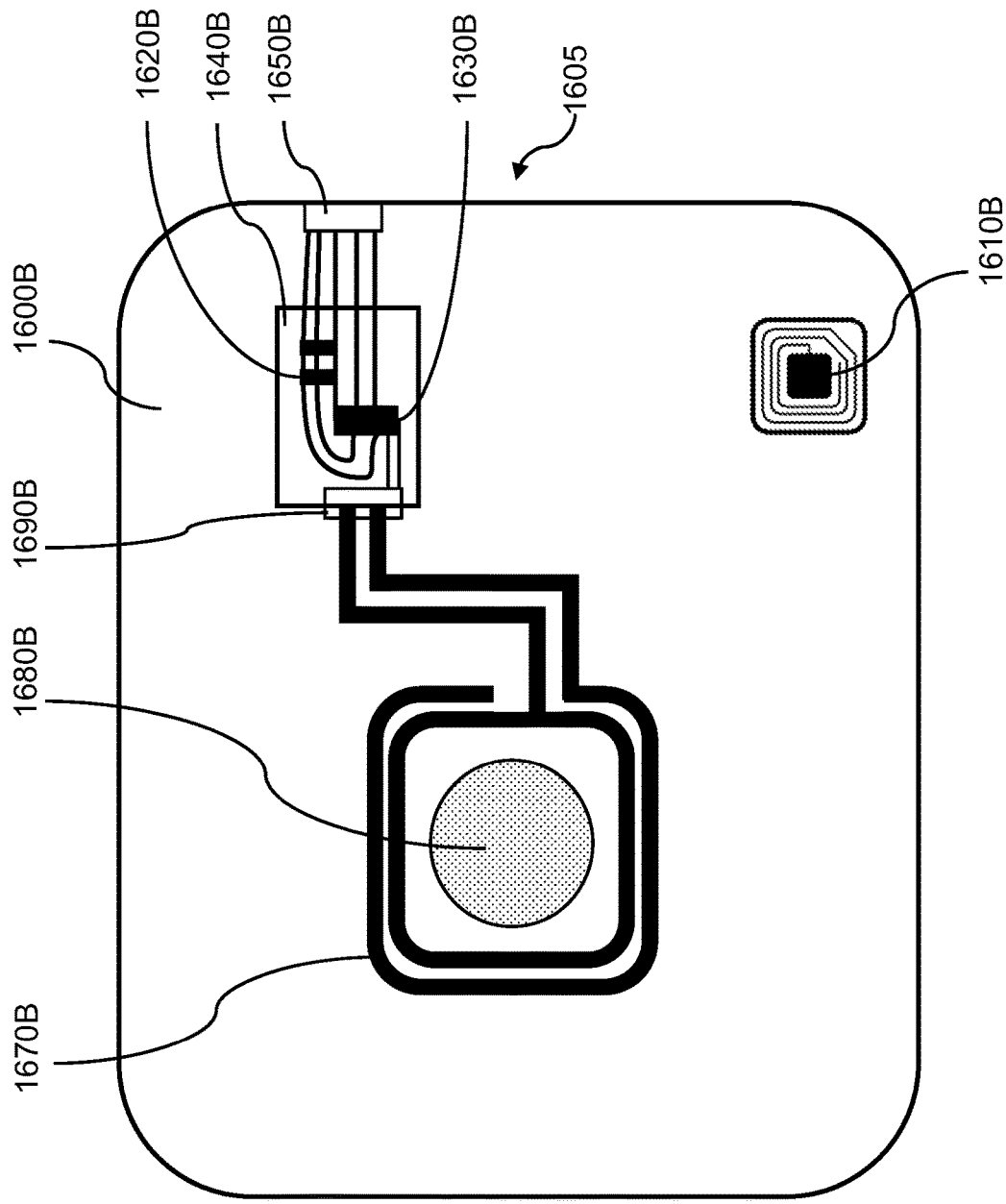
FIG. 16B depicts an exemplary embodiment of a fluid chamber or bladder.

FIG. 16B depicts an exemplary embodiment of a fluid bladder or chamber 1600B of a cushion, such as an immersion cushion, in which control electronics 1605B are included in the construction of the fluid bladder or chamber. One or more embedded identification and/or communication devices 1610B, such as a BLE beacon, RFID tag, or other wireless digital ID, may be included in the fluid chamber 1600B. The chamber 1600B may include one or more sensors 1620B, such as a MEMS sensor for measurement of pressure, force, temperature, humidity, orientation, deflection, and/or wetness. Additionally or alternatively, one or more piezo film sensors or capacitive sensors are used to sense presence or direct force. In an embodiment, one or more processors 1630B may be included directly in the construction of the chamber 1600B, for example on an embedded rigid or flexible printed circuit board assembly (PCBA) 1640B that has an interface and communications electronics for implantable sensors/devices. The one or more processors 1630B may be communicatively coupled, via wired or wireless devices/means, to one or more external devices (e.g. management system 1105). In another embodiment, processing is done off-board of the chamber 1600B, and the sensors 1620B are connected to an external device for power and communication with a physical connection 1650B.

In an embodiment, one or more conductive ink printed circuits may be printed onto the interior or exterior of the layers of the cushion 1600B. The conductive ink printed circuits may be connected to one or more sensors, rigid or flexible PCBA's, or other components of the cushion 1600B. Additionally or alternatively, the conductive ink may be printed to create an antenna for communication with external devices.

In the embodiment of FIG. 16B, conductive ink is printed on the outside of the upper layer 1520 of a 2-piece cushion. The conductive ink pattern 1670B is comprised of at least two independent conductive loops separated by a small gap. This pattern is drawn around a target area 1680B of the chamber most likely to be the location of user incontinence. Additionally or alternatively, the target area 1680B may be the extruded or formed part of the fluid chamber 1600B in an area for which it may be difficult to print a pattern and which may shed any moisture towards the printed conductive loops. The printed conductive loops 1670B are connected via a connection 1690B to a flexible or rigid PCBA 1640B that includes a pre-processing and/or amplification circuit which couples the conductive loops to the input of a processor 1630B. The processor 1630B monitors for either a decrease in resistance between the two loops or a closed circuit (presence of voltage), both of which may indicate wetness, to determine if the chamber 1600B is wet and therefore there has been an incontinence event. In an alternative embodiment, the printed pattern 1670B may be used as a resistive heating element of the PCBA 1640B to heat the chamber 1600B and may be controlled by the one or more processors 1630B of the PCBA. Control of the heating element (e.g. on and off) may be done automatically by one or more processors 1630B of the chamber 1600B based on readings from an internal or external temperature sensor 1620B, or it may be turned on and off manually by the user via a switch of the chamber's control electronics 1605B or when a control signal is received from an external wireless device, such as the main processor 1125 of the management system 1105 or associated transceiver. In another embodiment, the printed pattern 1670B may be used to create TENS/electrical stimulus pads to assist with physical therapy.

One or more electrically controlled fluid control devices (e.g. electronically controlled valves) may be embedded in the chamber 1600B for control by the processor 1630B (or alternately processor 1125). In an example referencing the two-part cushion of FIG. 15, an electronically operated valve is placed in the channel 1540 connecting two fluid chambers 1530 and 1535 or between two groups or sections or fluid chambers. The valve receives one or more control signals from a processor 1630B of the chamber 1600B and, in response thereto, enables, disables, restricts, or expands the ability of fluid to flow through the channel 1540, for example by opening or closing the valve or partially opening or closing the valve. In another example, the fluid in the chamber 1600B is a magneto-rheological fluid and the fluid control electronics may be embedded in the chambers and sections construction so that the viscosity of the magneto-rheological fluid may be changed based on one or more control signals from one or more processors 1630B of the chamber. In another example, one or more fluid flow sensors are placed in the chambers 1530 and 1535 and/or one or more sections 1540 for monitoring and real-time adjustment of the fluid flow.

In an alternate embodiment of FIGS. 16A-16B, the control electronics 1605A and 1605B are not embedded in the cushion 1600A and fluid chamber 1600B, respectively. Instead, the PCBA 1640A and 1640B is the same PCBA 1100 of FIG. 11, and the remaining control electronics 1605A and 1605B, including the sensors, are present at one or multiple locations of the smart cushion 1600A and chamber 1600B, respectively.

Figure 17:
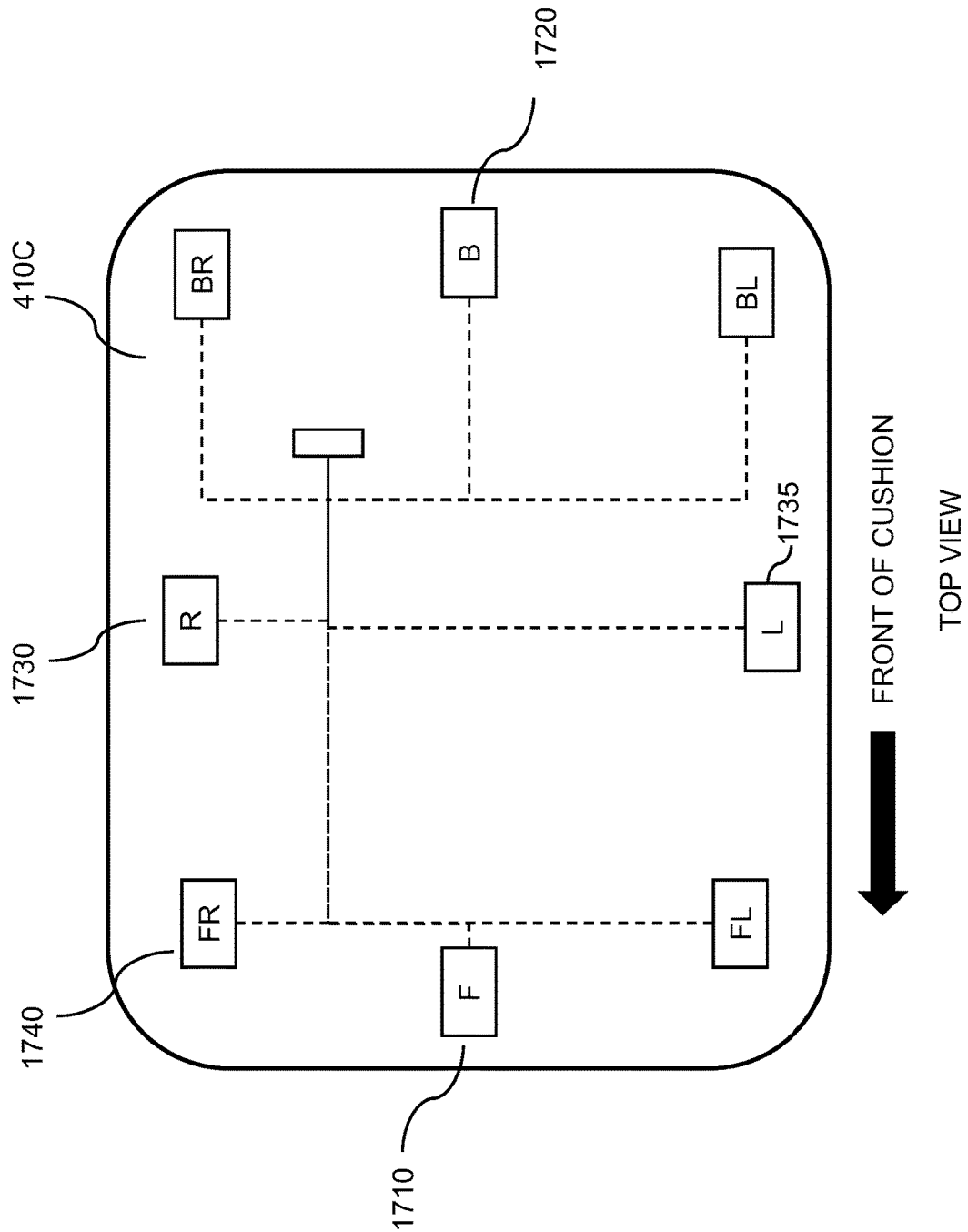
FIG. 17 depicts a smart cushion with one or more haptic feedback devices.

FIG. 17 depicts an exemplary smart cushion 1700 with one or more haptic feedback devices, also known as kinaesthetic communication devices, included in the embedded circuitry of the cushion. Haptic feedback devices refer to any technology that can create a physical sensation by applying forces, vibrations, or motions to the user. The cushion 410C includes haptic feedback devices 1710-1740 in multiple locations distributed around the cushion. The haptic feedback devices may be included, for example, in the front 1710 and back 1720 of the cushion and/or the right 1730 and left 1735 of the cushion and/or at other locations, such as the corners 1740 (e.g. front-right, front-left, back-right, and back-left) of the cushion. The one or more haptic feedback devices 1710-1740 are connected to a PCBA 1640C which includes the control electronics required for the haptic feedback devices and may include one or more processors 1630C for controlling the haptic devices. In some embodiments, the power and/or control signals for the haptic feedback devices 1710-1740 are provided externally via a connector 1650C. In an embodiment, one or more of the haptic feedback devices 1710-1740 may be speakers or may be accompanied by speakers with the goal of providing both vibration and audible guidance to the user.

The haptic feedback devices of FIG. 17 may be used to provide seating feedback and guidance to the user. In an example, the core logic 1220 of the management system controller 1170A includes a timer that calculates how long a user has been in the cushion, and thereby in the seat. When the user has been IN SEAT for a selected time period (e.g. one hour) based on sensor reports 1260 received from one or more sensors, it is time for the user to offload. The core logic 1220 and/or HMI manager 1230 of the management system controller 1170A then causes the processor 1125 of the management system PCBA 1100 to transmit one or more control signals, which causes the back haptic feedback device 1720 in the cushion to vibrate. The vibration of the back haptic feedback device 1720 may be accompanied by one or more other forms of audible or visual feedback similarly caused by one or more control signals transmitted from the processor 1125 of the management system PCBA 1100. This feedback serves to remind the user to offload.

When the user successfully offloads, the one or more sensors of the smart cushion 1700 will register the state change and transmit one or more sensor reports indicative of the state change to the processor 1125, the processor will determine the state change from the one or more sensor reports received from the one or more sensors, and the processor, in response thereto, will transmit one or more control signals to another haptic device (e.g. right haptic device 1730) to cause the right haptic device to vibrate to notify the user that they are in a successful offload. Finally, when the processor 1125 has determined the user has offloaded long enough, the processor, in response thereto, will transmit one or more control signals to a different haptic device (e.g. front 1710 haptic feedback device) to cause the front haptic device to vibrate to alert the user that they can stop offloading. In all cases, additional audible and visible indications may be given to the user as described above. In another example, the haptic feedback may be used to discourage bad habits and/or alert the user when they are out of position. In another embodiment of FIG. 17, the processor 1630C makes the determinations and transmits the control signals to the haptic feedback devices 1710-1740.

In another embodiment, the haptic feedback devices of FIG. 17 may be used to provide driving feedback and guidance to the user of a power or manual wheelchair. In this example, the PCBA 1640C is the management system PCBA 1100 of FIGS. 11-12 or the PCBA 1640C is not present but the PCBA 1100 of the management system 1105 of FIGS. 11-12 is present. Many wheelchair users have limited vision or limit ability to move and look around themselves. In an example, the core logic 1220 of the management system controller 1170A receives a communication 1160 from an advanced driver assistance system (ADAS) that includes, for example, collision or step avoidance information indicating that travel in the front of the wheelchair is blocked or limited. The core logic 1220 and/or the HMI manager 1230 of the management system controller 1170A causes the processor 1125 of the management system PCBA 1100 to send one or more control signals which cause the front haptic feedback device 1710 in the cushion to vibrate. The vibration of the haptic feedback device may be accompanied by one or more other forms of audible or visual feedback similarly caused by one or more control signals from the processor 1125 of the management system PCBA 1100.

Use in Other Cushion Types

Figure 18:
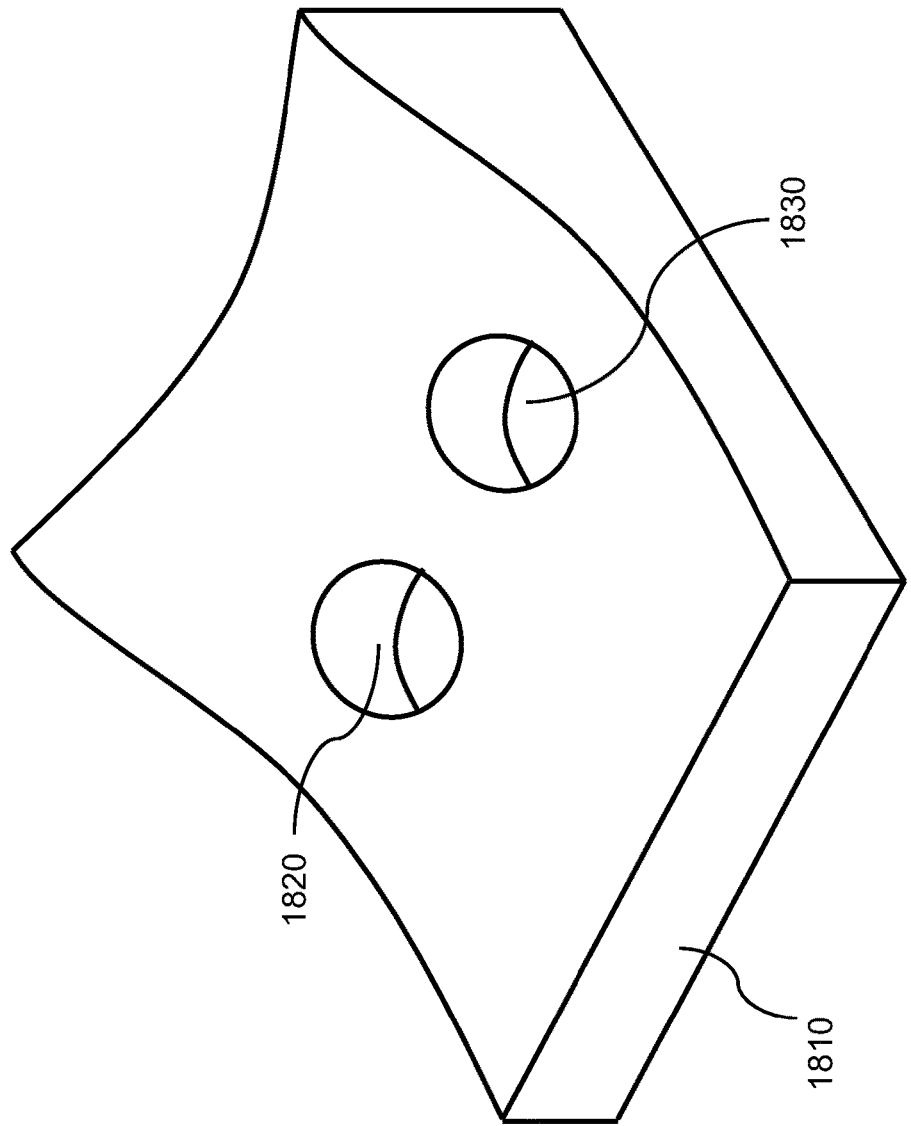
FIG. 18 depicts a cushion with relief holes/voids to remove pressure from ischial tuberosities of a user.

Off-loading is the clinical practice of reducing or removing pressure from one area of the body (possibly to another area of the body) in an effort to reduce risk to injury—e.g., reducing the pressure under the ischial tuberosities (ITs) and increasing pressure on the thighs or other parts of the seated body. FIG. 18 depicts a positioning cushion 1810 with relief holes/voids/apertures 1820-1830 to remove pressure from the ischial tuberosities of the person sitting in the cushion.

Figure 19:
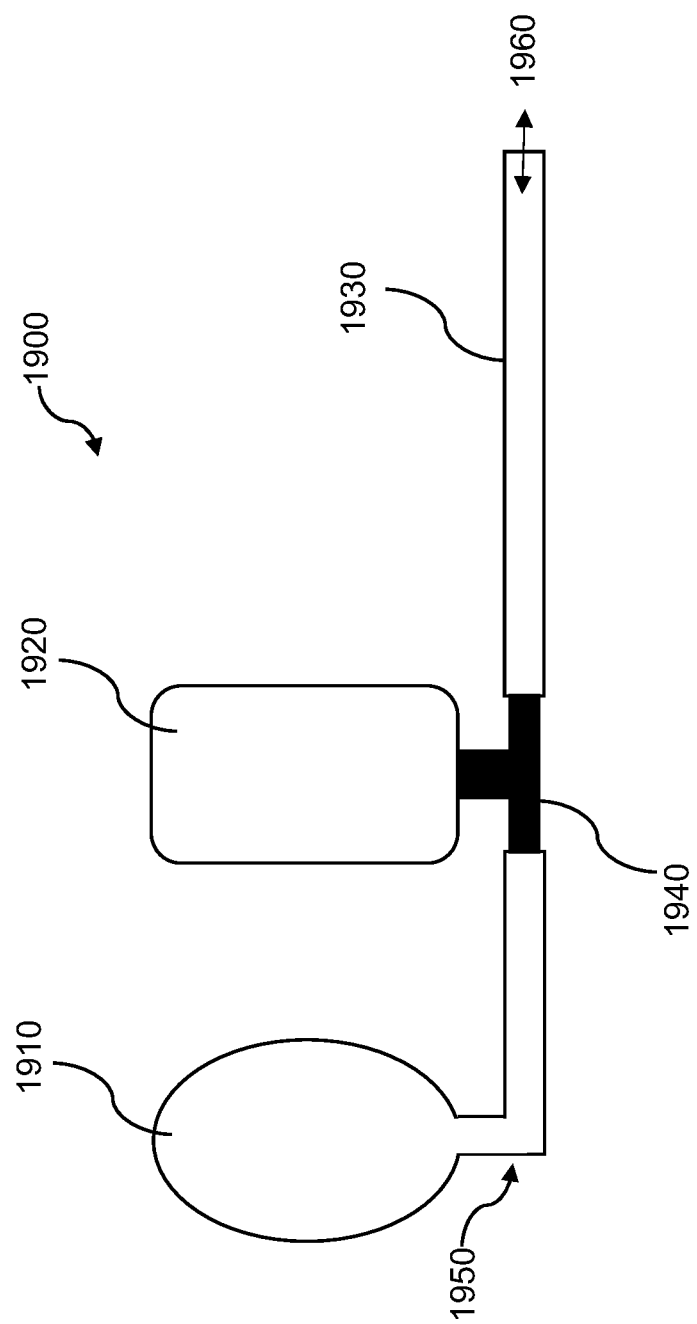
FIG. 19 depicts a fluid system that can be attached to a management system.

FIG. 19 depicts a fluid system 1900 that can be attached to a management system. In this example, one or more flexible fluid chambers or bladders 1910-1920 are connected to tubing 1930 via one or more connectors 1940 and/or molded directly into the tubing itself 1930, e.g. at a juncture 1950. The tubing 1930 can then be connected to a management system such that the pressure of the fluid inside the fluid chamber can be measured by a management system, e.g. at a valve, channel, or outlet 1960 of the tubing. In an example, the tubing 1930 may connect to the fluid tight connection of a management system, such as the fluid tight connection 970 shown in FIG. 9.

Figure 20:
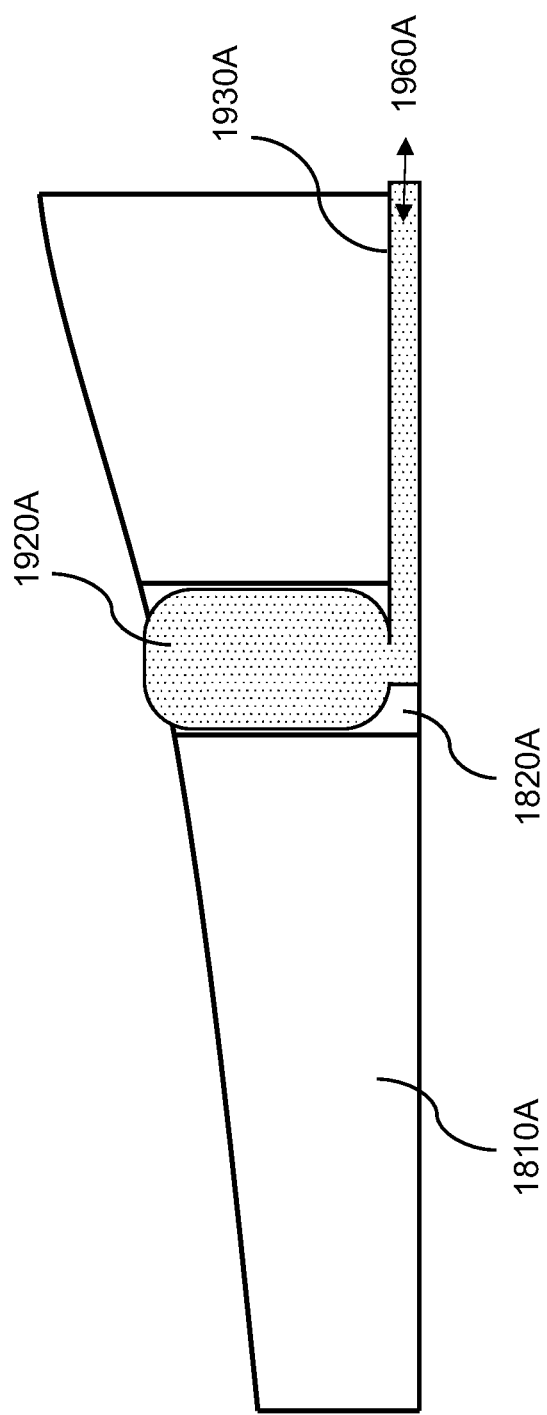
FIG. 20 depicts a cross section of a relief hole/void/aperture in a cushion through which flexible pressure balloons are inserted.

FIG. 20 depicts a cross section of a relief hole/void/aperture 1820A in a positioning cushion 1810A through which flexible fluid chamber or bladders 1920A may be inserted. The outlet tube 1930A of the fluid chamber or balloon 1920A leads to a management system at a valve, channel, or outlet 1960A of the tubing and is used as a sensor to monitor pressure in the cushion because the management system reads the pressure of the chamber or balloon at a valve, channel, or outlet of the tubing as described above and monitors changes in that pressure. The management system may compare the pressure of the chamber or balloon at a valve, channel, or outlet of the tubing 1930A to ambient pressure from an ambient pressure sensor to determine a final absolute pressure value as described above in one example.

Figure 21:
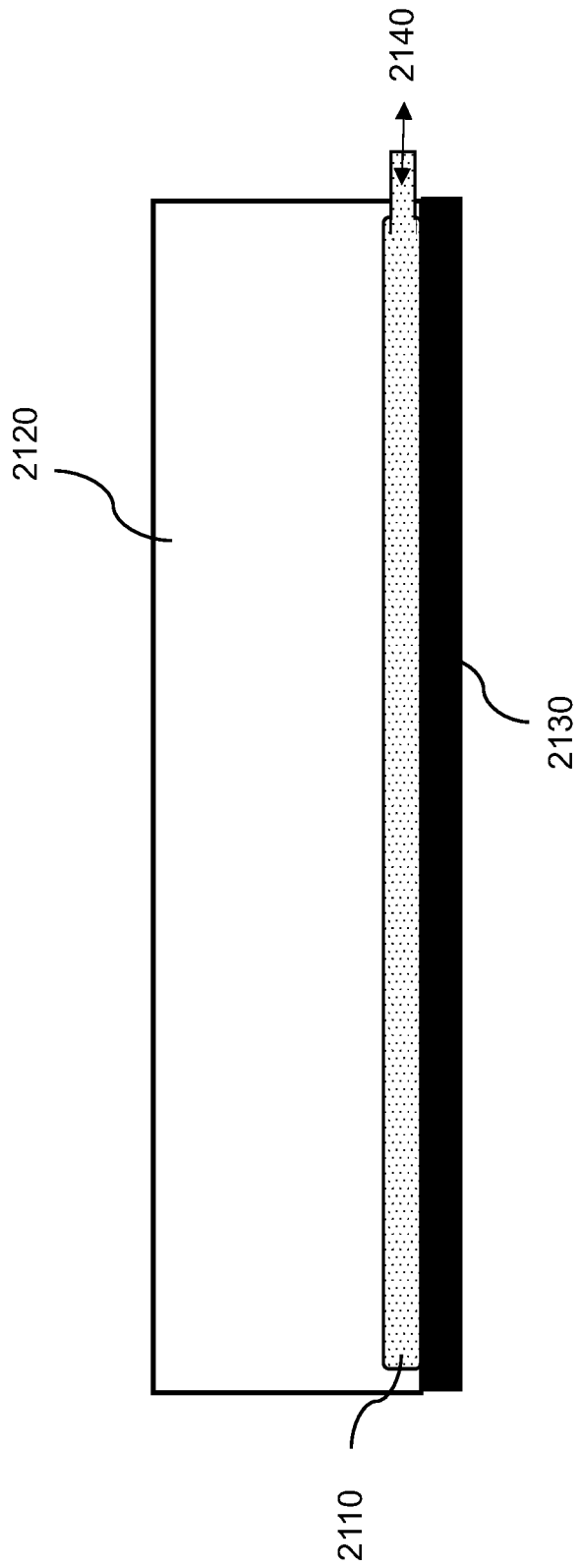
FIG. 21 depicts a cross section of an air bladder affixed to an underside of a seat cushion or to a relief area of the underside of a seat cushion so that the air bladder is between the seat cushion and a solid seat platform.

FIG. 21 depicts a cross section of a fluid chamber or bladder 2110 affixed to the underside of a seat cushion 2120 or a relief area of the underside of a seat cushion so that the fluid chamber or bladder 2110 is between the seat cushion and a solid seat platform 2130. The outlet 2140 of the fluid chamber or bladder leads to a management system and is used as a sensor to monitor pressure operating on the cushion because the management system reads the pressure of the chamber or balloon at a valve, channel, or outlet 2140 of fluid chamber or bladder as described above and monitors changes in that pressure. The management system may compare the pressure of the chamber or balloon at a valve, channel, or outlet 2140 of fluid chamber or bladder to ambient pressure from an ambient pressure sensor to determine a final absolute pressure value as described above in one example.

Using the embodiments of FIGS. 20-21 with the exemplary management system of FIG. 7, the user state can be monitored as previously disclosed. Referencing FIG. 13, alternative pressure thresholds can be determined and set for inSeatt, out of seat, and offloaded states that take into account the weight and pressure of each cushion type and geometry. In an embodiment, these target pressures are set for a user with the clinician in a clinical setting where the user is positioned in their ideal seated and offloaded position and the pressure in the flexible fluid chambers or balloons is set using the user interface of the management system.

Pressure Regulation

Pressure in the one or more fluid chambers of the fluid filled bladders previously discussed (e.g. such as a cushion 410 or fluid chamber or bladder 1910) may be regulated manually or automatically. In the simplest embodiment, a pump may be attached to the fill valve of the cushion (e.g. valve 430 of FIG. 4) directly or to the fill valve of a non-integrated management system valve to the cushion (e.g. inflation/deflation valve 730 of FIG. 7). For example, if the user's seat cushion pressure is too low, the processor 1125 of the management system 1100 may cause an output device of the HMI 1130 to beep and cause a low pressure indicator light to illuminate, as described above. The user can then inflate the cushion by attaching an air (or other fluid) pump to the inflation/deflation valve and opening the inflation/deflation valve so that air (or other fluid) may flow from the air (or other fluid) pump, through the inflation/deflation valve, and to the fluid chambers of the cushion. Air or other fluid can be added until the pressure indicator shows that the air or other fluid pressure is correct. The user can then remove the pump, close the valve, and check that the pressure is indeed correct based on feedback from the smart cushion user interface. In the event that the cushion pressure is too high, the smart cushion will beep and indicate high pressure. The user can reduce the pressure in the cushion by briefly opening the fill valve to release some air or other fluid. Additionally or alternatively, the pressure may be regulated automatically based on one or more control signals output by the processor 1125 of the management system 1105. The one or more control signals are sent based on one or more calculations of the management system controller 1170 where the calculation may determine that:

- The current pressure in the cushion is higher than the ideal pressure (e.g. state 520 FIG. 5) and fluid should be released to lower the pressure;
- The current pressure in the cushion is at the ideal pressure (e.g. state 510 FIG. 5) and fluid does not need to be added or released to raise or lower the pressure;
- The current pressure in the cushion is lower than the ideal pressure (e.g. state 530 FIG. 5) and fluid should be added to the cushion to raise the pressure; and/or,
- The user has been IN SEAT (e.g. states 510-530 FIG. 5) for too long and needs to offload (e.g. state 540 FIG. 5) which causes the cushion to change the pressure in one fluid chamber relative to another fluid chamber of the cushion causing loading to shift.

Figure 22:
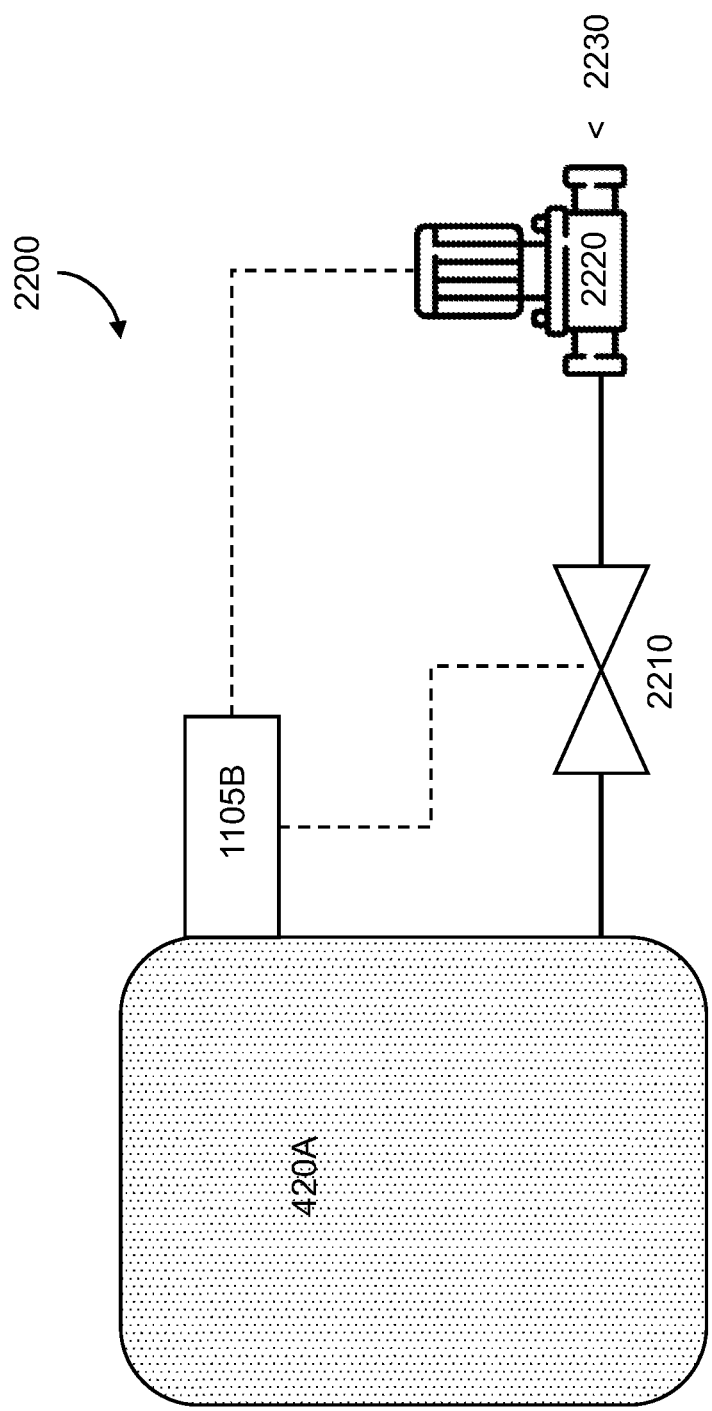
FIG. 22 depicts a block diagram of an operating management system.

FIG. 22 depicts a block diagram of a management system 2200. The management system 2200 consists of a smart cushion 410A with at least one fluid filled chamber or bladder 420A, a management system 1105A, an electronically controlled valve 2210, and, optionally, an electronically controlled pump 2220 or fluid source. The electronically controlled pump 2220 draws fluid from a reservoir 2230 which may be, for example, ambient air or a pre-pressurized fluid source.

In an embodiment, the management system controller 1170A monitors the state of the smart cushion 410A based on one or more sensor reports received by the sensor IAM 1210 on the management system processor 1125. If the core logic 1220 of the management system controller 1170A determines that the pressure in the fluid filled chamber or bladder 420A is below the ideal pressure range (i.e. state 530 of FIG. 5), then the communication manager 1240 of the management system controller causes the processor 1125 of the management system controller to transmit one or more control signals via a wired or wireless means (e.g. via a transceiver 1165 or a connection) to the electronically controlled valve 2210 to instruct and cause the electronically controlled valve to open and to instruct and cause the electronically controlled pump 2220 to pump fluid into the fluid filled chamber or bladder 420A. If the core logic 1220 of the management system controller 1170A determines that the pressure in the fluid filled chamber or bladder 420A is at the ideal pressure range (i.e. state 510 of FIG. 5), then the communication manager 1240 of the management system controller causes the processor 1125 of the management system controller to transmit one or more control signals via a wired or wireless means (e.g. via a transceiver 1165 or a connection) to instruct and cause the electronically controlled valve 2210 to close or remain closed and to the electronically controlled pump 2220 to instruct and cause the electronically controlled pump to not pump fluid into the fluid filled chamber or bladder 420A (e.g. to turn the pump off or to remain off). If the core logic 1220 of the management system controller 1170A determines that the pressure in the fluid filled chamber or bladder 420A is above the ideal pressure range (i.e. state 520 of FIG. 5), then the communication manager 1240 of the management system controller causes the processor 1125 of the management system controller to transmit one or more control signals via a wired or wireless means (e.g. via a transceiver 1165 or a connection) to the electronically controlled valve 2210 to instruct and cause the valve to open and to the electronically controlled pump 2220 to instruct and cause the electronically controlled pump to pump fluid from the fluid filled chamber or bladder 420A, e.g. to the atmosphere or environment, or to maintain the pump in an off position for a certain amount of time to enable the fluid to escape to the atmosphere or environment to thereby reduce the pressure in the fluid chamber or bladder.

When the electronically controlled valve 2210 receives the control signal from the processor 1125 instructing the valve to open, the electronically controlled valve opens or otherwise moves to the pump position. The electronically controlled valve 2210 may be instructed to open or otherwise move to a position that allows fluid to escape from the fluid chamber or bladder 420A for a certain amount of time to the atmosphere or environment, thereby reducing the pressure in the fluid bladder. When the electronically controlled valve 2210 receives a control signal from the processor 1125 instructing the valve to close, the electronically controlled valve closes or otherwise moves to the no pumping position. When the electronically controlled pump 2220 receives the control signal from the processor 1125 instructing the pump to pump fluid, the electronically controlled pump pumps fluid (through the electronically controlled valve 2210) to the fluid chamber or bladder 420A until one or more control signals are received from the processor instructing the electronically controlled pump to stop pumping fluid. When the electronically controlled pump 2220 receives the control signal from the processor 1125 instructing the pump to stop pumping fluid, the electronically controlled pump stops pumping fluid (through the electronically controlled valve 2210) to the fluid chamber or bladder 420A. In some embodiments, the electronically controlled pump 2220 is replaced with a pressurized fluid source, such as a carbon dioxide ($CO_2$) or nitrogen filled, pressurized canister.

In an embodiment, an optional electronically controlled pump 2220 is not included, and the electronically controlled valve 2210 is vented to the atmosphere when in the open position. The management system controller 1170 determines, based on one or more sensor reports, that the user is not in the seat (e.g. out of seat 550) and causes the processor 1125 to transmit one or more control signals to the electronically controlled valve 2210 that causes the valve to open. Once the internal pressure of the fluid chamber or bladder 420A reaches at or near atmospheric pressure (as determined by the management system controller 1170 based on one or more sensor reports from one or more sensors of the management system 1105), then one or more additional control signals are sent to the electronically controlled valve 2210 that causes the valve to close.

The methods disclosed above may be used to individually control the pressure in a multi-chambered cushion using a single controller and multiple sets of sensors, valves, and actuators. Additionally or alternatively, in a multi-chambered cushion, logic may be included in the core logic 1220 of the controller 1170A to load and unload sections or groups of fluid chambers of a smart cushion using one or more of the above methods in a pattern that adds and removes pressure from areas of skin in contact with the cushion in a regular or messaging pattern to provide an automated offloading state (e.g. 540) to portions of the cushion contact area for predefined periods of time.

Alternative to Pressure Management

In the case where use of immersion or hybrid cushion construction is not preferred, time in seat and skin health may be monitored by other non-pressure-based means with capacitive, ultrasonic, radar, and other sensor technologies.

Figure 23:
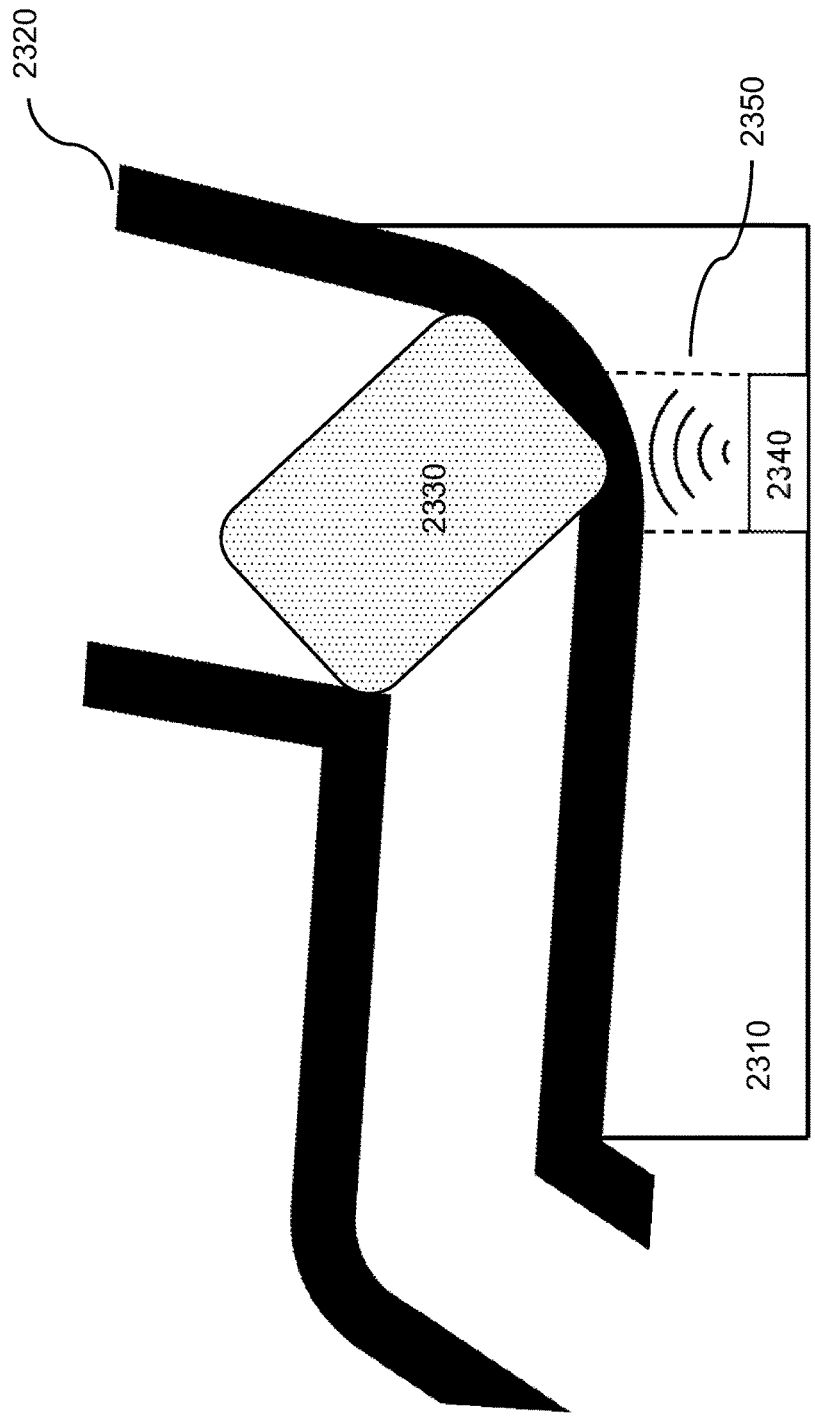
FIG. 23 depicts a side view cross section of a person seated in a cushion with embedded non-contact sensors.

FIG. 23 depicts a side view cross section of a person seated in a cushion 2310 made of foam or a similar material with one or more embedded non-contact sensors. In this example, the person has a tissue and fat layer 2320 and a skeletal structure indicated by the box 2330, which is meant to represent the person's ischial tuberosities (ITs). One or more sensors 2340 are embedded in the cushion 2310 to measure the distance to the person's skeletal structure 2330. In an exemplary embodiment, a capacitive sensor and a millimeter wave (mmWave) radar sensor are both embedded in the cushion 2310 approximately below the person's ITs. The mmWave radar sensor is configured using, for example, a properly tuned CFAR filter implementation to ignore the cushion material, clothing, and fatty tissue of the person, so that it measures the distance to the person's skeletal structure 2330. At the same time, the capacitive sensor is configured such that it measures the closest distance to the person's skin 2320. In an alternative embodiment, the capacitive sensor is replaced with an ultrasonic, IR, or other low-cost, non-contact sensor that takes measurements through a small offloading hole/aperture 2350 or channel in the cushion (e.g. hole/void/aperture 1820 of FIG. 18) and, similar to the capacitive sensor, measures the distance to the cushion/clothing interface. This configuration allows for the difference between the tissue interface and bone structure of the user to be calculated and compared. In an embodiment, one capacitive or ultrasonic sensor is used under each IT, and a single radar is used to measure the distance to the skeletal structure 2330. Alternatively, a separate radar sensor may be used to measure the distance to the skeletal structure 2330 under each IT.

In an exemplary embodiment, sensor reports from one or more sensors 2340 of the cushion 2310 are received by a processor 1125 (e.g. of the smart cushion PCBA 910A).

The sensor reports from one or more first sensors (e.g. the capacitive, ultrasonic, or IR sensor) are distance measurements to the skin, clothing, or user/cushion interface. The one or more distance measurements are used by the core logic 1220 to determine whether the user is in the seat (e.g. states 510-530 of FIG. 5) or out of the seat (e.g. 550 of FIG. 5). The determination of in-seat and out-of-seat are calculated based on one or more predefined rules using pre-configured distance threshold settings from memory. In an example, the pre-configured distance threshold settings in memory are configured and saved when the seating system is first set-up for the user as part of the installation process. The core logic 1220 may notify the user via the HMI 1130 of the system 1105 of their current state, changes in state, or reminders to change state based on the determined current state and/or the last state. Additionally or alternatively, the core logic 1220 may transmit one or more communication signals with the user's current state, changes in state, or reminders to change state based on the determined current state and/or the last state.

Sensor reports from one or more second sensors (e.g. the radar) are bearing and range measurements or Cartesian (x, y, z) measurements to the person's ischial tuberosities (ITs) 2330. The one or more distance measurements may be used by the core logic 1220 to determine whether the person is properly positioned in the seat so that their IT's line up with the offloading reliefs in their cushion, where the pre-configured IT location is retrieved from memory and is compared to the current IT position reported by the one or more second sensors. In an example, the pre-configured IT location settings in memory are configured and saved when a seating system associated with the management system 1105 is first set-up for the user as part of the installation process. The core logic 1220 may notify the user via the HMI 1130 of their current state, changes in state, or reminders to change state based on the determined current state and/or the last state. Additionally or alternatively, the core logic may transmit one or more communication signals with the user's current state, changes in state, or reminders to change state based on the determined current state and/or the last state.

In an exemplary embodiment of the system of FIG. 23, the distance to the skin, clothing, or user/cushion interface measured by the first sensor is compared to the position of the associated IT measured by the second sensor to determine offloading status (e.g. 540 FIG. 5). In an example, the distance measurement of the first sensor is subtracted from the vertical distance to the IT (part of the x, y, z position sensor report) of the second sensor. This difference is an approximate measure of the thickness of the tissue and fat layer 2320 at the IT. If this difference value is less than a predefined value, stored in memory, then one or more signals may be transmitted to cause the HMI 1130 to notify the user or a communication will be transmitted to be sent to another device indicating that the user needs to offload. If this difference is greater than a predefined value, stored in memory, then one or more signals may be transmitted to cause the HMI 1130 to notify the user or a communication will be transmitted to another device to alert that the user has successfully offloaded.

In an exemplary embodiment of the system of FIG. 23, the distance to the skin, clothing, or user/cushion interface measured by the first sensor is compared to the position of the associated IT measured by the second sensor to determine skin health and one or more processes of the smart cushion controller 1170 identify a deviation in the thickness of the tissue and fat layer 2320 at the IT over time. In one example, a static machine learning model is pre-trained to recognize changes in the tissue thickness over time that may indicate the formation or danger of formation of a pressure sore. The model may be trained prior to use using research data or may be trained in-use by the user during a defined amount of time where a "nominal" data set is captured and learned by the model over the first days or weeks of use. In another example, a dynamic machine learning (ML) model is used that is continuously incorporating received sensor data and updating itself. If the ML model identifies a change in tissue thickness as a possible risk of pressure injury formation, then one or more signals may be transmitted to cause the HMI 1130 to notify the user or a communication will be transmitted to another device indicating the risk to the user.

In an embodiment, the sensor reports of the radar sensor (second sensor) are received as a list of many points with unique x, y, and/or z coordinates. The pressure management controller 1170A includes a process which accepts one or more sensor reports from the second sensor, which consists of a list of unique points and identifies from the list of points a point that represents the location of the IT. In an embodiment, the process is a machine learning model that has been trained to identify the prominent protrusions of the IT from the background points and assign a new position (x,y,z coordinate in space) to the identified IT, which is used by one or more processes of the pressure management controller 1170A for one or more of the functions previously described.

Figure 24:
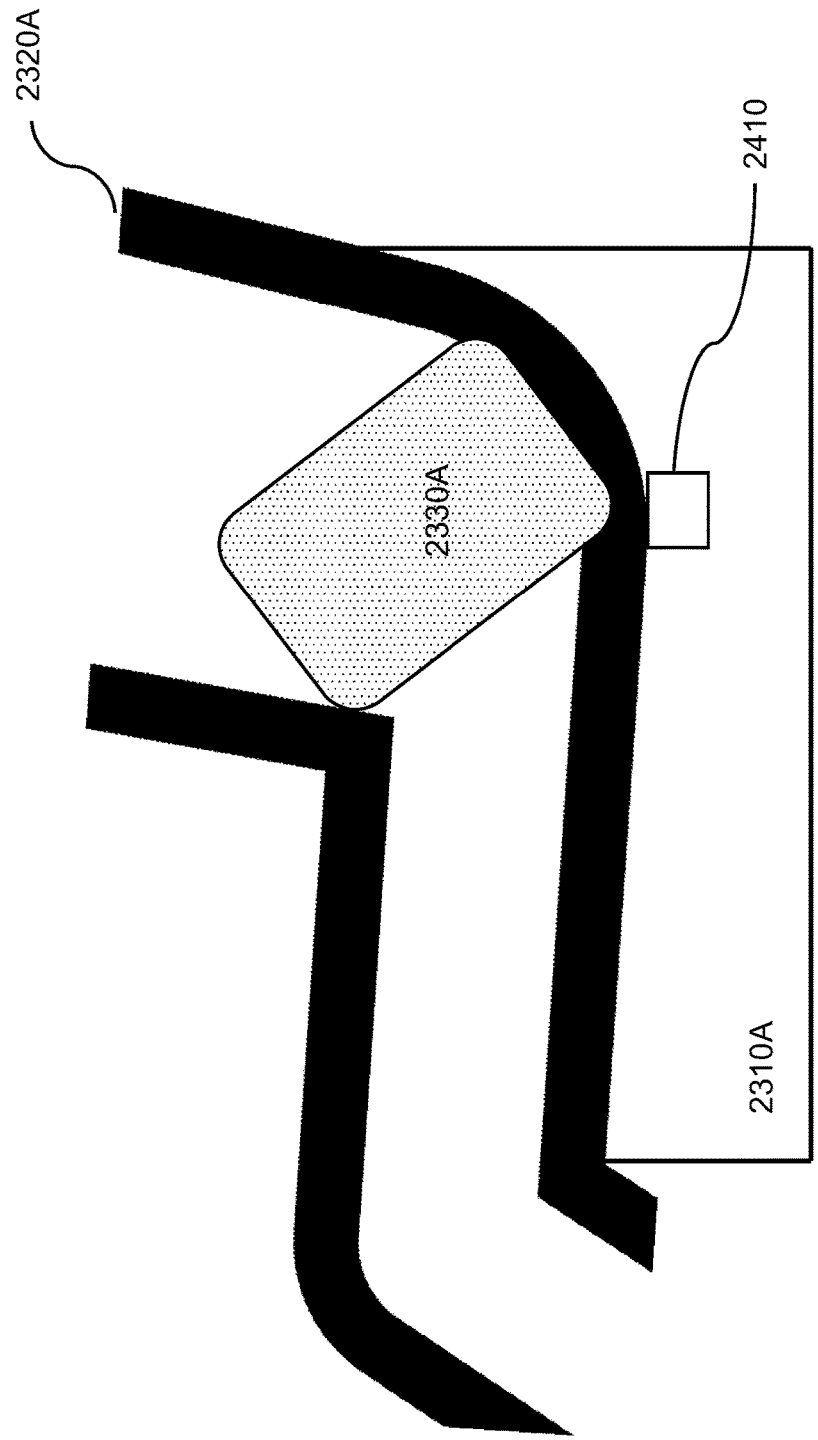
FIG. 24 depicts a side view cross section of a person seated in a cushion with embedded ultrasonic sensors.

FIG. 24 depicts a side view cross section of a person seated in a smart cushion 2310A made of foam or a similar material with embedded ultrasonic sensors 2410. In this example, the person has a tissue and fat layer 2320A and a skeletal structure indicated by the box 2330A, which is meant to represent the person's ITs. One or more ultrasonic sensors 2410 are embedded in the cushion 2310A to measure the acoustic response of the users fatty tissue 2320A. In an exemplary embodiment, ultrasonic transducers are embedded in the material of the cushion so that they are positioned near key interfaces, such as the ITs and so that they are in contact with the users clothing.

In an example, a wheelchair user transfers into a wheelchair with a smart cushion having embedded sensors per FIG. 24. Prior to the transfer, the one or more ultrasonic sensors 2410 transducers could ring or vibrate at a typical frequency, or within a typical frequency range, stored in memory. While the one or more sensor reports of the ultrasonic sensors were within this predefined range, it was determined by the management system controller 1070A that the user was not in the seat (e.g. state 550 of FIG. 5). When the user transfers into the seat, the ringing/vibration of the ultrasonic sensor transducer is damped, which puts the response from the sensor below a threshold, retrieved from memory, and causes the management system controller 1070A to calculate that the user is in the seat. In this way, user presence is determined based on one or more sensor reports from one or more ultrasonic sensors 2410 embedded in the smart cushion 2310A. When the wheelchair user transfers out of the wheelchair with the smart cushion, the absence of damping (e.g. for the ultrasonic transducers) causes a change in the sensor reports that is read by the processor of the smart cushion 2310A.

In an exemplary embodiment, the management system controller 1070A may include one or more machine learning engines which monitor the ring/vibration of the ultrasonic sensor transducer while the user is seated and use the vibration information (e.g. from the one or more sensor reports) to calculate a probability of developing a pressure injury (Ps) for the user. In this way, the changes in the response of the transducer (i.e. the change in damping) may be used to predict pressure injuries. The one or more ultrasonic sensor reports is read by a processor 1125 of the smart cushion. In one example, a static machine learning (ML) model is pre-trained to recognize changes in the tissue thickness overtime that may indicate the formation or danger of formation of a pressure sore. The machine learning model may be trained prior to use using research data or may be trained in-use by the user during a defined amount of time where a "nominal" data set is captured and learned by the machine learning model over the first days or weeks of use. In another example, a dynamic ML model is used that is continuously incorporating received sensor data and updating itself. If the ML model identifies a change in ultrasonic sensor damping as a possible risk of pressure injury formation, then one or more signals may be transmitted (e.g. by the pressure management controller 1170A of the processor 1125) to cause the HMI to notify the user or to transmit a communication to another device indicating the risk to the user.

Based on one or more outputs of the pressure management controller 1170A, the processor 1125 may be configured to send one or more control signals which cause a user feedback via the HMI 1130. Additionally or alternatively, the pressure management controller 1170A may cause the processor 1125 to transmit one or more control instructions to a motor controller, which controls one or more actuators (e.g. of a seating system of a wheelchair).

Figure 25:
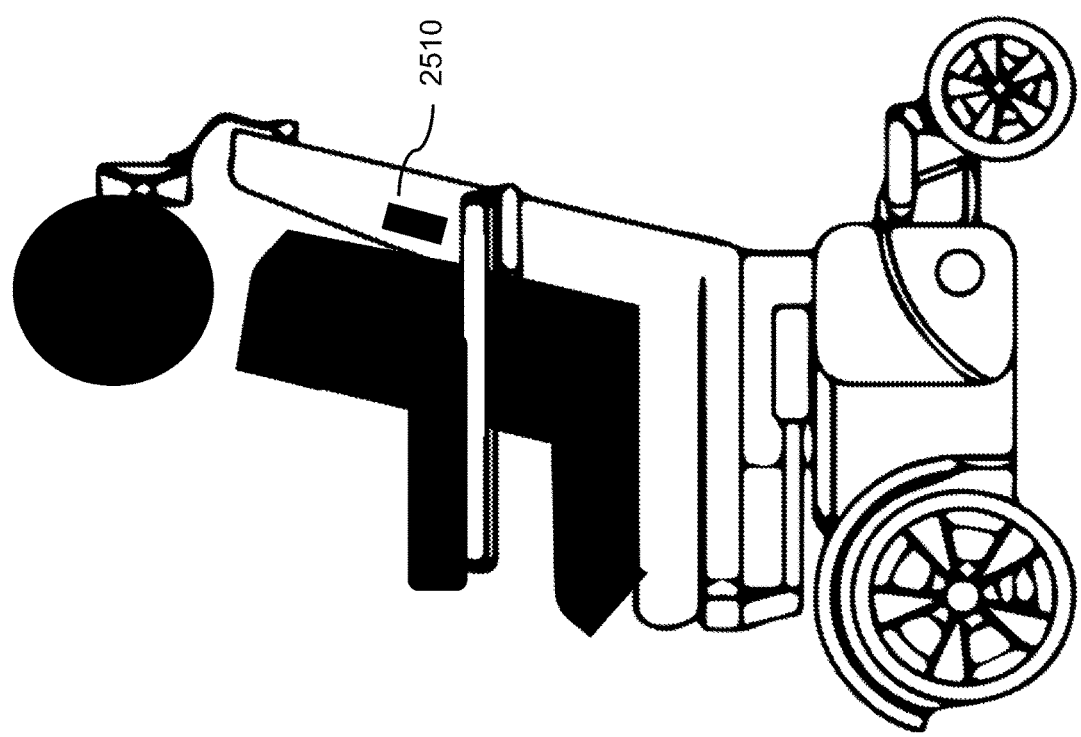
FIG. 25 depicts a seat back cushion with an embedded or attached sensor.

FIG. 25 depicts a smart back cushion of a wheelchair with an embedded radar sensor 2510. In the example, the radar sensor 2510 may be a mmWave radar configured to monitor the heartrate and/or respiratory rate of the person sitting in the seat of the wheelchair and the smart back cushion. In an exemplary embodiment, the a pressure management controller 1170A of the smart back cushion receives one or more sensor reports from the radar sensor 2510 embedded in the smart cushion, where the one or more sensor reports provide a distance to the chest wall of the user sitting in the seat. One or more calculations of the pressure management controller 1170A of the smart back cushion on the processor 1125 use the one or more sensor reports to calculate one or both of the absolute and relative displacement of the chest wall over time. Based on the periodicity of the displacement change over time, the heart rate and/or respiratory rate can be estimated for the user. The calculated heart rate may then be displayed to the user via the HMI 1130 of the smart cushion or on an application on a paired smart device (e.g. smart device 330A).

Multi-Sensor Integration

Pressure injuries, also known as pressure injuries or pressure ulcers, are caused by a variety of intrinsic and extrinsic factors. Some of these factors, such as poor nutrition, use of steroids, and age may be difficult to track with sensors, but may be known as part of a user profile (e.g. in memory 1110). Other factors, such as pressure, temperature, humidity, and friction/shear force on an area of the body may be assessed using one or more sensors in a smart cushion or cushion cover. For purposes of explanation, assume that the probability of developing a pressure ulcer is some function of the above variables described by the equation:

$$P_S = K * f(\text{age, steroid use, pressure, temperature, humidity, shear, and/or time-in-seat}) \quad \text{Eq. 1}$$

where $P_S$ is the estimated probability of a pressure injury, K represents a constant, and f is age, steroid use, pressure, temperature, humidity, shear, and/or time-in-seat. The constant K may be a positive or negative dimensionless number used to bias or correct the results of the base function. In an embodiment, one or more constants may be calculated based on intrinsic user factors, such as poor nutrition, use of steroids, and age retrieved from memory 1110 as part of a user profile.

The smart cushion, including the embodiments previously disclosed, lays the foundation for a fused or multi-factor approach to avoiding pressure injuries. In an embodiment, a pressure injury avoidance function of the core logic 1220 of the management system controller 1170A may be configured such that it executes a version of Eq. 1 (e.g. on processor 1125) and outputs a prediction of pressure injury danger or pressure injury probability based on the one or more inputs. One or more of the necessary inputs for this complex function are provided by one or more sensors of a smart cushion or a smart cushion cover and/or by one or more external/auxiliary sensors connected to the smart cushion. In an embodiment, one or more sensor reports is received by the management system controller 1170A of the smart cushion, where the one or more sensor reports are preprocessed and time-stamped by the sensor IAM 1210 and input to the core logic 1220 of the management system controller, which calculates (with an equation or program from memory) the pressure injury probability with the one or more sensor reports and data from memory. The one or more sensors of the smart cushion and/or one or more external/auxiliary sensors provide sensor reports which include data that is at least one of raw sensor data, preprocessed sensor data, orientation, location, position, distance, time, force, mass, weight, pressure, temperature, heart rate, pulse, respiratory rate, blood pressure, wetness, humidity, friction, shear force, chemical, moisture, electro-dermal, bio-electric impedance, galvanic skin resistance, pH, salinity, event, state, and/or action data as appropriate.

The pressure injury probability is used by the management system controller 1170A to alert the user to the need to take action and to automatically cause actions on the seating system in some embodiments. In an example, the management system controller 1170A of the smart cushion may calculate that the user currently has a high probability of pressure injury. The core logic 1220 may send an input which causes the HMI manager 1230 to cause one or more actions of the HMI 1130, such as sounding an alert, causing haptic feedback, or displaying a visual indication that the user's probability of pressure injury is high. Given this feedback, the user may then choose to execute an offload, reposition, or take some other action which may be suggested by the HMI 1130. Additionally or alternatively, the core logic 1220 may provide an input to the communications manager 1240 which causes the processor 1125 of the system to send one or more messages or control signals via a wired or wireless means that:

Communicates the high risk of pressure injury to another device such as an application on a smart device, or, Causes one or more predefined actions to be performed by a power seating assembly of wheelchair.

In an exemplary embodiment, the smart cushion is communicatively coupled via Bluetooth Low Energy to a smart phone such that the communications manager 1240 causes a wireless message to be sent, by the processor 1125 which may include a transceiver, to a second processor, of the smart device, where the message includes one or more of the calculated probability of pressure injury, one or more of the input data used to calculate the probability, the current state of the user (e.g. in-seat, out-of-seat) and/or the current state of the cushion (e.g. properly inflated, low pressure, etc.). The message is received by the second processor and used by an application on the smart device to display the information, provide push and other alerts, and allow the user to exchange control instructions with the smart cushion. In an exemplary embodiment, the user states of FIG. 5 (i.e. states 510-550) are combined by a function of the management system controller 1170A on the processor 1125 to calculate a pressure injury probability. The pressure injury probability is a function of the total time-in-seat of the user (e.g. the sum of time in states 510-540) minus the time the user offloaded (e.g. state 540) adjusted by the amount of time or percentage of time that the cushion was outside of the ideal pressure range 510 (e.g. the sum of time spent in states 520 and 530). Time outside of the ideal pressure range and in-seat leads to a higher risk of a pressure injury. Equation 2 depicts an exemplary embodiment of this implementation where the constants listed may be positive or negative. In an embodiment, one or more of the constants may be calculated based on intrinsic user factors, such as poor nutrition, use of steroids, and age retrieved from memory 1110 as part of a user profile.

$$P_S = K*[A1*f(\text{time-in-seat} - \text{time-offloaded}) + A2*f(\text{cushion-status})] \quad \text{Eq. 2}$$

where $P_S$ is the estimated probability of a pressure injury and A1, A2, and K represent constants. Equation 2 depicts an exemplary embodiment of this implementation where the constants A1, A2, and K may be positive or negative numbers used to normalize, bias, weight, or correct the results of individual functions of the equation. In an embodiment, one or more of the constants may be calculated based on intrinsic user factors, such as poor nutrition, use of steroids, and age retrieved from memory 1110 as part of a user profile The smart cushion may include one or more IMUs as previously disclosed, which measure the acceleration, rotation, and/or absolute orientation of the cushion. In an example, research shows that increased jostle or acceleration in the cushion indicates that the user has had more movement and therefore a reduced risk of pressure injuries. Additionally or alternatively, an acceleration event greater than a predefined threshold may indicate an impact during transfer and increase the user's probability of developing a pressure injury. Based on these findings, the probability of pressure injury development calculation may be modified to include a function of the accelerations measured by the one or more IMUs per Equation 3.

$$P_S = K*[B1*f(\text{time-in-seat, time-offloaded, cushion-status}) + B2*f(\text{accel})] \quad \text{Eq. 3}$$

where $P_S$ is the probability of a pressure injury and B1, B2 and K represent constants.

In an embodiment, the core logic 1220 of the management system controller 1170 may use one or more sensor reports from an IMU as an input to a neural net or other machine learning algorithm to recognize user in-seat (e.g. states 510-530), out of seat (e.g. 550), and even off-loading(e.g. 540) events based solely on the accelerations reported by the one or more IMUs of the smart cushion.

As additional data is available to more fully characterize the extrinsic pressure injury risk factors, the confidence in the probability of pressure injury increases. To this end, additional sensors such as wetness, temperature, humidity, and even shear force sensors may be added to the smart cushion. In some embodiments, the additional sensors may be added directly to the smart cushion:

- As an alternative sensor 1150 of the management system PCBA 1100, or,
- As a sensor embedded in the cushion itself (e.g. sensor 1620 FIG. 16), or,
- As a wired or wireless external sensor communicatively coupled to the smart cushion (e.g. via auxiliary port 830 FIG. 8).

Equation 4 outlines a probability of pressure injury calculation of the management system controller 1170 with the ability to accept additional sensor inputs.

$$P_S = K*[C1*f(\text{time-in-seat, time-offloaded, cushion-status}) + C2*f(\text{temperature}) + C3*f(\text{wetness/hunidity}) + C4*f(\text{shear})] \quad \text{Eq. 4}$$

where $P_S$ is the probability of a pressure injury and C1, C2, C3, C4, and K represent constants.

In some embodiments of a smart cushion, one or more temperature and/or humidity sensors may be embedded in the smart cushion. Wheelchair users are particularly susceptible to many conditions that are correlated with increased occupant temperature including pressure injuries due to sitting in a fixed position for an extended period of time. Similarly, increased humidity and/or wetness of the skin contribute to a faster rate of skin degradation and an increased risk of developing a pressure injury. The temperature, wetness, and/or humidity sensors transmit one or more sensor reports 1260 to the management system controller 1170 of the processor 1125 via wired or wireless communications. The one or more received sensor reports 1260 are accepted, and in some cases pre-processed, by the sensor IAM 1210 before passing to the original or pre-preprocessed sensor reports to the core logic 1220 of the management system controller 1170A. The management system controller 1170A determines values for the temperature, wetness, and/or humidity (e.g. moisture) of the cushion from the sensor reports and uses those values as part of the calculation of pressure injury risk using Equation 4 in an embodiment. If the pressure injury probability Ps is greater than, less than, or equal to a value (e.g. from memory 1110) then the communications manager 1240 or the HMI manager 1230 of the management system controller 1170A may cause the processor 1125 to transmit one or more communications or control signals which may initiate one or more actions of the HMI manager or another component of the management system 1105 based on the temperature and/or humidity (e.g. transmit a message to a caregiver or cause an audible or visual alert from the HMI 1130). In an embodiment, the management system PCBA 910 an auxiliary port 830 is connected to a cooling or fan system in or around the seating assembly where the one or more control signals sent by the processor 1125 causes the cooling system to pump air and therefore decrease the temperature and/or humidity of the seating system when the probability of pressure injury is too high, thereby reducing the pressure injury probability.

In an embodiment, the temperature sensor is an alternative sensor 1150 included on the management system PCBA 1100 and the wetness or humidity sensor is one or more of:
  A humidity sensor embedded in the cushion,
  An off-the-shelf incontinence sensor connected to a non-integrated add-on management system 705 via an auxiliary port 830,
  A conductive circuit printed on the cushion (e.g. 1670), or,
  A conductive pattern sewn into the seat cushion cover and connected to the management system PCBA 1100 via a connector.

Figure 26:
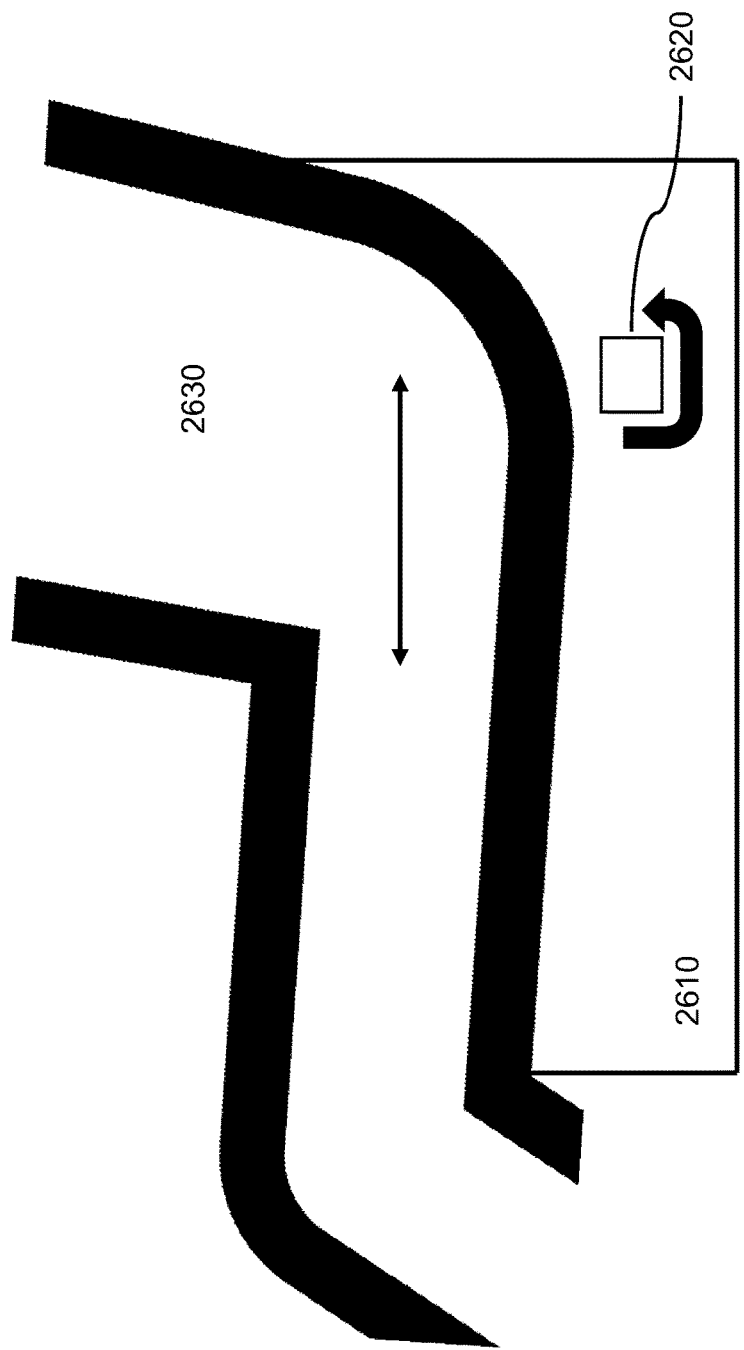
FIG. 26 depicts an exemplary embodiment of a seat cushion with an embedded IMU sensor.

Shear friction (or seating friction) on the skin is a difficult parameter to accurately measure. In an exemplary embodiment, the shear friction function (f(shear) of Equation 4) is a function that estimates the shear friction force on the user's skin based on one or more sensor reports received from an IMU where the IMU is embedded in the seat cushion or sewed into the cover of the seat cushion. FIG. 26 depicts an exemplary embodiment of a seat cushion 2610 with an embedded IMU sensor 2620. As the user 2630 slides forward or backward (or side to side which would be into and out of the page reference) the embedded IMU will sense both accelerations and rotations that will be measured by the IMU and reported to the management system controller 1170A. The sensor IAM 1210 and/or core logic 1220 of the management system controller 1170A will calculate the approximate shear friction based on one or more equations. In an embodiment, the shear friction will be based on the combination of vertical acceleration, front/back angular velocity, and side-to-side angular velocity using an equation with one or more constants. In another embodiment, the shear friction may be at least partially determined by calculating the integral of the angular velocity with respect to time and applying a factor to the result to approximate the severity of the shear friction imparted on the person 2630.

Exemplary User Interface

The goal of all the previously disclosed embodiments is to provide people and their care teams the information they need to make smart decisions in managing their skin health. Therefore, it is important to provide people actionable user feedback through one or more embodiments of a human machine interface (HMI). In the exemplary embodiment of a simple HMI of FIG. 8, HMI processing is done by the HMI manager 1230 operating on one or more processors (e.g. 1125) of the management system 1105. Additionally or alternatively, one or more user inputs 1270 may be received and processed by the HMI manager 1230 and cause the management system 1105 to take one or more predefined actions based on the received user input 1270 (e.g. cause an indicator to indicate or change the pressure and/or volume of one or more chambers or sections or groups of chambers). Further, operations performed by the HMI manager 1230 may be described as user interactions, operation of the indicators, or operation of the button.

FIG. 8 depicts an exemplary simple user interface for a management system device 700A that includes a button 810, a first multicolor indicator 820, and a second multicolor indicator 840. Additionally or alternatively, the user interface may include one or more speakers or buzzers to make sounds and/or haptic devices to generate haptic outputs. In an example, the button 810 can be used to access multiple functions of the management system including but not limited to:
  Entering a programming mode, for example by holding the button for 5-seconds,
  Saving a current pressure reading (or an average of multiple readings) as the ideal target pressure setting of the device 700A, for example with one short press while the device is in programming mode,
  Causing the management system device 700A to perform a manual pressure check and showing the results of the pressure check using the one or more multicolor indicators 840 of the management system, for example when the button 810 is pressed once and the device is not in programming mode, and/or,
  Silencing all sounds of the device 700A, such as high or low pressure, warning sounds for a set amount of time (e.g. one hour).

In an example, the multicolor indicators 820/840 are controlled by the HMI manager 1230 of the management system controller 1170A, which causes the processor 1125 to send one or more control signals which cause the one or more indicators to change state/output. As long as the management system 1105 is powered on, it continuously checks the cushion pressure (e.g. one or more chambers or sections or groups of chambers). If the user is seated in their wheelchair and the seat cushion pressure is within an ideal range 510, the management system 1105 will operate silently. Two green indicator lights (e.g. indicators 820/840) on the device 700A lets the user know that their seat pressure is in the acceptable range. If the seat pressure is too high 520 or too low 530, the management system 1105 will alert them by the processor 1125 transmitting one or more control signals to the HMI manager 1230 to cause the HMI manager to generate a beep from a speaker and a red indicator light (e.g. at indicator 820).

In another example, if the user is not in the seat (e.g. state 550), the management system 1105 will enter into low power mode 1470 until it detects the user is in the seat again (e.g. states 510-540) based on one or more sensor readings. If the user is seated in the seat and their wheelchair is turned off, the management system 1105 has the internal power (i.e. in internal energy storage 1120) to continue monitoring the cushion pressure for a period of time. The user can manually check their seat pressure in this mode by pushing the management system button. While in low power mode 1470, the processor 1125 transmits one or more control signals to the HMI manager 1230 to cause the HMI manager to generate the appropriate indicator lights (high, low, offload, or correct seat pressure indicators) will briefly flash when the button is pushed.

If the seat cushion pressure is too low, the processor 1125 will transmit one or more control signals to the HMI manager 1230 to cause the HMI manager to generate a beep at a speaker and illuminate a red low pressure indicator light 840. The user can then inflate the cushion by opening the inflation/deflation valve 730 and attaching a pump to the inflation/deflation valve. Additionally or alternatively, the system may include a pump (e.g. 2220 FIG. 22) to automatically add fluid to the cushion. The user can add fluid to one or more fluid chambers or sections or groups of fluid chambers of the cushion until the indicator lights turn green, indicating ideal pressure range 510.

If the seat cushion pressure is too high, the processor 1125 will transmit one or more control signals to the HMI manager 1230 to cause the HMI manager to generate a beep at a speaker and illuminate a red high pressure indicator light 820. The user can briefly open the management system inflation/deflation valve 730 to release some fluid and decrease the pressure. Additionally or alternatively, the system may include an electronically controlled valve 2210 to automatically release fluid from the cushion. The valve can be closed when the indicator lights turn green, indicating ideal pressure range 510

The ideal target pressure may be calculated (e.g. by one or more processes of the management system controller 1170) or may be set and stored in memory 1110 on the management system 1105. In an exemplary process for setting an ideal target pressure in memory, the first time the management system is powered on, the unit will need to be programmed. The user will work with their physical therapist, occupational therapist, or authorized technician to determine an ideal target pressure. Before the ideal target pressure is set, the processor 1125 will transmit one or more control signals to the HMI manager 1230 to cause the HMI manager to cause the indicator lights (e.g. indicators 820/840) to slowly pulse red. The user will work with their therapist or technician to ensure their seat cushion is inflated correctly and that they are seated correctly, with proper weight distribution across the cushion. This is important because the management system 1105 will use this pressure and weight distribution as a baseline for future measurements. The user will press and hold the button 810 for 5-seconds. The speaker of the HMI 1130 will sound a triple beep and both indicator lights will begin to quickly flash green. At this point the user will release the button 810. They have now entered programming mode. Within 30-seconds, the user should press and release the button 810 once to measure and store the current pressure as their target pressure. The user interface speaker will beep once and the indicator lights will blink green twice to confirm the seat pressure has been stored. If for any reason the management system 1105 needs to be reprogrammed, the user can simply follow the same steps above.

Frequent pressure offloading can help users avoid getting pressure injuries. Common offloading practices include tilting forward or back or shifting/lifting off the seat. The management system 1105 has default zones so that it can tell you whether you are at a proper offloaded pressure (e.g. in zone state 540). The offload threshold is based on the pressure relief necessary for blood to flow through tissue. When a user has reached an effective offload pressure, the management system will notify the user with one long beep and a green flashing low pressure indicator light. In many cases, a therapist may recommend a seating program to specify the length of time the user should offload and the interval of time between offloading periods. In an embodiment, users can set up seating programs and reminders using an app on a smart device.

In an embodiment, the user interface (e.g. HMSI 1130) of the management system 1105 includes a screen or touch screen. Additionally or alternatively, one or more processors (e.g. processor 1125) may include one or more transmitters/transceivers configured to communicate with one or more other devices, e.g. via Bluetooth (classic or low energy), WiFi, or cellular communications. Communications may be controlled by a communication manager 1240 of the management system controller 1170A and include transmission of data, commands, and/or control signals via wired or wireless means. In an exemplary embodiment, a processor 1125 of the management system 1105 communicates wirelessly with a computer, tablet, or other smart device 330. In an embodiment, communications may include:
  Current and/or past sensor readings,
  State determinations (e.g. one or more of states 510-540),
  State events with associated time stamps, and/or,
  Current operating parameters and/or commands to change operating parameters of the management system 1105.

Figure 27:
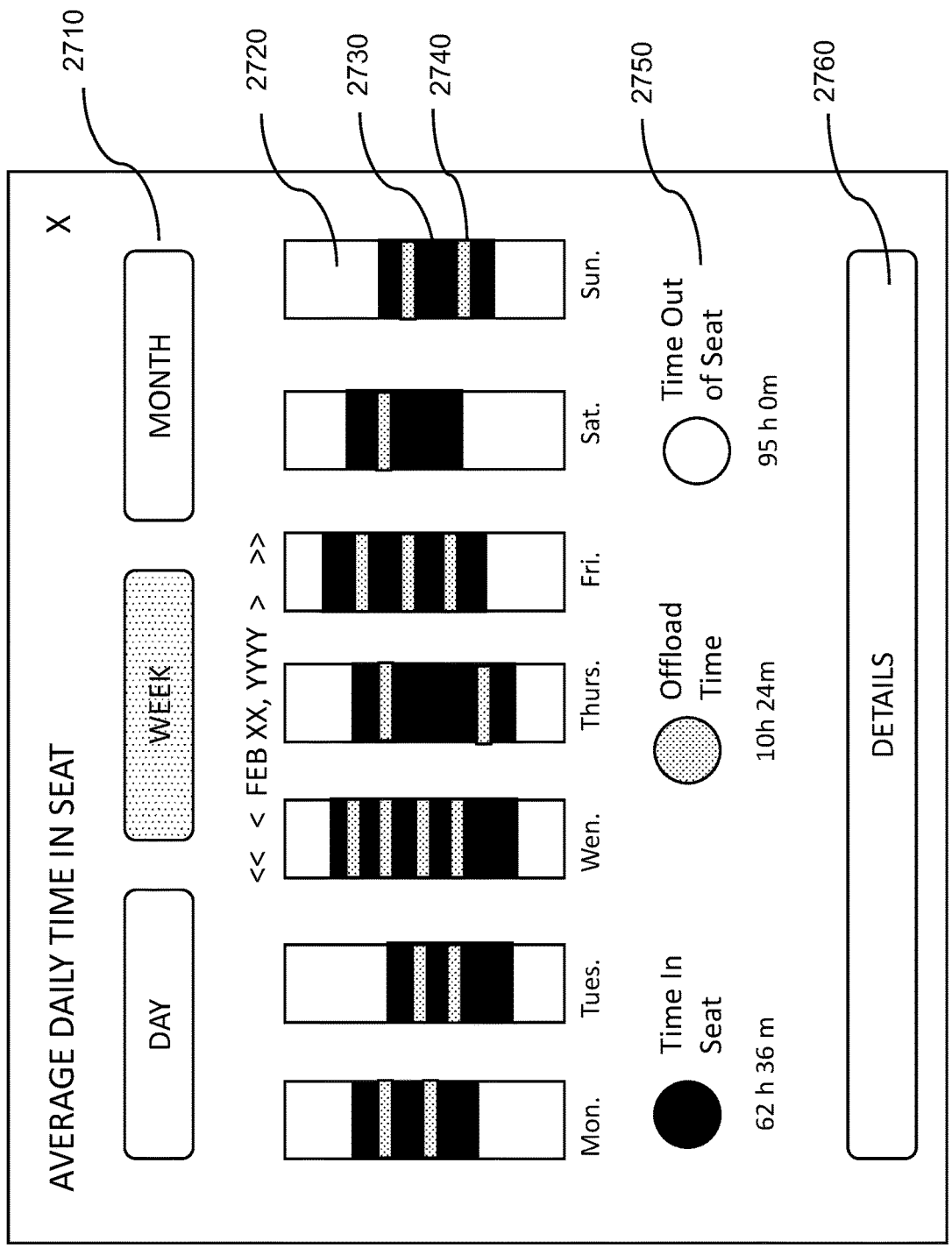
FIG. 27 depicts a user interface screen for tracking time in seat.

FIG. 27 depicts an exemplary user interface screen for average daily time inSeatt based on one or more received communications from a smart cushion system 110F and/or displayed on a screen as part of the HMI of a smart cushion or a smart device application associated with the smart cushion. In the example, the user can select a time range for the data display 2710. A graphical display 2720 of user time out-ofSeatt, time-inSeatt 2730, and offload time 2740 is shown to help the user review their seating history and plan for future actions to manage their skin health. Additionally or alternatively, the user interface includes a summary for the selected time ranges of their total amounts of time spent in each state 2750. In some embodiments, a more detailed view of the data may be available 2760 for deeper diagnostics by the user.

Figure 28:
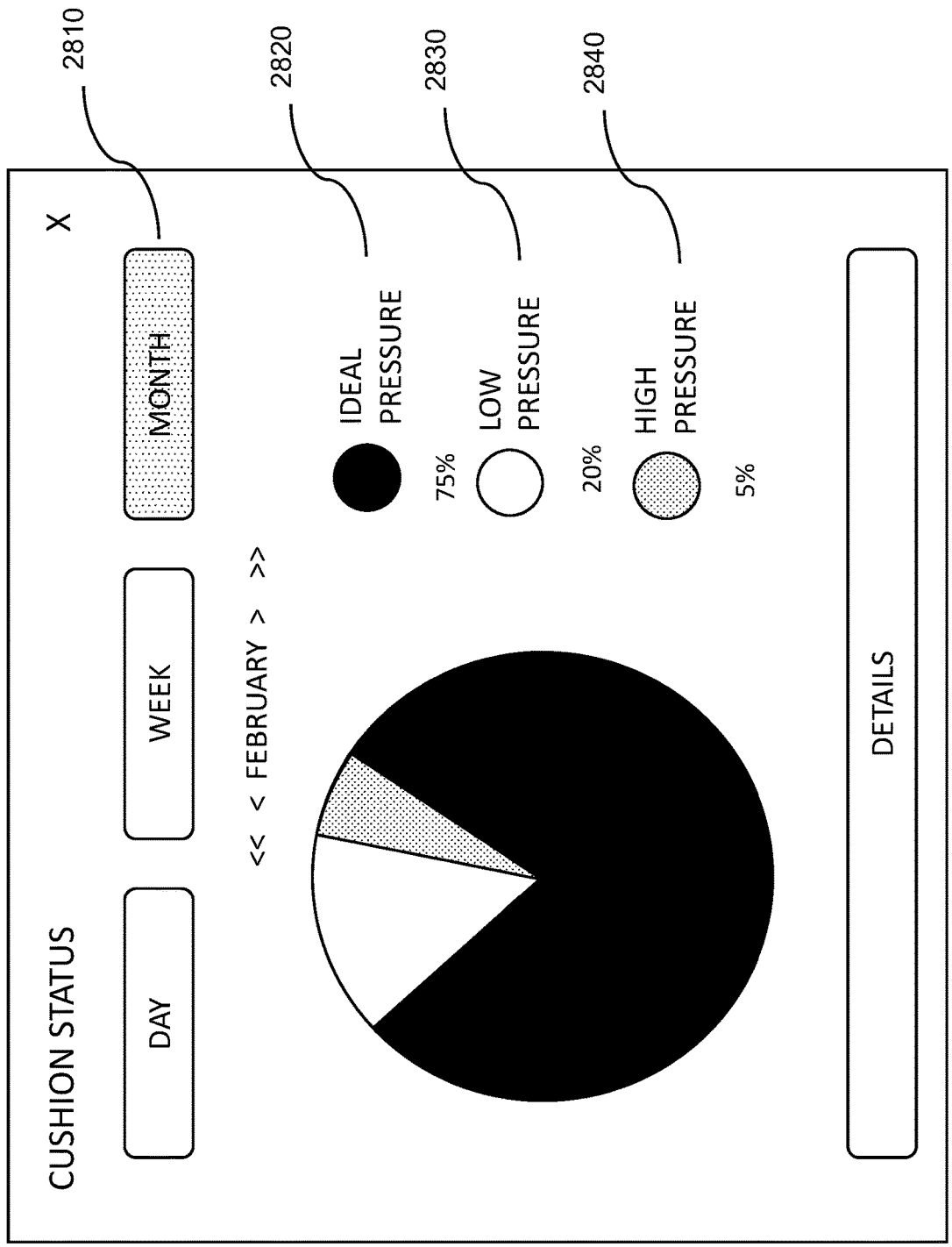
FIG. 28 depicts a user interface screen for monitoring cushion status.

In addition to time-in-seat information, it is important to know if the cushion itself is in the correct state during that seated time. FIG. 28 depicts an exemplary user interface screen for reviewing data and alerts for cushion status based on one or more received communications from a smart cushion system 110F and/or displayed on a screen as part of the HMI of a smart cushion or a smart device application associated with the smart cushion. In the example, the user can select a time range for the data display 2810. A graphical display presents the percentage of time, while the user was in seat, that their seat cushion was properly inflated 2820 versus the percentages of that time that their seat cushion was under inflated 2830 or over inflated 2840.

Figure 29:
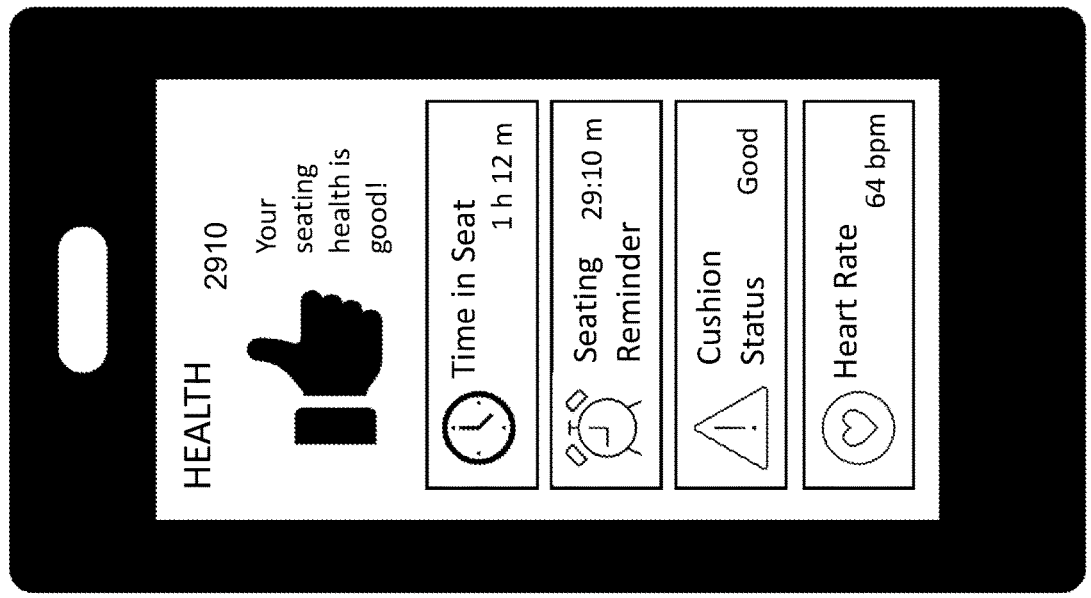
FIG. 29 depicts a user interface screen for managing seating health.

In an exemplary embodiment, the time in seat and cushion status data are combined to calculate the probability of pressure injury (e.g. as previously disclosed in Eqn. 1-4) and a seating status is calculated based on the probability of pressure injury and/or other factors. FIG. 29 depicts a user interface screen for a seating program where a seating status 2910 is calculated and displayed. Additionally or alternatively, one or more seating reminders, for example a reminder to the user to offload, may be displayed to the user based on the calculated probability or a timer based on the time since the last offload state 540 and/or the amount of time the user has been in-seat (e.g. states 510-530).

In an embodiment, a mechanized seating or bedding assembly may take one or more predefined actions based on one or more control signals received from the smart cushion. Some seat, back, leg, and head rests are produced to aid with increased need for stability in the trunk or for those at increased risk of pressure injuries from sitting. Leg rests may be integrated into the seating design and may include manual and/or powered adjustment for those users who want or need to vary their leg position. Mobile chairs may also have a tilt-in-space, or reclining facility, which is particularly useful for users who are unable to maintain an upright seating position indefinitely. This function can also help with comfort by shifting pressure to different areas over time, or with positioning in a mobile chair when a user needs to get out of the chair or be hoisted.

An active seating system may also be used for pressure relief and treatment of pressure injuries. As a non-limiting example, the management system controller 1170 may be configured to assist or enforce a weight shifting schedule on the user. This weight shifting schedule may include the management system controller 1170 sending a control signal to one or more motor controllers or drive processors of a seating assembly at predefined intervals, which cause one or more actuators in a seating system move. This would effectively adjust the positioning of various seat components to move the focus of weight on the bottom and release pressure from the bottom at set intervals (e.g. offloading). One or more of these modes of use may be enhanced by the use of one or more accompanying applications accessed via a paired smart device.

In an embodiment, the management system controller 1170A may include a pressure injury program, which takes pressure readings, time-inSeatt readings, wetness readings, and/or a temperature reading to calculate the need for user repositioning to avoid pressure injuries (e.g. using one of equations 1-4). The pressure injury program executed by the core logic 1220 and its output triggers the communication manager 1240 to send one or more wired or wireless control signals to the seating assembly to cause an adjustment to the seating system motor controller such that the user is automatically repositioned by a control signal sent from the management system controller 1170A to the seating system motor controller.

Non-Transitory Computer Readable Medium

The various operations of methods described above may be performed by any suitable means capable of performing the operations, such as various hardware and/or software component(s), circuits, and/or module(s).

The various illustrative logical blocks, modules, and circuits described in connection with the present disclosure may be implemented or performed with a hardware processor, a digital signal processor (DSP), an application specific integrated circuit (ASIC), a field programmable gate array signal (FPGA) or other programmable logic device (PLD), discrete gate or transistor logic, discrete hardware components, or combinations thereof designed to perform the functions described herein. A hardware processor may be a microprocessor, commercially available processor, controller, microcontroller, or state machine. A processor may also be implemented as a combination of two computing components, e.g., a combination of a DSP and a microprocessor, a plurality of microprocessors, one or more microprocessors in conjunction with a DSP core, or any other such configuration.

In one or more aspects, the functions described may be implemented in software, firmware, or any combination thereof executing on a hardware processor. If implemented in software, the functions may be stored as one or more executable instructions or code on a non-transitory computer-readable storage medium. A computer-readable storage media may be any available media that can be accessed by a processor. By way of example, and not limitation, such computer-readable storage media can comprise RAM, ROM, EEPROM, CD-ROM or other optical disk storage, magnetic disk storage or other magnetic storage devices, or any other medium that can be used to store executable instructions or other program code or data structures and that can be accessed by a processor. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Processes or steps described in one implementation can be suitably combined with steps of other described implementations.

Certain aspects of the present disclosure may comprise a computer program product for performing the operations presented herein. For example, such a computer program product may comprise a computer readable storage medium having instructions stored (and/or encoded) thereon, the instructions being executable by one or more processors to perform the operations described herein.

Software or instructions may be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a terminal and/or base station can obtain the various methods upon coupling or providing the storage means to the device.

For the sake of convenience, the operations are described as various interconnected functional blocks or distinct software modules. This is not necessary, however, and there may be cases where these functional blocks or modules are equivalently aggregated into a single logic device, program, or operation with unclear boundaries. In any event, the functional blocks and software modules or described features can be implemented by themselves or in combination with other operations in either hardware or software.

Having described and illustrated the principles of the systems, methods, processes, and/or apparatuses disclosed herein in a preferred embodiment thereof, it should be apparent that the systems, methods, processes, and/or apparatuses may be modified in arrangement and detail without departing from such principles. Claim is made to all modifications and variation coming within the spirit and scope of the following claims.

What is claimed is:

1. A management system for controlling a cushion, the management system comprising:
    a first pressure sensor transmitting a measured pressure of a fluid in a fluid chamber of a cushion comprising a conduit enabling the fluid to be added to or removed from the fluid chamber;
    a tube having a first end connecting to the conduit, a second end connecting to the first pressure sensor, and a valve to enable the fluid to be added to or removed from the fluid chamber through the conduit;

a second pressure sensor transmitting a measured ambient pressure of the cushion; and a processor to receive the measured pressure of the fluid, determine a pressure value of the fluid chamber based on the measured pressure and the ambient pressure, and control, based on the determined pressure value, the valve to alter the pressure value of the fluid chamber.

2. The management system of claim 1 wherein the conduit comprises a cushion valve.

3. The management system of claim 1 wherein the processor generates an alert when pressure sensed by the first pressure sensor exceeds a threshold value.

4. The management system of claim 1 wherein the tube comprises a Y-shaped connection to connect to the conduit, a tube portion leading to the second end, and the valve.

5. The management system of claim 1 further comprising a pump connected to the valve to pump the fluid to the fluid chamber of the cushion through the conduit.

6. The management system of claim 5 wherein the pump comprises at least one of a manual pump and an electronically controlled pump.

7. The management system of claim 1 wherein the valve is operable to open to enable fluid to vent from the chamber to an atmosphere or an environment.

8. The management system of claim 1 further comprising a pump to connect to the valve to pump fluid to the fluid chamber of the cushion through the conduit, wherein the processor transmits a first control signal to the pump instructing the pump to pump the fluid and a second control signal instructing the pump to stop pumping the fluid.

9. The management system of claim 1 wherein the valve is an electronically controlled valve, and the processor transmits a first control signal to the valve instructing the valve to open to provide fluid to the fluid chamber of the cushion and a second control signal instructing the valve to close.

10. The management system of claim 1 wherein the valve is an electronically controlled valve, and the processor transmits a control signal to the valve instructing the valve to open to vent fluid from the chamber to an atmosphere or environment.

11. The management system of claim 1 wherein the processor transmits a communication with a status of determined pressure value to a second processor.

12. The management system of claim 11 wherein the other processor generates an alert to a display or speaker of a device comprising the second processor.

13. The management system of claim 12 wherein the device comprises at least one of a phone, a tablet, and a computer.

14. The management system of claim 11 wherein the status comprises at least one of a low pressure, a high pressure, and an ideal pressure.

15. The management system of claim 11 wherein the status comprises an instruction to offload a user of the cushion.

16. The management system of claim 11 wherein the status comprises an out of seat state of a user of the cushion.

17. The management system of claim 11 wherein the fluid chamber comprises a plurality of fluid chambers.

18. The management system of claim 1 wherein the fluid chamber comprises a plurality of fluid chambers, the management system comprising a plurality of pressure sensors, each pressure sensor measuring fluid pressure of one fluid chamber and transmitting a sensor report to the processor with the measured pressure of the one fluid chamber, and the processor processing the sensor reports, determining a separate pressure value of each one fluid chamber based on the measured pressures in the sensor reports, and generating a separate status indicative of the each pressure value of each one fluid chamber of the cushion.

19. A method for controlling a cushion comprising:
receiving, at a processor and from a first pressure sensor, a measured pressure of a fluid in a fluid chamber of a cushion comprising a conduit enabling the fluid to be added to or removed from the fluid chamber, a tube having a first end connecting to the conduit, a second end connecting to the first pressure sensor, and a valve to enable the fluid to be added to or removed from the fluid chamber through the conduit;

receiving, at the processor and from a second pressure sensor, a measured ambient pressure of the cushion;

determining a pressure value of the fluid chamber based on the measured pressure and the ambient pressure; and controlling, based on the determined pressure value, the valve to alter the pressure value of the fluid chamber.

20. The method of claim 19, further comprising, when the pressure value is lower than a threshold pressure value:
transmitting, by the processor, a first control signal to the valve to open the valve; and
transmitting a second control signal to a pump in fluid connection with the valve, the second control signal instructing the pump to add fluid to the fluid chamber.

21. The method of claim 20, further comprising:
receiving, from the first pressure sensor, a second sensor report of a second pressure of the fluid in the fluid chamber of the cushion;
determining a second pressure value of the fluid chamber of the cushion based on the second measured pressure in the sensor report;
determining the second pressure value corresponds to at or near the threshold pressure value,
transmitting a third control signal to the valve to close the valve; and
transmitting a fourth control signal to the pump instructing the pump to stop pumping fluid to the fluid chamber.

22. The method of claim 19, further comprising, when the pressure value is higher than a selected ideal pressure value:
either (a) transmitting a second control signal to a pump in fluid connection with the valve instructing the pump to pump fluid out of the fluid chamber or (b) not transmitting the second control signal and allows the fluid to vent to atmosphere or an environment.

* * * * *